US008828961B2

(12) United States Patent
Loy et al.

(10) Patent No.: US 8,828,961 B2
(45) Date of Patent: *Sep. 9, 2014

(54) METHODS AND COMPOSITIONS TO PROTECT AQUATIC INVERTEBRATES FROM DISEASE

(75) Inventors: John Dustin Loy, Ames, IA (US); Lyric Colleen Bartholomay, Ames, IA (US); Delbert Linn Harris, Ames, IA (US); Ed Scura, Potomac, MD (US); Kurt Iver Kamrud, Apex, NC (US)

(73) Assignee: Harrisvaccines, Ames, IA (US)

( * ) Notice: Subject to any disclaimer, the term of this patent is extended or adjusted under 35 U.S.C. 154(b) by 41 days.

This patent is subject to a terminal disclaimer.

(21) Appl. No.: 13/277,066

(22) Filed: Oct. 19, 2011

(65) Prior Publication Data
US 2012/0108649 A1 May 3, 2012

Related U.S. Application Data

(60) Provisional application No. 61/407,297, filed on Oct. 27, 2010, provisional application No. 61/418,433, filed on Dec. 1, 2010, provisional application No. 61/449,940, filed on Mar. 7, 2011, provisional application No. 61/484,255, filed on May 10, 2011, provisional application No. 61/508,172, filed on Jul. 15, 2011, provisional application No. 61/525,332, filed on Aug. 19, 2011.

(51) Int. Cl.
| *A61K 31/70* | (2006.01) |
| *C07H 21/02* | (2006.01) |
| *C07H 21/04* | (2006.01) |
| *A61K 39/135* | (2006.01) |
| *C07K 14/005* | (2006.01) |
| *C12N 15/11* | (2006.01) |
| *A61K 39/145* | (2006.01) |
| *A61K 39/12* | (2006.01) |
| *C12N 15/86* | (2006.01) |
| *C12N 15/113* | (2010.01) |
| *C12Q 1/68* | (2006.01) |

(52) U.S. Cl.
CPC .............. *A61K 39/145* (2013.01); *A61K 39/135* (2013.01); *C12N 2710/18034* (2013.01); *C12N 2760/16134* (2013.01); *C12N 2760/16122* (2013.01); *C07K 14/005* (2013.01); *C12N 2320/32* (2013.01); *C12N 2770/10022* (2013.01); *C12N 2770/32134* (2013.01); *C12N 2720/00034* (2013.01); *C12N 2770/32122* (2013.01); *C12N 2720/00022* (2013.01); *C12N 15/111* (2013.01); *C12N 2310/14* (2013.01); *A61K 39/12* (2013.01); *C12N 2310/111* (2013.01); *C12N 15/86* (2013.01); *C12N 2770/36143* (2013.01); *C12N 2710/18022* (2013.01); *C12N 15/1131* (2013.01)
USPC ........ 514/44 A; 536/23.1; 536/24.1; 536/24.5

(58) Field of Classification Search
None
See application file for complete search history.

(56) References Cited

U.S. PATENT DOCUMENTS

| 4,220,584 | A | 9/1980 | Limjuco et al. |
| 4,285,931 | A | 8/1981 | Limjuco et al. |
| 4,692,412 | A | 9/1987 | Livingston |
| 5,759,829 | A | 6/1998 | Shewmaker |
| 5,792,462 | A | 8/1998 | Johnston et al. |
| 6,086,880 | A | 7/2000 | Sabara et al. |
| 6,156,558 | A | 12/2000 | Johnston et al. |
| 6,190,862 | B1 | 2/2001 | Kou |
| 6,326,193 | B1 | 12/2001 | Liu |
| 6,506,559 | B1 | 1/2003 | Fire et al. |
| 6,521,235 | B2 | 2/2003 | Johnston et al. |
| 6,531,135 | B1 | 3/2003 | Johnston et al. |
| 6,541,010 | B1 | 4/2003 | Johnston et al. |
| 6,573,099 | B2 | 6/2003 | Graham et al. |
| 6,908,616 | B2 | 6/2005 | Vlak |
| 7,045,335 | B2 | 5/2006 | Smith et al. |
| 7,291,588 | B2 | 11/2007 | Pizza et al. |
| 7,323,547 | B2 | 1/2008 | Kou |
| 7,410,637 | B2 | 8/2008 | Sayre |
| 7,442,381 | B2 | 10/2008 | Smith et al. |
| 7,537,768 | B2 | 5/2009 | Luke et al. |
| 7,538,095 | B2 | 5/2009 | Fire et al. |
| 7,560,438 | B2 | 7/2009 | Fire et al. |
| 7,622,254 | B2 | 11/2009 | Harris et al. |
| 7,622,633 | B2 | 11/2009 | Fire et al. |
| 7,651,998 | B1 | 1/2010 | MacDonald |

(Continued)

FOREIGN PATENT DOCUMENTS

| WO | WO03012052 A2 | 2/2003 |
| WO | WO2004085645 A1 | 10/2004 |

(Continued)

OTHER PUBLICATIONS

Shekhar et al., Mar Biotechnol, vol. 11:1-9, published online Oct. 22, 2008.*

(Continued)

*Primary Examiner* — Sean McGarry
(74) *Attorney, Agent, or Firm* — Patricia A. Sweeney

(57) ABSTRACT

Compositions and methods of protecting aquatic invertebrates from disease is shown. In one embodiment, dsRNA or antisense RNA to a nucleic acid molecule of the disease-causing microorganism is prepared and delivered to the animal. In another embodiment, a nucleic acid molecule of the disease-causing microorganism is delivered to the animal. In another embodiment, the RNA or nucleic acid molecule is delivered to the animal by replicon particle. In a further embodiment, the protective molecule is delivered to the digestive tract of the animal. Protection from disease is obtained.

15 Claims, 30 Drawing Sheets

(56) References Cited

U.S. PATENT DOCUMENTS

| | | |
|---|---|---|
| 7,749,506 B2 | 7/2010 | Van Hulten |
| 7,754,697 B2 | 7/2010 | Graham et al. |
| 7,862,829 B2 | 1/2011 | Johnston et al. |
| 2002/0114784 A1 | 8/2002 | Li et al. |
| 2003/0175783 A1 | 9/2003 | Waterhouse |
| 2003/0203868 A1 | 10/2003 | Bushman et al. |
| 2004/0081638 A1 | 4/2004 | Kyle |
| 2005/0080032 A1 | 4/2005 | Gross et al. |
| 2005/0095199 A1 | 5/2005 | Whyard |
| 2006/0120999 A1 | 6/2006 | Dhar |
| 2006/0178335 A1 | 8/2006 | Waterhouse et al. |
| 2007/0020652 A1 | 1/2007 | Alvarado et al. |
| 2007/0059808 A1 | 3/2007 | Klimpel |
| 2008/0107652 A1 | 5/2008 | Durvasula |
| 2008/0194504 A1 | 8/2008 | Kyle et al. |
| 2008/0213309 A1 | 9/2008 | Smith et al. |
| 2009/0098149 A1 | 4/2009 | Sayre |
| 2009/0165153 A1 | 6/2009 | Wang et al. |
| 2010/0324125 A1 | 12/2010 | Van Hulten |
| 2011/0064772 A1 | 3/2011 | Johnston |
| 2011/0158946 A1 | 6/2011 | Durvasula |
| 2012/0108649 A1 | 5/2012 | Loy et al. |

FOREIGN PATENT DOCUMENTS

| | | |
|---|---|---|
| WO | WO2005084312 A2 | 9/2005 |
| WO | WO2007084499 A2 | 7/2007 |
| WO | WO2007104782 A1 | 9/2007 |
| WO | WO2008085557 A2 | 7/2008 |
| WO | WO2012058073 A2 | 5/2012 |

OTHER PUBLICATIONS

U.S. Appl. No. 13/657,895 "Method of rapidly producing improved vaccines for animals" filed Oct. 23, 2012.

U.S. Appl. No. 13/657,898 "Methods and compositions to protect aquatic invertebrates from disease" filed Oct. 23, 2012.

Ning et al. (2009) "Oral delivery of DNA vaccine encoding VP28 against white spot syndrome virus in crayfish by attenuated *Salmonella typhimurium*" Vaccine 27:1127-1135.

European Patent Office, Invitation to pay additional fees, PCT/US2012/061433, Feb. 24, 2013.

European Patent Office, IWritten Optinion, PCT/US2012/061443, Feb. 21, 2013.

Vander Veen, Ryan "Alphavirus replicon vaccines" Animal Health Research Reviews, 13:No. 1, pp. 1-9 (Jun. 2012) XP009166113.

Martinez, et al, "Single-stranded antisense siRNAs guide target RNA cleavage in RNAi", Cell, vol. 110, 2002; pp. 563-574.

Balasuriya, et al, "Alphavirus replicon particles expressing the two major envelope proteins of equine arteritis virus induce high level protection against challenge with virulent virus in vaccinated horses", Vaccine, vol. 20, 2002; pp. 1609-1617.

Balasuriya, et al, "Expression of the Two Major Envelope Proteins of Equine Arteritis Virus as a Heterodimer is Necessary for Induction of Neutralizing Antibodies in Mice Immunized with Recombinant Venezuelan Equine Encephalitis Virus Replicon Particles", Journal of Virology, vol. 74, 2000, pp. 10623-10630.

Cheng, et al, "Characterization of an endogenous gene expressed in *Aedes aegypti* using an orally infectious recombinant Sindbis virus", Journal of Insect Science, vol. 1, 2001; pp. 1-7.

Davis, et al, "A Viral Vaccine Vector That Expresses Foreign Genes in Lymph Nodes and Protects against Mucosal Challenge" Journal of Virology, 1996, vol. 70: pp. 3781-3787.

Davis, et al, "In vitro synthesis of infectious venezuelan equine encephalitis virus RNA from a cDNA clone: analysis of a viable deletion mutant", Virology, vol. 171, 1989; pp. 189-204.

Escobedo-Bonilla, et al, "Standardized white spot syndrome virus (WSSV) inoculation procedures for intramuscular or oral routes", Disease of Aquric Organisms, vol. 68, 2006; pp. 181-188.

Harrington, et al, "Systemic, mucosal, and heterotypic immune induction in mice inoculated with Venezuelan equine encephalitis replicons expressing Norwalk virus-like particles", Journal of Virology, vol. 76, 2002; pp. 730-742.

Mogler "Replicon particle administration prior to challenge reduces PRRSV viremia" AASV Annual Meeting, Denver, CO, Mar. 10-12, 2012 Abstract.

Pushko, et al, "Individual and bivalent vaccines based on alphavirus replicons protect guinea pigs against infection with Lassa and Ebola viruses", Journal of Virology, vol. 75, 2001; pp. 11677-11685.

Pushko, et al, "Replicon-Helper Systems from Attenuated Venezuelan Equine Encephalitis Virus: Expression of Heterologous Genes in Vitro and Immunization against Heterologous Pathogens in Vivo", Virology, vol. 239, 1997, pp. 389-401.

Kamrud, et al, "RNA Particle FMDV Vaccine Proof of Concept Study in Cattle", 42nd Annual American Association of Swine Veterinarians, Phoenix, AZ, Mar. 5-8, 2011.

Zhou "Four major Envelope Proteins of White Spot Syndrome Virus bind to form a complex" Journal of virology p. 4709-4712 (2009).

Sepp, et al, "Giardiavirus-Resistant Giardia lamblia Lacks a Virus Receptor on the Cell Membrane Surface", Journal of Virology, vol. 68, 1994; pp. 1426-1431.

Mogler, et al, "RNA particle administration prior to challenge reduces PRRSV viremia", AASV Annual Meeting, Denver, CO, Mar. 10-12, 2012; PowerPoint.

Shekar, et al, "Application of Nucleic-acid-based Therapeutics for Viral Infections in Shrimp Aquaculture", Marine Biotechnology, Springer-Verlag, NE, vol. 11(1), 2008; pp. 1-9.

Mogler, et al, "Replicon particle administration prior to challenge reduces PRRSV vermia", International PRRS Symposium, Chicago IL, Dec. 2-3, 2011; Poster and Abstract.

Sarathi, et al, "Efficacy of bacterially expressed dsRNA specific to different structural genes of white spot syndrome virus (WSSV) in protection of shrimp from WSSV infection" Journal of Fish Diseases 2010, 33, 603-607.

Walker et al. "Emerging viral diseases of fish and shrimp" Vet Res (2010) 41:51.

Thompson et al. "Mucosal and systemic adjuvant activity of alphavirus replicon particles" PNAS vol. 103, No. 10 pp. 3722-3727 (2006).

Thompson et al. "Nonmucosal Alphavirus Vaccination Stimulates a Mucosal Inductive Environment in the Peripheral Draining Lymph Node" Journal of Immunology 181:574-585 (2008).

Hammond et al. "An RNA-directed nuclease mediates post-transcriptional gene silencing in *Drosophila* cells" Nature, vol. 404, Letters, Mar. 16, 2000.

Andrade, et al, "Real-time transcription polymerase chain reaction assay using TaqMan probe for detection and quantification of infectious myonecrosis virus (IMNV)", Aquaculture, vol. 264, 2007; pp. 9-15.

Fire, et al, "Potent and specific genetic interference by double-stranded RNA in *Caenorhabditis elegans*", Nature, vol. 391, 1998; pp. 806-811.

Hasson, et al, "Taura syndrome in *Penaeus vannamei*: demonstration of viral etiology", Disease of Aquatic Organisms, vol. 23, 1995; pp. 115-126.

Kronke, et al, "Alternative Approaches for Efficient Inhibition of Hepatitis C Virus RNA Replication by Small Interfering RNAs", Journal of Virology, vol. 78, 2004; pp. 3436-3446.

Labreuche, et al, "Non-specific activation of antiviral immunity and iinduction of RNA interference may engage the same pathway in the Pacific white leg shrimp *Litopenaeus vannamei*", Dev Comp. Immunol., 2010.

Lightner, et al, "The Penaeid Shrimp Viruses TSV, IHHNV, WSSV, and YHV: Current Status in Americas, Available Diagnostic Methods and Management Strategies", Journal of Applied Aquaculture, vol. 9, 1999; pp. 27-52.

Timmons, et al "Ingestion of bacterially expressed dsRNAs can produce specific and potent genetic interference in *Caenorhabditis elegans*" Gene 263: (2001) 103-112.

Tang et al., 2008 Infectious myonecrosis virus has a totivirus-like 120-subunit capsid, but with fiber complexes at the fivefold axes. PNAS 105:17526-17531.

Prickett et al. (2008) "Detection of Porcine reproductive and respiratory syndrome virus infection in porcine oral fluid samples: a longitudinal study under experimental conditions" J. Vet Diagn. Invest. 20:156.

(56) References Cited

OTHER PUBLICATIONS

Kamrud et al (2007) "Analysis of Venezuelan Equine Equine Encephalitis Replicon Particles Packaged in Different Coats" PLoS One 3(7) e2709 doi:10.1371/journal.pone.0002709.
Paradis et al. (2007) Can Vet J. 48(1):57-62.
Stentiford et al. "Disease will limit future food supply from the global crustacean fishery and aquaculture sectors" Journal of Invert. Path. 110:141-157 (2012).
Robalino, et al."Induction of Antiviral Immunity by Double-Stranded RNA in a Marine Invertebrate." Journal of Virology 78 (2004): 10442-10448.
Robalino, et al. "Insights into the immune transcriptome of the shrimp Litopenaeus vannamei: tissue-specific expression profiles and transcriptomic responses to immune challenge." Physiol Genomics 29 (2007): 44-56.
Robalino, et al."Inactivation of White Spot Syndrome Virus (WSSV) by normal rabbit serum: Implications for the role of the envelope protein VP28 in WSSV infection of shrimp." Virus Research 118 (2006): 55-61.
Robalino, et al. "Double-stranded RNA and antiviral immunity in marine shrimp: Inducible host mechanisms and evidence for the evolution of viral counter-responses." Developmental and Comparative Immunology 31 (2007): 539-547.
Kamrud et al. "In Vitro and In Vivo Characterization of MicroRNA-Targeted Alphavirus Replicon and Helper RNAs" Journal of Virology pp. 7713-7725 (2010).
Kurtz "Specific memory with innate immune systems" Trends in Immunology vol. 26, No. 4 Apr. 2006.
Konopka et al. "Acute Infection with Venezuelan Equine Encephalitis Virus Replicon Particles Catalyzes a Systemic Antiviral State and Protects from Lethal Virus Challenge" Jounral of Virology vol. 83 No. 23 pp. 12434-12442 (2009).
Lang "RNA viruses in the sea" FEMS Microbiol. REv. 33:295-323 (2009).
Mejia-Ruiz et al. "Double-stranded RNA against white spot syndrome virus (WSSV) vp28 3 or vp26 reduced susceptibility of Litopenaeus vannamei to WSSV, and 4 survivors exhibited decreased susceptibility in subsequent re-infections" (2011) Journal of Invert. Path. doi:10/1016/j.jip.2011.02.002.
Saksmerprome et al. "A novel and inexpensive application of RNAi technology to protect shrimp from viral disease" Journal of Vir. Methods 162:213-217 (2009).
Davis et al. "Vaccination of macaques against pathogenic Simian immunodeficiency virus with Venezuelan equine encephalitis virus replicon particles" 2000 Journal of Virology 74:371-378.
Carroll et al. "Alphavirus replicon-based adjuvants enhance the immunogenicity and effectiveness of Fluzone® in rhesus macaques" Vaccine 29 (2011) 931-940.
Saikh et al. "Toll-Like Receptor and Cytokine Expression Patterns of CD56+ T Cells Are Similar to Natural Killer Cells in Response to Infection with Venezuelan Equine Encephalitis Virus Replicons" JID 2003:188 (Nov. 2003).
Tonkin et al. "Alphavirus replicon-based enhancement of mucosal and systemic immunity is linked to the innate response generated by primary immunization" Vaccine 28:3238-3246 (2010).
Kowalski et al. "Evaluation of neurovirulence and biodistribution of Venezuelan equine encephalitis replicon particles expressing herpes simplex virus type 2 glycoprotein D" Vaccine 25:2296-2305 (2007).
Witteveldt et al."Protection of Penaeus monodon against white spot syndrome virus using WSSV subunit vaccine" Fish & Shellfish Immunology 16:571-579 (2004).
Route et al DNA vaccines encoding viral envelope proteins confer protective immunity against WSSV in black tiger shrimp: Vaccine 25:2778-2786 (2008).
Fu et al. "Oral vaccination with envelope protein VP28 against white spot syndrome virus in Procambarus clarkii using Bacillus subtilis as delivery vehicles" The Society for Applied Microbiology, Letters in Appl. Micro. I46:581-586 (2008).
Loy, J. Dustin., L.C. Bartholomay, and D.L. Harris. 2011. Evaluation of Double Stranded RNA for the Prevention of Infectious Myonecrosis Virus (IMNV) in Litopenaeus vannamei. Iowa State University Animal Industry Report ASL-R-2595.
Veits, et al, "Newcastle disease virus expressing H5 hemagglutinin gene protects chickens against Newcastle disease and avian influenza", Proceedings of the National Academy of Sciences of the USA, National Academy of Science, Washington DC; vol. 103(21), May 23, 2006; pp. 8197-8202.
Kodihalli, et al, "Strategies for inducing protection against avian influenza A virus subtypes with DNA vaccines", Vaccne, vol. 18(23), May 1, 2000; pp. 2592-2599.
Adelman, et al, "Sindbis virus-induced silencing of dengue viruses in mosquitos", Insect Molecular Biology, vol. 10 (3), Jun. 1, 2001; pp. 265-273.
Garcia, et al, "Nairovirus RNA Sequences Expressed by a Semliki Forest Virus Replicon Induce RNA Interference in Tick Cells", Journal of Virology, vol. 79(14), Jun. 30, 2005; pp. 8942-8947.
Robalino, et al, "Double-Stranded RNA Induces Sequence-Specific Antiviral Silencing in Addition to Nonspecific Immunity in a Marine Shrimp: Convergence of RNA interference and Innate Immunity in the Invertebrate Antiviral Response?", Journal of Virology, vol. 79(1), Oct. 13, 2005; pp. 13561-13571.
Von Herrath, et al, "Immune responsiveness, tolerance and dsRNA: implications for traditional paradigms", Trends in Immunology, vol. 24(6), Jun. 1, 2003, pp. 289-292.
Bosworth, et al, "Replicon particle vaccine protects swine against influenza", Comparative Immunology, Microbiology and Infectious Diseases, vol. 33, 2010; pp. E99-E103.
Vander Veen, et al, "Rapid Development of an Efficacious Swine Vaccine for Novel H1N1", PLOS Currents Influenza, Nov. 2009; 2RRN1123; Available from URL: http://www.ncbi.nlm.nih.gov/rm/articlerender.fcgi?acc=RRN1123.
Rapp-Gabrielson, et al, "Updating swine influenza vaccines", AASV 39th Annual Meeting Proceedings, 2008; pp. 261-264.
Henry, S., "Swine influenza virus—efforts to define and implement regional immunization", AASV Proceedings, 2009; pp. 475-478.
www.avma.org/issues/policy/autogenous_biologics.asp "Guidelines for Use of Autogenous Biologics" (Oversigh: COBTA; EB approved—1993; reaffirmed Nov. 1997; reaffirmed Apr. 2001; revised Mar. 2006, Nov. 2009).
Katz, et al, "Serum Cross-Reactive Antibody Response to a Novel Influenza A (H1N1) Virus After Vaccination with Seasonal Influenza Vaccine", Morbid. Mortal. Weekly Resp., vol. 58(19), 2009; pp. 521-524.
Nibert, et al, "'2A-like' and 'shifty heptamer' motifs in penaeid shrimp infectious myonecrosis virus, a monosegmented double-stranded RNA virus", Journal of General Virology, vol. 88, 2007; pp. 1315-1318.
Poulos, et al, GenBank accession No. AY570982, 2006.
Senapin, et al, GenBank acceession No. EF061744, 2007.
McClennon, et al, "The Economic, Environmental and Technical Implications on the Developments of Latin American Shrimp Farming", Masters of Arts and Law and Diplomacy Thesis, 2004—http://fletcher.tufts.edu.
Poulos, et al, GenBank No. AAT67231.1 2006.
Senapin, et al, GenBank ABN05325.1 2007.
Zhang, et al, "Enhancement of mucosal immune response against the M2eHBc+ antigen in mice with the fusion expression products of LTB and M2eHBc+ through mucosal immunization route", Vet. Rex. Commun., DOI 10/1007/s11259-009-9222-7(2009).
Potter, et al, "Determinants of Immunity to Influenza Infection in Man", Br Med Bull, vol. 35, 1979, pp. 69-75.
Erdman, et al, "Replicon particle co-expression of PRRSV GP5 and M proteins", Proc CRWAD, 2006, abstract and poster.
Schultz-Cherry, et al, "Influenza virus (A/HK/156/97) hemagglutinin expressed by an alphavirus replicon system protects chickens against lethal infection with Hong Kong-origin H5N1 viruses", Virology, vol. 278(1), Dec. 5, 2000; pp. 55-59; PubMed PMID: 11112481.
Erdman, et al, "Alphavirus Replicon Paricle Vaccines Developed for Use in Humans Induce High Levels of Antibodies to Influenza Virus Hemagglutinin in Swine: Proof of Concept", Vaccine, vol. 28, 2010; pp. 594-596.

(56) References Cited

OTHER PUBLICATIONS

Hooper, et al, "Molecular Smallpox Vaccine Delivered by Alphavirus Replicons Ellicits Protective Immunity in Mice and Non-Human Primates", Vaccine, Vaccine 28 (2010) 494-511.

Kamrud, et al, "Alphavirus replicon approach to promoterless analysis of IRES elements", Virology, vol. 360(2), Apr. 10, 2007; pp. 367-387; PubMed PMID: 17156813; PubMed Central PMCID: PMC1885372.

Senapin, et al, "Outbreaks of infectious myonecrosis virus (IMNV) in Indonesia confirmed by genome sequencing and use of an alternative RT-PCR detection method", Autoculture, vol. 266; pp. 32-38 (2007).

Van Hulten et al. GenBank AF369029.2 GI: 124303516 (2005).

Zhang (2010) Chitosan/double-stranded RNA nanoparticle-mediated RNA interference to silence chitin synthase genes through larval feeding in the African malaria mosquito (*Anopheles gambiae*) Insect Molecular Biology 19(5) 683-693.

Smith, et al, "Mapping the Antigenic and Genetic Evolution of Influenza Virus", Sci, vol. 305, 2004; pp. 371-376.

Vincent, et al, "Characterization of a newly emerged genetic cluster of H1N1 and H1N2 swine influenza virus in the United States", Virus Genes, 2009; 39.

Gramer et al, "Serologic cross-reactions between reference strains and field isolates representing different genetic clusters of H1N1 and H3N2 swine influenza virus", American Association of Swine Veterinarians, 2008; pp. 99-101.

Vincent, et al., "Characterization of a an influenza A virus isolated from pigs during an outbreak of respiratory disease in swine and people during a county fair in the United States", Vet Micro, vol. 137; 2009; pp. 51-59.

Vincent, et al, "Swine Influenza Viruses: A North American Perspective.", Advances in Virus Research, Burlington Academic Press, 2008; vol. 72 pp. 127-154.

Harris, et al, "Surveillance and vaccine strain selection for control of swine influenza", 2010 AASV Annual Meeting Implementing Knowledge; American Association of Swine Veterinarians.

Morse et al. "An alphavirus vector overcomes the presence of neutralizing antibodies and elevated numbers of Tregs to induce immune responses in humans with advanced cancer" The Journal of Clinical Investigation vol. 120, No. 9, pp. 3234-3241 (Sep. 2010).

Mogler, et al, "Replicon particle Porcine Reproductive and Respiratory Syndrome Virus Vaccine Provides Partial Protection from Challenge", A.S. Leaflet R2382, Iowa State University Animal Industry Report 2009, Department of Animal Science and VDPAM.

Sarathi et al. "Oral administration of bacterially expressed VPO28dsRNA to protect *Penaeus monodon* from White Spot Syndrome Virus" Mar. Biotechnol. (2008) 10:242-249.

Moraes, et al, "Early protection against homologous challenge after a single dose of replication-defective human adenovirus type 5 expressing capsid proteins of foot-and-mouth disease virus (FMDV) strain A24", Vaccine, vol. 20, 2002; pp. 1631-1639.

9 C.F.R. 107.1 regarding Veterinary Client Patient relationship arrangements (VCPR), as amended Dec. 26, 1991.

EPO Search Report for PCT/US2011/056950; Jun. 6, 2012.

EPO Search Report for PCT/US201111/056945; Feb. 29, 2012.

Bartholomay, et al, "Nucleic-acid based antivirals: Augmenting RNA interference to "vaccinate" *Litopenaeus vannamei*", J. Invertebr. Pathol., (Mar. 16, 2012, Epub ahead of print PMID: 22429833) Journal of Invertebrate pathology 110 (2012 161-266.

Loy, et al, "dsRNA provides sequence-dependent protection against infectious myonecrosis virus in *Litopenaeus vannamei*", J. Gen. Virol., Apr. 2012, 93(pt4); Epub Jan. 4, 2012; pp. 880-888.

Nelson et al. "Venezuelan equine encephalitis replicon immunization overcomes intrinsic tolerance and elicits effective anti-tumor immunity to the 'self' tumor-associated antigen, neu in rat mammary tumor model" Breast Cancer Research and Treatment 82:169-193 (2002).

Osada et al. "Co-delivery of antigen and IL-12 by Venezuelan equine encephalitis virus replicon particles enhances antigen-specific immune responses and antitumor effects" Cancer Immunol. Immunother DO1 10.1007/s00262-012-1248-7, Published online Apr. 10, 2012.

Liu et al. "Antiviral immunity in crustaceans" Fish and Shellfish Immunology, Academic Press, London, GB, vol. 27 No. 2, pp. 79-88, Aug. 1, 2009.

Poulos, et al, "Purification and characterization of infectious myonecrosis virus of penaeid shrimp", Journal of General Virology, vol. 87, 2006; pp. 987-996.

Loy and Loy "Alphavirus Replicon Particles potential method for WSSV vaccination of white shrimp" Global Aquaculture Advocate May/Jun. 2011 p. 71-7.

Loy, J. Dustin., D.S. Loy, M.A. Mogler, D.L. Harris, and L.C. Bartholomay. 2011. "Evaluation of in vitro synthesized double stranded RNA for the prevention of Infectious Myonecrosis Virus in *Litopenaeus vannamei*. Aquaculture America. Baton Rouge, LA."

Loy et al. "Direct delivery of VP19 double-stranded RNA into the gut of *Litopeneus vannamei* shows protection against white spot disease" Aquaculture America 2012, Abstract.

\* cited by examiner

Figure 19A

SEQUENCE LISTING

```
<160> NUMBER OF SEQ ID NOS: 85

<210> SEQ ID NO 1
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
agaaagtttg tttcgtagag cgagaaaaac agaatccact tatggctata acgaactag      60 ccgttaaagt tggagagaag cctaaataca catcgacgaa aaccggagct gaccacattc    120
caagctggac tgtattggtt gagttcgcag gttttagcga agcagcgaca tgtgacacag    180
ttaaaaacgc aaaaatgatt gctgcttaca aattagttaa aagattttgt aaatgggacc    240
caacctacat tgaaatttct gattgtatgc tgccacctcc agaccttaca tcgtgcgggg    300
acgttgagag taatcctgga cctatcatac atagcgttgc atttgcaaga actggttcag    360
tatggacacc tgccaccttt a                                              381

<210> SEQ ID NO 2
<211> LENGTH: 283
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 2

| aaaaccggag ctgaccacat tccaagctgg actgtattgg ttgagttcgc aggttttagc | 60 |
| gaagcagcga catgtgacac agttaaaaac gcaaaaatga ttgctgctta caaattagtt | 120 |
| aaaagatttt gtaaatggga cccaacctac attgaaattt ctgattgtat gctgccacct | 180 |
| ccagacctta catcgtgcgg ggacgttgag agtaatcctg gacctatcat acatagcgtt | 240 |
| gcatttgcaa gaactggttc agtatggaca cctgccacct tta | 283 |

<210> SEQ ID NO 3
<211> LENGTH: 282
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

| agaaagtttg tttcgtagag cgagaaaaac agaatccact tatggctata acgaactag | 60 |
| ccgttaaagt tggagagaag cctaaataca catcgacgaa aaccggagct gaccacattc | 120 |
| caagctggac tgtattggtt gagttcgcag gttttagcga agcagcgaca tgtgacacag | 180 |
| ttaaaaacgc aaaaatgatt gctgcttaca aattagttaa aagattttgt aaatgggacc | 240 |
| caacctacat tgaaatttct gattgtatgc tgccacctcc ag | 282 |

<210> SEQ ID NO 4
<211> LENGTH: 1042
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

| aatttgggtg gttgggacac atggccagtt atatgatggg actccttcta acaatgaata | 60 |
| tatcatcagt gtttaacgtt tggtattcaa caagacgtat ttcaacaaag gcatgggaca | 120 |
| cagcatatga tagtaacatc caagcatatc aggacatgca ttatcaaatg ttttcgtgga | 180 |
| gttcaatgca aggtagtatt gcaccagcaa tggtggacga aattcttcat aacctttgtg | 240 |
| gccaaatgtt tgggttcagc ttaccattga dacaagtctt atttaacgca ttgccaatca | 300 |
| cttttttcatc gtttggaagt tggatgtcgc ctagagtttc tgatggtttc caaactgtaa | 360 |
| ggtattatga tataggtcca ccagtcatta acccgaaacg tgatggggaa gtaccagtaa | 420 |
| gtatgattga cgcatggacc tataaattta cagaaaaatt gccaaaaagt tttttgccat | 480 |
| ggccaatgcc agaaggaaag gacagtacaa tgggatatga tccggaaaaa gaaccagctc | 540 |
| taattgataa ttcaaatgag acaggcaatg tattcagacc atttatggca agaaatggca | 600 |
| acaattctaa ttatttgcca accaactaca caattgacgt atcacagaat ggtcatgacg | 660 |
| agagttgtat taatgttgac cttttttaaca atgttgcagg agtaacacta acaaattatg | 720 |
| atggaaccgc aacaaacgca gacgtcgtac aacaggatc atacattaag cagagagcaa | 780 |
| tgcctatcaa tgcaaatgcg gtacgaccaa ctgaaacact cgacgctgcc aaccatacga | 840 |
| aacctttgtc tattggagga ggaagactcg tatatttggg tggaacaatt gcaaatacaa | 900 |
| ccaatgtggt aaacgcaatg cagaggaaac aaaggctttc aaaaccagca ttcaagtggg | 960 |
| cacatgctca gagacaacgt gtatatgaca gcagtcgtcc agggatggac gcaatcacaa | 1020 |

```
agttgtgtgc acgaaagtcg gg                                         1042
```

<210> SEQ ID NO 5
<211> LENGTH: 875
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (64)..(64)
<223> OTHER INFORMATION: a, c, t, g, unknown or other

<400> SEQUENCE: 5

```
cttaatatag caacgtcgtc tccgcgtaac gagatttggg agattgggtc gtatccaata    60
attnccaata acattattta ttgcgatctt tgtaattata gcgttccaca tattacccaa   120
caaactcgtt attctcactc ctgatggtac tccacctttg actttatat tttcaaattt    180
tgtattttta atatttccag acaaataact tttatcatat gcattaacaa tcttattgac   240
tagcaattgt gtctgatagt aataattctt aggtacttga ctaactacaa tttctccaac   300
tcttctcacc attgtcttaa cttcaaaagt tgttggctga tgatcaaatg atgcatagtc   360
aaatggtaat ccaaagtatc cagcttgtag tttctcaatc atttcaattt ctctctgatg   420
ctgttgatct ggttttcat caagcgtcac tccaaagtgt tccttaaaac catgaccata    480
taggaaaagc atataagatt catgaatata tgcttcgatg ttagatgcga cagcaagtct   540
taatttactc atttcgtttt taataaagac acgtgaatgt aactttccat cccaagcata   600
aacaatgttg gccaattctt gcggtgtata aatttgtaac agcatatttt tccttgcttt   660
aaatttccca ttttctccat cttttgtcca atgcactttc ccaatacttg aacttccact   720
tgttaaccac attccttcct ttatgtaatc atcaaaacta ataaattcat gtcctttgta   780
ccatgtcatt acttctttgc atgtttttgt aaacaaatca ttccaattat ctctatctat   840
accatgttca ttaccttcag atgcgagtga gttga                              875
```

<210> SEQ ID NO 6
<211> LENGTH: 719
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
tgagcaaggg cgaggagctg ttcaccgggg tggtgcccat cctggtcgag ctggacggcg    60
acgtaaacgg ccacaagttc agcgtgtccg gcgagggcga gggcgatgcc acctacggca   120
agctgaccct gaagttcatc tgcaccaccg gcaagctgcc cgtgccctgg cccaccctcg   180
tgaccaccct gacctacggc gtgcagtgct tcagccgcta ccccgaccac atgaagcagc   240
acgacttctt caagtccgcc atgcccgaag gctacgtcca ggagcgcacc atcttcttca   300
aggacgacgg caactacaag acccgcgccg aggtgaagtt cgagggcgac accctggtga   360
accgcatcga gctgaagggc atcgacttca aggaggacgg caacatcctg ggcacaagc    420
tggagtacaa ctacaacagc cacaacgtct atatcatggc cgacaagcag aagaacggca   480
tcaaggtgaa cttcaagatc cgccacaaca tcgaggacgg cagcgtgcag ctcgccgacc   540
actaccagca gaacaccccc atcggcgacg gccccgtgct gctgcccgac aaccactacc   600
```

```
tgagcaccca gtccgccctg agcaaagacc ccaacgagaa gcgcgatcac atggtcctgc    660
tggagttcgt gaccgccgcc gggatcactc tcggcatgga cgagctgtac aagtaatct     719
```

<210> SEQ ID NO 7
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
taatacgact cactataggg agaatggtga gcaagggcga ggagctgt               48
```

<210> SEQ ID NO 8
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
taatacgact cactataggg agattacttg tacagctcgt ccatgccg               48
```

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
agaaagtttg tttcgtagag cgaga                                        25
```

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
aaaggtggca ggtgtccata ctga                                         24
```

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
taatacgact cactataggg agaagaaagt ttgtttcgta gagc                   44
```

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
taatacgact cactataggg agaaaaggtg gcaggtgtcc atac                         44
```

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

```
aatttgggtg gttgggacac atgg                                              24
```

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

```
cccgactttc gtgcacacaa cttt                                              24
```

<210> SEQ ID NO 15
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

```
taatacgact cactataggg agaaatttgg gtggttggga caca                        44
```

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

```
taatacgact cactataggg agacccgact ttcgtgcaca c                           41
```

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

```
tcaactcact cgcagctgaa ggta                                              24
```

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

```
aatatagcaa cgtcgtctcc gcgt                                            24
```

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

```
taatacgact cactataggg tcaactcact cgcagctgaa g                          41
```

<210> SEQ ID NO 20
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

```
taatacgact cactataggg aatatagcaa cgtcgtctcc g                          41
```

<210> SEQ ID NO 21
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

```
taatacgact cactataggg agacgaagct tggccaccac gact                       44
```

<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

```
taatacgact cactataggg agacggagct cctgcctcct cttggggtaa                 50
```

<210> SEQ ID NO 23
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

```
cgggatccat tgaaggccgc gccatggatc tttctttcac tct                        43
```

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

```
cggagctctt actcggtctc agtgccaga                                        29
```

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gagaggcgcg ccatggatct ttcttt                                            26

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tctcttaatt aactactcgg tctcagt                                           27

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctaaggcgcg cctaaaggtg gcagg                                             25

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cgcgttaatt aaagaaagtt tgtttcg                                           27

<210> SEQ ID NO 29
<211> LENGTH: 615
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
atggatcttt ctttcactct ttcggtcgtg tcggccatcc tcgccatcac tgctgtgatt        60
gctgtattta ttgtgatttt taggtatcac aacactgtga ccaagaccat cgagacccac       120
acagacaata tcgagacaaa catggatgaa aacctccgca ttcctgtgac tgctgaggtt       180
ggatcaggct acttcaagat gactgatgtg tcctttgaca cgacaccttt gggcaaaatc       240
aagatccgca atggaaagtc tgatgcacag atgaaggaag aagatgcgga tcttgtcatc       300
actcccgtgg agggtcgagc actcgaagtg actgtggggc agaatctcac ctttgaggga       360
acattcaagg tgtggaacaa cacatcaaga aagatcaaca tcactggtat gcagatggtg       420
ccaaagatta acccatcaaa ggcctttgtc ggtagctcca cacctcctc cttcaccccc       480

```
gtctctattg atgaggatga agttggcacc tttgtgtgtg gtaccacctt tggcgcacca    540
attgcagcta ccgccggtgg aaatcttttc gacatgtacg tgcacgtcac ctactctggc    600
actgagaccg agtaa                                                      615

<210> SEQ ID NO 30
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
atggccacca cgactaacac tcttcctttc ggcaggaccg agcccaggc cgctggccct     60 tcttacacca tggaagatct tgaaggctcc atgtctatgg ctcgcatggg tctcttttg    120 atcgttgcta tctcaattgg tatcctcgtc ctggccgtca tgaatgtatg gatgggacca   180
aagaaggaca gcgattctga cactgataag gacaccgatg atgatgacga cactgccaac   240
gataacgatg atgaggacaa atataagaac aggaccaggg atatgatgct tctggctggg   300
tccgctcttc tgttcctcgt ttccgccgcc accgttttta tgtcttaccc caagaggagg   360
cagtga                                                              366

<210> SEQ ID NO 31
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
tcactgcctc ctcttggggt aagacataaa aacggtggcg gcggaaacga ggaacagaag    60
agcggaccca gccagaagca tcatatccct ggtcctgttc ttatatttgt cctcatcatc   120
gttatcgttg gcagtgtcgt catcatcatc ggtgtcctta tcagtgtcag aatcgctgtc   180
cttctttggt cccatccata cattcatgac ggccaggacg aggataccaa ttgagatagc   240
aacgatcaaa aagagaccca tgcgagccat agacatggag ccttcaagat cttccatggt   300
gtaagaaggg ccagcggcct gggctccggt cctgccgaaa ggaagagtgt tagtcgtggt   360
ggccat                                                              366

<210> SEQ ID NO 32
<211> LENGTH: 741
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
atggccacca cgactaacac tcttcctttc ggcaggaccg agcccaggc cgctggccct     60 tcttacacca tggaagatct tgaaggctcc atgtctatgg ctcgcatggg tctcttttg    120 atcgttgcta tctcaattgg tatcctcgtc ctggccgtca tgaatgtatg gatgggacca   180
aagaaggaca gcgattctga cactgataag gacaccgatg atgatgacga cactgccaac   240
gataacgatg atgaggacaa atataagaac aggaccaggg atatgatgct tctggctggg   300
tccgctcttc tgttcctcgt ttccgccgcc accgttttta tgtcttaccc caagaggagg   360
```

```
cagtgattca agagatcact gcctcctctt ggggtaagac ataaaaacgg tggcggcgga    420
aacgaggaac agaagagcgg acccagccag aagcatcata tccctggtcc tgttcttata    480
tttgtcctca tcatcgttat cgttggcagt gtcgtcatca tcatcggtgt ccttatcagt    540
gtcagaatcg ctgtccttct ttggtccat ccatacattc atgacggcca ggacgaggat     600
accaattgag atagcaacga tcaaaaagag acccatgcga gccatagaca tggagccttc    660
aagatcttcc atggtgtaag aagggccagc ggcctgggct ccggtcctgc cgaaaggaag    720
agtgttagtc gtggtggcca t                                              741

<210> SEQ ID NO 33
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
taaaggtggc aggtgtccat actgaaccag ttcttgcaaa tgcaacgcta tgtatgatag     60
gtccaggatt actctcaacg tccccgcacg atgtaaggtc tggaggtggc agcatacaat    120
cagaaatttc aatgtaggtt gggtcccatt tacaaaatct tttaactaat ttgtaagcag    180
caatcatttt tgcgttttta actgtgtcac atgtcgctgc ttcgctaaaa cctgcgaact    240
caaccaatac agtccagctt ggaatgtggt cagctccggt tttcgtcgat gtgtatttag    300
gcttctctcc aactttaacg gctagttcgt ttatagccat aagtggattc tgttttctc    360 gctctacgaa acaaactttc t                                              381

<210> SEQ ID NO 34
<211> LENGTH: 678
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
atggatagca ctgagaacgt catcaagccc ttcatgcgct tcaaggtgca catggagggc     60
tccgtgaacg gccacgagtt cgagatcgag ggcgagggcg agggcaagcc ctacgagggc    120
acccagaccg ccaagctgca ggtgaccaag gcggccccc tgcccttcgc ctgggacatc     180 ctgtccccc agttccagta cggctccaag gtgtacgtga agcaccccgc cgacatcccc    240
gactacaaga agctgtcctt ccccgagggc ttcaagtggg agcgcgtgat gaacttcgag    300
gacggcggcg tggtgaccgt gacccaggac tcctccctgc aggacggcac cttcatctac    360
cacgtgaagt tcatcggcgt gaacttcccc tccgacggcc ccgtaatgca agaagaagact   420 ctgggctggg agcctccac cgagcgcctg taccccgcg acggcgtgct gaagggcgag     480
atccacaagg cgctgaagct gaagggcggc ggccactacc tggtggagtt caagtcaatc    540
tacatggcca agaagcccgt gaagctgccc ggctactact acgtggactc caagctggac    600
atcacctccc acaacgagga ctacaccgtg gtggagcagt acgagcgcgc cgaggcccgc    660
caccacctgt tccagtag                                                  678

<210> SEQ ID NO 35
<211> LENGTH: 381
<212> TYPE: RNA
```

<213> ORGANISM: Artificial Sequence
<220> FEATURE:
<223> OTHER INFORMATION: Description of Artificial Sequence: Synthetic
      polynucleotide

<400> SEQUENCE: 35

```
agaaaguuug uuucguagag cgagaaaaac agaauccacu uauggcuaua aacgaacuag      60
ccguuaaagu uggagagaag ccuaaauaca caucgacgaa aaccggagcu gaccacauuc     120
caagcuggac uguauugguu gaguucgcag guuuuagcga agcagcgaca ugugacacag     180
uuaaaaacgc aaaaaugauu gcugcuuaca aauuaguuaa aagauuuugu aaaugggacc     240
caaccuacau ugaaauuucu gauuguaugc ugccaccucc agaccuuaca ucgugcgggg     300
acguugagag uaauccugga ccaucauac auagcguugc auuugcaaga acugguucag     360
uauggacacc ugccaccuuu a                                              381
```

<210> SEQ ID NO 36
<211> LENGTH: 381
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 36

```
uaaaggugge aggguccauu acugaaccag uucuugcaaa ugcaacgcua uguaugauag      60
guccaggauu acucucaacg uccccgcacg auguaagguc uggaggluggc agcauacaau    120 cagaaauuuc aauguagguu ggglucccauu uacaaaaucu uuuaacuaau uuguaagcag    180
caaucauuuu ugcguuuuua acuguguucac augucgcugc uucgcuaaaa ccugcgaacu    240
caaccaauac aguccagcuu ggaauguggu cagcuccggu uuucgucgau uguauuuag     300 gcuucucucc aacuuuaacg gcuaguucgu uuauagccau aaguggauuc uguuuuucuc    360
gcucuacgaa acaaacuuuc u                                              381
```

<210> SEQ ID NO 37
<211> LENGTH: 283
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 37

```
aaaaccggag cugaccacau uccaagcugg acuguauugg uugaguucgc agguuuuagc      60
gaagcagcga caugugacac aguuaaaaac gcaaaaauga uugcugcuua caaauuaguu    120
aaaagauuuu guaaauggga cccaaccuac auugaaauuu cugauuguau gcugccaccu    180
ccagaccuua caucgugcgg ggacguugag aguaauccug gaccaucau acauagcguu    240 gcauuugcaa gaacugguuc aguauggaca ccugccaccu uua                      283
```

<210> SEQ ID NO 38
<211> LENGTH: 381
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 38

```
uaaaggugge aggguccauu acugaaccag uucuugcaaa ugcaacgcua uguaugauag      60
```

```
guccaggauu acucucaacg uccccgcacg auguaagguc uggaggaggc agcauacaau    120
cagaaauuuc aauguagguu ggguccccauu ucaaaaucu uuuaacuaau uguaagcag     180 caaucauuuu ugcguuuuua acugugucac augucgcugc uucgcuaaaa ccugcgaacu    240
caaccaauac aguccagcuu ggaaugugg cagccccggu uuucgucgau uguauuuag      300 gcuucucucc aacuuuaacg gcuaguucgu uuauagccau aaguggauuc uguuuuucuc    360
gcucuacgaa acaaacuuuc u                                               381

<210> SEQ ID NO 39
<211> LENGTH: 282
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 39
agaaaguuug uuucguagag cgagaaaaac agaauccacu uauggcuaua aacgaacuag     60
ccguuaaagu uggagagaag ccuaaauaca caucgacgaa aaccggagcu gaccacauuc    120
caagcuggac uguauugguu gaguucgcag guuuuagcga agcagcgaca ugugacacag    180
uuaaaaacgc aaaaaugauu gcugcuuaca aauuaguuaa agauuuugu aaaugggacc    240 caaccuacau ugaaauuucu gauguaugc ugccaccucc ag                         282

<210> SEQ ID NO 40
<211> LENGTH: 282
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 40
cuggaggugg cagcauacaa ucagaaauuu caauguaggu uggguccccau uuacaaaauc     60 uuuuaacuaa uuuguaagca gcaaucauuu uugcguuuuu aacugugca caugucgcug    120 cuucgcuaaa accugcgaac ucaaccaaua caguccagcu uggaaugugg ucagccucgg    180
uuuucgucga uguguauuua ggcuucucuc caacuuuaac ggcuaguucg uuuauagcca    240
uaaguggauu cuguuuuucu cgcucuacga acaaacuuu cu                         282

<210> SEQ ID NO 41
<211> LENGTH: 1042
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 41
aauuggggug guugggacac auggccaguu auaugauggg acuccuucua caaugaaua      60 uaucaucagu guuuaacguu ugguauucaa caagacguau ucaacaaag gcaugggaca    120 cagcauauga uaguaacauc caagcauauc aggacaugca uuaucaaaug uuucgugga    180 guucaaugca agguaguauu gcaccagcaa ugguggacga aaucuucau aaccuuugug    240 gccaaauguu uggguucagc uuaccauga gacaagucuu auuaacgca uugccaauca    300 cuuuuucauc guuuggaagu uggaugucgc cuagaguuuc ugaugguuuc caaacuguaa    360
gguauuauga uauaggucca ccagucauua accccgaaacg ugaugggaa guaccaguaa    420
```

| | |
|---|---|
| guaugauuga cgcauggacc uauaaauuua cagaaaaauu gccaaaaagu uuuuugccau | 480 |
| ggccaaugcc agaaggaaag gacaguacaa ugggauauga uccggaaaaa gaaccagcuc | 540 |
| uaauugauaa uucaaaugag acaggcaaug uauucagacc auuuauggca agaaauggca | 600 |
| acaauucuaa uuauuugcca accaacuaca caauugacgu aucacagaau ggucaugacg | 660 |
| agaguuguau uaauguugac cuuuuuaaca auguugcagg aguaacacua acaaauuaug | 720 |
| auggaaccgc aacaaacgca gacgucguac aacaggauc auacauuaag cagagagcaa | 780 |
| ugccuaucaa ugcaaaugcg guacgaccaa cugaaacacu cgacgcugcc aaccauacga | 840 |
| aaccuuuugc uauuggagga ggaagacucg uauauuuggg uggaacaauu gcaaauacaa | 900 |
| ccaauguggu aaacgcaaug cagaggaaac aaaggcuuuc aaaaccagca uucaaguggg | 960 |
| cacaugcuca gagacaacgu guauaugaca gcagucgucc agggauggac gcaaucacaa | 1020 |
| aguugugugc acgaaagucg gg | 1042 |

<210> SEQ ID NO 42
<211> LENGTH: 1042
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 42

| | |
|---|---|
| cccgacuuuc gugcacacaa cuuugugauu gcguccaucc cuggacgacu gcugucauau | 60 |
| acguugguc ucugagcaug ugcccacuug aaugcugguu ugaaagccu uguuuccuc | 120 |
| ugcauugcgu uuaccacauu gguuguauuu gcaauuguuc cacccaaaua uacgagucuu | 180 |
| ccuccuccaa uagcaaaagg uuucguaugg uuggcagcgu cgaguguuuc aguuggucgu | 240 |
| accgcauuug cauugauagg cauugcucuc ugcuuaaugu augauccugu gguacgacg | 300 |
| ucugcguuug uugcgguucc aucauaauuu guuaguguua cuccugcaac auuguuaaaa | 360 |
| aggucaacau uaauacaacu cucgucauga ccauucgug auacgucaau uguguaguug | 420 |
| guuggcaaau aauuagaauu gugccauuu cuugccauaa augguucugaa uacauugccu | 480 |
| gucucauuug aauuaucaau uagagcuggu ucuuuuccg gaucauaucc cauuguacug | 540 |
| uccuuuccuu cuggcauugg ccauggcaaa aaacuuuuug gcaauuuuuc uguaaauuua | 600 |
| uagguccaug cgucaaucau acuuacuggu acuucccau cacguuucgg guuaaugacu | 660 |
| gguggaccua uaucauaaua ccuuacaguu uggaaaccau cagaaacucu aggcgacauc | 720 |
| caacuuccaa acgaugaaaa agugauuggc aaugcguuaa auaagacuug ucucaauggu | 780 |
| aagcugaacc caaacauuug gccacaaagg uuaugaagaa uuucguccac cauugcuggu | 840 |
| gcaauacuac cuugcauuga acuccacgaa aacauuugau aaugcaugu cugauaugcu | 900 |
| uggauguuac uaucauaugc ugugucccau gccuuuguug aaauacgucu uguugaauac | 960 |
| caaacguuaa acacugauga uauauucauu guuagaagga ucccaucau auaacuggcc | 1020 |
| auguguccca accacccaaa uu | 1042 |

<210> SEQ ID NO 43
<211> LENGTH: 875
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 43

```
cuuaauauag caacgucguc uccgcguaac gagauuuggg agauugggguc guauccaaua      60
auucccaaua acauuauuua uugcgaucuu uguaauuaua gcguuccaca uauuacccaa     120
caaacucguu auucacacuc cugaugguac uccaccuuug acuuuuauau uucaaauuu      180
uguauuuuua auauuccag acaaauaacu uuuaucauau gcauuaacaa ucuuauugac      240
uagcaauugu gucugauagu aauaaaucuu agguacuuga cuaacuacaa uuucccaac      300
ucuucucacc auugucuuaa cuucaaaagu guuggcuga ugaucaaaug augcauaguc      360
aaaugguaau ccaaaguauc cagcuuguag uuucucaauc auucaauuu cucucgaug       420
cuguugaucu gguuuuucau caagcgucac uccaaagugu uccuuaaaac caugaccaua     480
uaggaaaagc auauaagauu caugaauaua ugcuucgaug uuagaugcga cagcaagucu     540
uaauuuacuc auucguuuu uaauaaagac acgugaaugu aacuuccau cccaagcaua       600
aacaauguug gccaauucuu gcgguguaua aauuuguaac agcauauuuu ccuugcuuu      660
aaauucccca uuucuccau cuuuugucca augcacuuuc ccaauacuug aacuccacu       720
uguuaaccac auuccuuccu uuauguaauc aucaaaacua auaaauucau guccuuugua     780
ccaugucauu acucuuugc auguuuugu aaacaaauca uuccaauuau cucuaucuau       840
accauguuca uuaccuucag augcgaguga guuga                               875
```

<210> SEQ ID NO 44
<211> LENGTH: 875
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (812)..(812)
<223> OTHER INFORMATION: a, c, u, g, unknown or other

<400> SEQUENCE: 44

```
ucaacucacu cgcaucugaa gguaaugaac augguauaga uagagauaau uggaaugauu      60
uguuuacaaa aacaugcaaa gaaguaauga caugguacaa aggacaugaa uuuauuaguu     120
uugaugauua cauaaaggaa ggaaugugu uaacaagugg aaguucaagu auugggaaag      180
ugcauuggac aaaagaugga gaaaauggga aauuaaagc aaggaaaaau augcuguuac      240
aaauuuauac accgcaagaa uuggccaaca uguuuaugc uugggaugga aguuacauu       300
cacgugucuu uauaaaaac gaaaugagua auuaagacu ugcugucgca ucuaacaucg       360
aagcauauau ucaugaaucu uauaugcuuu uccauauagg ucaugguuuu aaggaacacu     420
uuggagugac gcuugaugaa aaaccagauc aacagcauca gagagaaauu gaaaugauug     480
agaaacuaca agcuggauac uuuggauuac cauuugacua ugcaucauuu gaucaucagc    540
caacaacuuu ugaaguuaag acaaugguga gaagaguugg agaaauugua guagucaag     600
uaccuagaa uuauuacuau cagacacaau ugcuagucaa uaagauuguu aaugcauaug     660
auaaaaguua uuugcucgga auauuaaaa auacaaaauu ugaaauaua aaagucaaag      720
guggaguacc aucaggagug agaauaacga guuuguggg uaauaugugg aacgcuauaa     780
uuacaaagau cgcaauaaau aauguuauug gnaauuauug gaucgacccc aaucucccaa    840
aucucguuac gcggagacga cguugcuaua uuaag                              875
```

<210> SEQ ID NO 45

```
<211> LENGTH: 719
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 45
ugagcaaggg cgaggagcug uucaccgggg uggugcccau ccuggucgag cuggacggcg      60
acguaaacgg ccacaaguuc agcguguccg gcgagggcga gggcgaugcc accuacggca    120
agcugacccu gaaguucauc ugcaccaccg gcaagcugcc cgugcccugg cccacccucg    180
ugaccacccu gaccuacggc gugcagugcu ucagccgcua ccccgaccac augaagcagc    240
acgacuucuu caaguccgcc augcccgaag gcuacgucca ggagcgcacc aucuucuuca    300
aggacgacgg caacuacaag acccgcgccg aggugaaguu cgagggcgac acccggguga    360
accgcaucga gcugaagggc aucgacuuca aggaggacgg caacauccug ggcacaagc     420 uggaguacaa cuacaacagc cacaacgucu auaucauggc cgacaagcag aagaacggca    480
ucaaggugaa cuucaagauc cgccacaaca ucgaggacgg cagcgugcag cucgccgacc    540
acuaccagca gaacaccccc aucggcgacg gccccgugcu gcugcccgac aaccacuacc    600
ugagcaccca guccgcccug agcaaagacc ccaacgagaa gcgcgaucac auggccugc     660 uggaguucgu gaccgccgcc gggaucacuc ucggcaugga cgagcuguac aaguaaucu     719

<210> SEQ ID NO 46
<211> LENGTH: 719
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 46
agauuacuug uacagcucgu ccaugccgag agugaucccg gcggcgguca cgaacuccag      60
caggaccaug ugaucgcgcu ucucguuggg gucuuugcuc agggcggacu ggguugcucag    120 guagugguug ucgggcagca gcacggggcc gucgccgaug ggggguguucu gcugguagug    180 gucggcgagc ugcacgcugc cguccucgau guuguggcgg aucuugaagu ucaccuugau    240
gccguucuuc ugcuugucgg ccaugauaua gacguugugg cuguuguagu uguacuccag    300
cuugugcccc aggauguugc cguccuccuu gaagucgaug cccuucagcu cgaugcgguu    360 caccaggguug ucgcccucga acuucaccuc ggcgcgggu c uuguaguugc cgucguccuu    420
gaagaagaug gugcgcuccu ggacguagcc uucgggcaug gcggacuuga agaagucgug    480
cugcuucaug uggucggggu agcggcugaa gcacugcacg ccguaggcua ggguggucac    540
gagggugggc cagggcacgg gcagcuugcc gguggugcag augaacuuca ggucagcuu     600 gccguaggug gcaucgcccu cgcccucgcc ggacacgcug aacuugugcc guuuacguc     660 gccguccagc ucgaccagga ugggcaccac cccggugaac agcuccucgc ccuugcuca    719

<210> SEQ ID NO 47
<211> LENGTH: 615
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 47
```

| | |
|---|---:|
| auggaucuuu cuuucacucu uucggucgug ucggccaucc ucgccaucac ugcugugauu | 60 |
| gcuguauuua uugugauuuu uagguaucac aacacuguga ccaagaccau cgagacccac | 120 |
| acagacaaua ucgagacaaa cauggaugaa aaccuccgca uuccugugac ugcugagguu | 180 |
| ggaucaggcu acuucaagau gacugaugug uccuuugaca cgacaccuu gggcaaaauc | 240 |
| aagauccgca auggaaaguc ugaugcacag augaaggaag aagaugcgga ucuugucauc | 300 |
| acucccgugg agggucgagc acucgaagug acuguggggc agaaucucac cuuugaggga | 360 |
| acauucaagg uguggaacaa cacaucaaga aagaucaaca ucacugguau gcagauggug | 420 |
| ccaaagauua acccaucaaa ggccuuugc ggguagcucca acaccuccuc cuucaccccc | 480 |
| gucucuauug augaggauga aguuggcacc uuugugugug guaccaccuu uggcgcacca | 540 |
| auugcagcua ccgccggugg aaaucuuuuc gacauguacg ugcacgucac cuacucuggc | 600 |
| acugagaccg aguaa | 615 |

<210> SEQ ID NO 48
<211> LENGTH: 615
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 48

| | |
|---|---:|
| uuacucgguc ucagugccag aguaggugac gugcacguac augucgaaaa gauuuccacc | 60 |
| ggcgguagcu gcaauuggug cgccaaaggu gguaccacac acaaaggugc caacuucauc | 120 |
| cucaucaaua gagacggggg ugaaggagga ggguguggag cuaccgacaa aggccuuuga | 180 |
| uggguuaauc uuuggcacca ucugcauacc agugauguug aucuuucuug auguuuguu | 240 |
| ccacaccuug aauguucccu caaggugag auucugcccc acagucacuu cgagugcucg | 300 |
| accccuccacg ggagugauga caagauccgc aucuucuucc uucaucugug caucagacuu | 360 |
| uccauugcgg aucuugauuu ugcccaaggu gucgcuguca aaggacacau cagucaucuu | 420 |
| gaaguagccu gauccaaccu cagcagugac aggaaugcgg agguuuucau ccauguuugu | 480 |
| cucgauauug ucugugugg ucucgauggu cuuggucaca guuguugau accuaaaaau | 540 |
| cacaauaaau acagcaauca cagcagugau ggcgaggaug gccgacacga ccgaaagagu | 600 |
| gaaagaaaga uccau | 615 |

<210> SEQ ID NO 49
<211> LENGTH: 366
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 49

| | |
|---|---:|
| auggccacca cgacuaacac ucuuccuuuc ggcaggaccg gagcccaggc cgcuggcccu | 60 |
| ucuuacacca uggaagaucu ugaaggcucc augucuaugg cucgcauggg ucucuuuug | 120 |
| aucguugcua ucucaauugg uauccucguc cuggccguca ugaauguaug gaugggacca | 180 |
| aagaaggaca gcgauucuga cacugauaag gacaccgaug augaugacga cacugccaac | 240 |
| gauaacgaug augaggacaa auauaagaac aggaccaggg auaugaugcu ucuggcuggg | 300 |
| uccgcucuuc uguccucgu uucgccgccc accguuuuua ugucuuaccc caagaggagg | 360 |
| caguga | 366 |

<210> SEQ ID NO 50
<211> LENGTH: 366
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 50
ucacugccuc cucuuggggu aagacauaaa aacgguggcg gcggaaacga ggaacagaag    60
agcggaccca gccagaagca ucauaucccu gguccuguuc uuauauuugu ccucaucauc   120
guuaucguug gcagugucgu caucaucauc ggugccuua ucagugucag aaucgcuguc    180
cuucuuuggu cccauccaua cauucaugac ggccaggacg aggauaccaa uugagauagc   240
aacgaucaaa aagagaccca ugcgagccau agacauggag ccuucaagau cuuccauggu   300
guaagaaggg ccagcggccu gggcuccggu ccugccgaaa ggaagagugu uagucguggu   360
ggccau                                                              366

<210> SEQ ID NO 51
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ctggactgta ttggttgagt tcgcaggttt tagcgaagca gcaacatgtg acacag        56

<210> SEQ ID NO 52
<211> LENGTH: 56
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
cuggacugua uugguugagu ucgcagguuu uagcgaagca gcaacaugug acacag        56

<210> SEQ ID NO 53
<211> LENGTH: 56
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
cugugucaca uguugcugcu ucgcuaaaac cugcgaacuc aaccaauaca guccag        56

<210> SEQ ID NO 54
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
taatacgact cactataggc tggactgtat tggttgagtt cgc                      43

```
<210> SEQ ID NO 55
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
taatacgact cactataggt gtgtcacatg ttgctgcttc gct                    43

<210> SEQ ID NO 56
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
aaaccggagc tgaccacatt ccaagctgga ctgtattggt tgagttcgca ggttttagcg    60
aagcagcaac atgtgacaca g                                             81

<210> SEQ ID NO 57
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
aaaccggagc ugaccacauu ccaagcugga cuguauuggu ugaguucgca gguuuuagcg    60
aagcagcaac augugacaca g                                             81

<210> SEQ ID NO 58
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
cugugucaca uguugcugcu ucgcuaaaac cugcgaacuc aaccaauaca guccagcuug    60
gaaugugguc agcuccgguu u                                             81

<210> SEQ ID NO 59
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
taatacgact cactatagga aaccggagct gaccacattc caa                    43

<210> SEQ ID NO 60
<211> LENGTH: 43
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 60
taatacgact cactataggg ctgtgtcaca tgttgctgct tcg            43

<210> SEQ ID NO 61
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
gactgtattg gttgagttcg caggttttag cgaagcagca acatgtgaca cagttaaaaa    60
cgcaaaaatg attgctgctt acaaattagt taaaagattt tgtaaatggg acccaaccta   120
cattgaaatt tctgattgta tgctgccacc tccagacct                           159

<210> SEQ ID NO 62
<211> LENGTH: 159
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 62
gacuguauug guugaguucg cagguuuuag cgaagcagca acaugugaca caguuaaaaa    60
cgcaaaaaug auugcugcuu acaaauuagu uaaaagauuu uguaaauggg acccaaccua   120
cauugaaauu ucugauugua ugcugccacc uccagaccu                           159

<210> SEQ ID NO 63
<211> LENGTH: 158
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 63
aggucuggag guggcagcau acaaucagaa auuucaaugu agguuggguc ccauuuacaa    60
aaucuuuuaa cuaauuugua agcagcaauc auuuuugcgu uuuuaacugu gucacauguu   120
gcugcuucgc uaaaaccugc gaacucaacc aauacagu                            158

<210> SEQ ID NO 64
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
taatacgact cactataggg actgtattgg ttgagttcgc agg            43

<210> SEQ ID NO 65
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65

```
taatacgact cactataggg ctggaggtgg cagcatacaa t              41
```

<210> SEQ ID NO 66
<211> LENGTH: 7560
<212> TYPE: DNA
<213> ORGANISM: Penaeid shrimp infectious myonecrosis virus

<400> SEQUENCE: 66

```
ggcaatttca acctaattct aaaactgtta ccaacaattt ctgaactaca gaagaggcat     60
attcttcatc tacttcgaga agaagtagaa ggaaagaaag tttgcttcgt aaagcgagaa    120
aaacagaatc cacttatggc tataaacgaa ctagccgtta aagttggaaa gaagcctaaa    180
tacacatcga cgaaaaccgg agctgaccac attccaagct ggactgtatt ggttgagttc    240
gcaggtttta gcgaagcagc aacatgtgac acagttaaaa acgcaaaaat gattgctgct    300
tacaaattag ttaaaagatt ttgtaaatgg gacccaacct acattgaaat ttctgattgt    360
atgctgccac ctccagacct tacatcgtgc ggggacgttg agagtaatcc tggacctatc    420
atacatagcg ttgcatttgc aagaactggt tcagtatgga cacctgccac ctttactttc    480
aatactacat catccccggg tagactgcaa gtacaaatgt catccagcga caatagatat    540
gggttcaatt ctgttttact tgcagcaggt ggtacaacat ggggcacagc ttatttttca    600
caacgttgga acagtgactt tggattacag ccagatctaa ctataactgt aacaccacaa    660
ctaactggag aagaacttgg ttcaatttat tttgatgctg ttgaaactac aaatgcagag    720
gaagctatag aggcaacaat tataaatact actccaattg atgtaatggt agacacaaca    780
gcaggccctg taccaattga aggtgatttc aaacccacaa tgaaactcc cacgtgggta    840
agtaacacaa agcccattga tgtagcaaca cctaagactc gtgactacgt aaatcggtca    900
gtactgactc cacaactgat cacaaaaatg aaagaccatg tctatgcctt acaaaaggat    960
gaagttaaag atgtaacact tgcctcactc gatttcggct taaatccatc aagtgtactc   1020
ggaagatggt tgaaatggtt aactggcata gacatgagac tccatcttgg gaagaaagtc   1080
acaaaccata agttagaat gtttgtgcaa aaaacaaggt ttccactaaa gacagcaatt   1140
gaggaactaa acaatggtac tgttccacgt agattaagga gggatgttcg ttacattgaa   1200
aagccgttcg ataaagagga acataccgat atactgttat ctggtgatgt tgaggaaaac   1260
cccgggcctg aagggatgga acaggtatca ataacgccag aacaacttca atgattctg   1320
gcaatgcaaa atcaccacc aaagccaaag atcaagaac taagtgaaag ggaaattcag   1380
ttaaggctcc aaggaaatga agcaacccgc agacatcaaa gatttaaagg tgagcccatt   1440
gatccagttc taactagaga agatataatt agaaagcaca atcagcagaa tggaatattg   1500
cctgatgaaa aagaacagcc ggtagtggta ataacgtac accctttgga gaaggagtat   1560
tccattgaaa aggaaggaat ggtgtgggac gaggaacaat ttttgacgta tatacatgac   1620
aaatcatcaa gcaacgatca ctatgcctgc atctataacg ttgttacaca taacagattc   1680
ggtgtacttg aaatgccaga agatccactt gaaatgatta tcattatga accaggggaa   1740
gaaccaaaaa caaaacctaa aactaaaagt ggtaacaaaa gagaactaaa tgatgaaacc   1800
ttttacagaa agaagaagac aaaaacaaca aagagccaa aacacaagaa gcaaagaaa   1860
attgaccacg ataacatgtt ttcacgattg ctgagaaggc ttgacaaacc acaaattgta   1920
gcagcttggc taaacaacag accatcacgt aaattggtcg aaaaattagc tgacagtaaa   1980
ttcggaattg gatggcaagc aaagaagag tacacaacca gcatggtaat tgtatctgga   2040
tatatcaatt gtgaaccatt acccctaatc gtagataagc ttctctccgt cgataacaac   2100
```

-continued

```
tatgacatgt ggcaacagac tgacaagtat tttgacaatt tgatcacact gtgtaaccgc    2160
gtcagtgacg ttacctacac tagcgctcag ctgtgtagag atgcatctat cttgaataac    2220
aagaagatgc atgttgaaaa tggaaacatt gtttcaatgg aaaatcagtc tgaaattgat    2280
agtcaaacta aattcttttc actgttagaa gatgataaca aacttccaat tgtagatgag    2340
ctaagagtat tagctgatat gacggcacaa agaagcaacg taaacactgc tggtaatcat    2400
cttcgtgata atgactctat tagggccgac gctgttctag ctaacaatac agtacgtaac    2460
aattgtcaaa ttccaattcc tgtaacaaca ctaataccaa gacaaattcg tggattgaat    2520
ggtgtacttg taaatcagca attacggtta cagggaattg aaacacacat tacagacagt    2580
tatatttcaa aagctgagcc atctgactat tcgaaacaac tgtctgaaat ggttaatgct    2640
caaaagacat caacttggcg agcaaacaat atcgcatcac aggggtggga catgtttgat    2700
actgtacagt taaatacaaa catatcacaa aaagatcttt caatggacac tgctttgaca    2760
aagcttatgt tgttgtacca gctaacaaca caaaatctgc cagcaacaca attaccatca    2820
agcatttatt ctgcatttga ttcaagaaca cagcctactt tacaggatgg aatttggggt    2880
ataaataatg gtgttaatat atttggtgaa caatgcggtg gattagccgc gccagtctit    2940 ccattcagtg ggggcaccgg agaaattact ttccatctta ctttacaatc tgttccacag    3000
gaatttcaag aatcagcaat tttcgtacca gcaactgcac tacaagctgc aaaagagggt    3060
gctcgaacat tggcaatgta tgttttaatg tttgcagaat ggccatttgg tatgtataca    3120
aaaactaaac aaacaacaga caatgctggt aataatcaat cagatcaaat tttcattcac    3180
tccgaatcta ctgtacatat tccaggacaa aaacaaatgc atattgtgct gccaagaaaa    3240
gtgaacatgg tgaaccccac tacaattgca gaagcaaatg cacgtgtagt aattcaacca    3300
acatacggta cagtggcagc tggggcaggt gtcgcaaatg gtaatattaa cgtagctgct    3360
gttggtgtgg ccctgccaac tgtaaatttg actgactatc ttgtatcctg gcaaccgat    3420 ttcacacttg gcgacataaa acaattggtt gaaagaatga aaacaacact gccaattagt    3480
cgagacttga tggcagcacg tcaaaatgct atgttattga gtactctatt tcctccacta    3540
attcagagca atgtggcttc agacacaaag gaagtcccag aacagctgg agcatacact    3600 gcatgtcttg caaacttagg tattcctgaa acactaacag ttaactgggg agtagatata    3660
aatgttcagc cattgtatca gctacttgaa acggacatca cagcccacaa tcggtacgta    3720
ttaaacctgt tcaaaagaga agaagtggta gcaggtgcat atgaatttgg gtggttggga    3780
cacatggcca gttatatgat gggactcctt ctaacaatga atatatcatc agtgtttaac    3840
gtttggtatt caacaagacg tatttcaaca aaggcgtggg acacagcata tgatagtaac    3900
atccaagcat atcaggacat gcattatcaa atgttttcgt ggagttcaat gcaaggtagt    3960
attgcaccag caatggtgga cgaaattctt cataaccttt gtggccaaat gtttgggttc    4020
agcttaccat tgagacaagt cttatttaac gcattgccaa tcacttttc atcgtttgga    4080 agttggatgt tgcctagagt ttctgatggt ttccaaactg taaggtatta tgatgtaggt    4140
ccaccagtca ttaatgcaaa acgtgatggg gaagtaccag taagtatgat tgacgcatgg    4200
acctataaat ttacagaaaa attgccaaaa agtttttgc catggccaat gccagaagga    4260
aaggacagta caatgggata tgatccggaa aaagaaccag cactaattga taattcaaat    4320
gagacaggca atgtattcag accatttatg gcaagaaatg gcaacaattc taattatttg    4380
ccaaccaact acacaattga cgtatcacag aatggtcatg atgagagttg tattaatgtt    4440
```

```
gacctttta  acaatgttgc  aggagtaaca  ctaacaaatt  atgatggaac  cgcaacaaac    4500
gcagacgtcg  taccaacagg  atcatatatt  aagcagagag  caatgcctat  caatgcaaat    4560
gcggtacgac  caactgaaac  actcgacgct  gctaaccata  caaaacctttt tgctattgaa    4620 ggaggaagac  tcgtatattt  gggtggaaca  attgcaaata  caaccaatgt  ggtaaacgca    4680
atgcagagga  aacaaaggct  ttcaaaaccg  gcattcaagt  gggcacatgc  tcagagacaa    4740
cgtgtatatg  acagcagtcg  tccagggatg  gacgcaatca  caaagttgtg  tgcacgaaag    4800
tcgggtttta  tgaatgcccg  ttccacagca  atgatggcac  ccaagactgg  actcagcgct    4860
gttatagatc  aagcaccaaa  tacatctcaa  gacttgatcg  aacagccgag  tcagcaagag    4920
gttatggata  tgcaagcgac  agcaacagta  taaatcagat  atatcaaatt  gcattgcata    4980
gaaaggcaaa  acttataaca  gcaaagaaat  ggcaagaatt  aacaaaaggt  atttataatg    5040
catctaccct  gacaccgaag  atagttgacc  aaattataaa  ggatgaagga  agtgggaccg    5100
ataagacaaa  atatgtaaat  gttcctaaaa  taattactga  caaagaatta  caaacattct    5160
atgtaccaag  aagcaacgca  gacctagtta  taagaagaat  acgtttaatc  gacctttggc    5220
gtaacctaaa  accagatcaa  atggacgaga  ttcgtaatta  cactcatcta  gattatatct    5280
ttgtacaaaa  catttgtatc  tatatgttag  tatttggaat  agacacagtt  aaacacttta    5340
gacaaatagg  tctattcaat  gaaaggaatg  aatttattga  aattgcaaaa  cagttatcaa    5400
ccaaagggaa  aagatttgtt  gatgatgttg  ataaatgaa  acaaaaggta  tgtgaaatag    5460
ctactattgt  tggttatatg  gacccaaatg  ttgataaaat  agacgtaatg  aagaagtca    5520 actcactcgc  agctgaaggt  aatgaacatg  gtatagatag  agataattgg  aatgatttgt    5580
ttacaaaaac  atgcaaagaa  gtaatgacat  ggtacaaagg  acatgaattt  attagttttg    5640
atgattacat  aaaggaagga  atgtggttaa  caagtggaag  ttcaagtatt  gggaaagtgc    5700
attggacaaa  agatggagaa  aatgggaaat  ttaaagcaag  gaaaaatatg  ctgttacaaa    5760
tttatacacc  gcaagaattg  gccaacattg  tttatgcttg  ggatggaaag  ttacattcac    5820
gtgtctttat  taaaaacgaa  atgagtaaat  taagacttgc  tgtggcatct  aacatcgaag    5880
catatattca  tgaatcttat  atgctttcc  tatatggtca  tggtttaaa  gaatactttg    5940 gagtgacgct  tgacgaaaaa  ccagatcaac  agcatcagag  agaaattgaa  atgattgaga    6000
aactacaagc  tggatacttt  ggattaccat  ttgactatgc  atcatttgat  catcagccaa    6060
caactttcga  agttaagaca  atggtgagaa  gagttggaga  aattgtagtt  agtcaagtac    6120
ctaagaatta  ttactatcag  acacaattgc  tagtcaataa  gattgttaat  gcatatgata    6180 aaagttatttt gtctggaaat  attaaaaata  caaaatttga  aaatataaaa  gtcaaaggtg    6240
gagtaccatc  aggagtgaga  ataacgagtt  tgttgggtaa  tatgtggaac  gctataatta    6300
caaagatcgc  aataaataat  gttattggaa  ttattggata  cgacccaatc  tcccaaatct    6360
cgttacgcgg  agacgacgtt  gctatattaa  gtaaagatcc  agcagctctt  tatttactta    6420
gactatcata  tgctgcaatt  aatgcaattg  gcaaagatag  taagttaggt  atatctccaa    6480
aagtatgtga  attttacgg  aatgagatat  cagtgacagg  agtacgcggt  tggacatgta    6540
gaggaatagg  tggcataagt  caacgaaaac  catggaatcc  acaaccttgg  agtccaaatg    6600
atgaagtcga  aacaaatgca  agcaacattt  cattattaga  aagacgagca  ggaattgaac    6660
ttcaacaatt  acaccacata  aacaaagtta  aatggtcgag  acacgtcaga  caaagttata    6720
aatatctaga  attgccaaaa  cgacttggtg  gttttggaat  ctatcgattc  caggggtggt    6780
tacctaacgg  caaattacca  cttgccaaaa  agccccttggt taacgtagag  gacatacatc    6840
```

```
caagccaaga gctgtttttg cctttaagtg aacaacagaa aaagatctta gcacaggttg    6900
aaatgacaaa caaaatgcaa acagatgata tacctgggac acaaaaatta ttttcaaagg    6960
aatggataca gaaagtgcgt gcaaaaaaga tcatatggag tagaaatcag acaataccaa    7020
tccatactga tcacacagta cgtataccaa gatgggacga gaaaatcaaa ttcccaaggt    7080
ataaatcaga atatatatta aataataaaa tcaacttaac aatggagcaa gtgctaagac    7140
agtataacct cctaaaagaa gtggaacggt acgataaaga tctaaaagtg ccaaagttat    7200
tagacatttt ggacaaatgg ttcccggtcc aaagtagtaa aattaaaaca tatgaaagtc    7260
aaggttttca tagaacagac gcaattaacc ttgctgttgg tgaaattcca actgaaccag    7320
cagttaaaat aaatcctata ctaataaact ttgtcaagtt acatcttgaa agacaaggta    7380
ttagacatca gagaggtaga aataagatcg ccaaatttat ttaccaaaaa caaacaagc    7440 agagaacatg atactgcaaa gtagtttaca acaaatgtat aggtactaaa ttaagggacc    7500
aataaagaaa cttcgagttt cctataacac attcccagtt gggttttgtg gccagccatg    7560
```

<210> SEQ ID NO 67
<211> LENGTH: 7561
<212> TYPE: DNA
<213> ORGANISM: Penaeid shrimp infectious myonecrosis virus

<400> SEQUENCE: 67

```
ggcaatttca acctaattct aaaactgtta ccaacaattt ctgaactaca gaagaggcat      60
attcttcatc tacttcgaga agaagtagaa ggaaagaaag tttgtttcgt agagcgagaa     120
aaacagaatc cacttatggc tataaacgaa ctagccgtta aagttggaaa gaagcctaaa     180
tacacatcga cgaaaaccgg agctgaccac attccaagct ggactgtatt ggttgagttc     240
gcaggtttta gcgaagcagc aacatgtgac acagttaaaa acgcaaaaat gattgctgct     300
tacaaattag ttaaaagatt ttgtaaatgg gacccaacct acattgaaat ttctgattgt     360
atgctgccac ctccagacct tacatcgtgc ggggacgttg agagtaatcc tggacctatc     420
atacatagcg ttgcatttgc aagaactggt tcagtatgga cacctgccac ctttactttc     480
aatactacat catccccggg tagactgcaa gtacaaatgt catccagcga caatagatat     540
gggctcaatt ctgttttact tgcagcaggt ggtacaacat ggggcacagc ttattttca     600 caacgttgga acagtgactt tggattacag ccagatctaa ctataactgt aacaccacaa     660
ctaactggag aagaacttgg ttcaatttat tttgatgctg ttgaaactac aaatgcagag     720
gaagctatag aggcaacaat tataaatact actccaattg atgtaatggt agacacaaca     780
gcaggccctg taccaattga aggtgatttc aaacccacaa atgaaactcc cacgtgggta     840
agtaacacaa agcccattga tgtagcaaca cctaagactc gtgactacgc aaatcggtca     900
gtactgactc cacaattgat cacaaaaatg aaagaccatg tctatgcctt acaaaaggat     960
gaagttaaag atgtaacact tgcctcactc gatttcggct taaatccatc aagtgtactc    1020
ggaagatggt tgaaatggtt aactggcata gacatgagac tccatcttgg gaagaaagtc    1080
acaaaccata agttagaat gtttgtgcaa aaaacaaggt ttccactaaa gacagcaatt    1140
gaggaactaa acaatggtac tgttccacat agattaagga gggatgttcg ttacattgaa    1200
aagccgttcg ataaagagga acataccgat atactgttat ctggtgacgt tgaggaaaac    1260
cctgggcctg aagggatgga acaggtatca ataacgccag aacaacttca aatgattctg    1320
gcaatgcaaa aatcaccacc aaagccaaag atcaaagaac taagtgaaag ggaaattcag    1380
```

```
ttaaggctcc aaggaaatga agcaacccgc agacatcaaa gatttaaagg tgagcccatt    1440
gatccagttc taactagaga agatataatt agaaagcaca atcagcagaa tggaatattg    1500
cctgatgaaa aagaacagcc ggtagtggta aataacgtac acccttttgga gaaggagtat   1560 tccattgaaa aggaaggaat ggtgtgggac gaggaacaat ttttgacgta tatacatgac    1620
aaatcatcaa gcaacgatca ctatgcctgc atctataacg ttgttacaca taacagattc    1680
ggtgtacttg aaatgccaga agatccactt gaaacgattg atcattatga accaggggaa    1740
gaaccaaaaa caaaacctaa aactaaaagt ggtaacaaga gagaactaaa tgatgaaacc    1800
ttttacagaa agaagaagac aaaaacaaca aaagagccaa aaacacaaga gcaaaagaaa    1860
attgaccacg ataacatgtt ttcacgattg ctgagaaggc ttgacaaacc acaaattgta    1920
gcagcttggc taaacaacag accatcacgt aaattggtcg aaaaattagc tgacagtaaa    1980
ttcggaattg gatggcaagc aaaagaagag tacacaacca gcatggtaat tgtatctgga    2040
tatatcaatt gtgaaccatt acccctaatc gtagataagc ttctctccgt cgataacaac    2100
tatgacatgt ggcaacagac tgacaagtat tttaacaatt tgatcacact gtgtaaccgc    2160
gtcagtgacg ttacctacac tagcgctcag ctgtgtagag atgcatctat cttgaataac    2220
aagaagatgc atgttgaaaa tggaaacatt gtttcaatgg aaaatcagtc tgaaattgat    2280
agtcaaacta aattcttttc actgttagaa gatgataaca aacttccaat tgtagatgag    2340
ctaagagtat tagctgatat gacggcacaa agaagcaacg taaacactgc tggtaatcat    2400
cttcgtgata atgactctat tagggccgac gctgttctag ctaacaatac agtacgtaac    2460
aattgtcaaa ttccaattcc tgtaacaaca ctaataccaa gacaaattcg tggattgaat    2520
ggtgtacttg taaatcagca attacggtta cagggaattg aaacacacat tacagacagt    2580
tatatttcaa aagctgagcc atctgactat tcgaaacaac tgtctgaaat ggttaatgct    2640
caaaagacat caacttggcg agcaaacaat atcgcatcac agggtgggga catgtttgat    2700
actgtacagt taaatacaaa catatcgcaa aaagatcttt caatggacac tgcttttgaca   2760 aagcttatgt tgttgtacca gctaacaaca caaaatctgc cagcaacaca attaccatca    2820
agcatttatt ctgcatttga ttcaagaaca cagcccactt tacaggatgg aatttgggt    2880 ataaataatg gtgctaatat atttggtgaa caatgcggtg gattagccgc gccagtcttt    2940
ccattcagtg ggggcaccgg agaaattact ttccatctta ctttacaatc tgttccacag    3000
gaatttcaag aatcagcaat tttcgtacca gcaactgcac tacaagctgc aaaagagggt    3060
gctcgaacat tggcaatgta tgttttaatg tttgcagaat ggccatttgg tatgtataca    3120
aaaactaaac aaacaacaga caatgctggt aataatcaat cagatcaaat tttcattcac    3180
tccgaatcta ctgtacatat tccaggacaa aaacaaatgc atattgtgct gccaagaaaa    3240
gtgaacatgg tgaaccccac tacaattgca gaagcaaatg cacgtgtagt aattcaacca    3300
acatacggta cagtggcagc tggggcaggt gtcgcaaatg gtaatattaa cgtagctgct    3360
gttggtgtgg ccttgccaac tgtaaatttg actgactatc ttgtatcctg gcaaccgat    3420 ttcacacttg gcgacataaa acaattggtt gaaagaatga aacaacact gccaattagt    3480 cgagacttga tggcagcacg tcaaaatgct atgttattga gtactctatt tcctccacta   3540
attcagagca atgtggcttc agacacaaag gaagtcccag gaacagctgg agcatacact    3600
gcatgtcttg caaacttagg tattcctgaa acactaacag ttaactgggg agaagatata    3660
aatgttcagc cattgtatca gctacttgaa acggacatca cagcccacaa tcggtacgta    3720
ttaaacctgt ttaaaagaga agaagtgata gcaggtgcat atgaatttgg gtggttggga    3780
```

```
cacatggcca gttatatgat gggactcctt ctaacaatga atatatcatc agtgtttaac    3840
gtttggtatt caacaagacg tatttcaaca aaggcgtggg acacagcata tgatagtaac    3900
atccaagcat atcaggacat gcattatcga atgttttcgt ggagttcaat gcaaggtagt    3960
attgcaccag caatggtgga cgaaattctt cataaccttt gtggccaaat gtttgggttc    4020
agcttaccat tgagacaagt cttatttaac gcattgccaa tcactttttc atcgtttgga    4080
agttggatgt cgcctagagt ttctgatggt ttccaaactg taaggtatta tgatataggt    4140
ccaccagtca ttaatgcaaa acgtgatggg aagtaccag taagtatgat tgacgcatgg     4200
acctataaat ttacagaaaa attgccaaaa agttttttgc catggccaat gccagaagga    4260
aaggacagta caatgggata tgatccggaa aaagaaccag cactaattga taattcaaat    4320
gagacaggca atgtattcag accatttatg gcaagaaatg gcaacaattc taattatttg    4380
ccaaccaact acacaattga cgtatcacag aatggtcatg acgagagttg tattaatgtt    4440
gaccttttta acaatgttgc aggagtaaca ctaacaaatt atgatggaac cgcaacaaac    4500
gcagacgtcg taccaacagg atcatacatt aagcagagag caatgcctat caatgcaaat    4560
gcggtacgac caactgaaac actcgacgct gctaaccata caaacccttt tgctattgaa    4620
ggaggaagac tcgtatattt gggtggaaca attgcaaata caaccaatgt ggtaaacgca    4680
atgcaaagga aacaaaggct ttcaaaacca gcattcaagt gggcacatgc tcagagacaa    4740
cgtgtatatg acagcagtcg tccagggatg gacgcaatca caagttgtg tgcacgaaag    4800 tcgggttta tgaatgcccg ttccacagca atgatggcac ccaagactgg actcagcgct    4860
gttatagatc aagcaccaaa tacatctcaa gacttgatcg aacaaccgag tcagcaagag    4920
gttatggata tgcaagcgac agcaacagta taaatcagat atatcaaatt gcattgcata    4980
gaaaggcaaa acttataaca gcaaagaaat ggcaagaatt aacaaaaggt atttataatg    5040 catctacccct gacaccgaag atagttgacc aaattataaa ggatgaagga agcgggaccg    5100
ataagacaaa atatgtaaat gttcctaaaa taattactga caaagaatta caaacattct    5160
atgtaccaag aagcaacgca gacctagtta taagaagaat acgtttaatc gacctttggc    5220
gtaacctaaa accagatcaa atggacgaga ttcgtaatta cactcatcta gattatatct    5280
ttgtacaaaa catttgtatc tatatgttag tatttggaat agacacagtt aaacacttta    5340
gacaaatagg tctattcaat gaaaggaatg aatttattga aattgcaaaa cagttatcaa    5400
ccaaagggaa aagatttgtt gatgatgttg ataatatgaa acaaaaggta tgtgaaatag    5460
ctactattgt tggttatatg gacccaaatg ttgataaaat agacgtaatg gaagaagtca    5520
actcactcgc agctgaaggt aatgaacatg gtatagatag agataattgg aatgatttgt    5580
ttacaaaaac atgcaaagaa gtaatgacat ggtacaaagg acatgaattt attagttttg    5640
atgattacat aaaggaagga atgtggttaa caagtggaag ttcaagtatt gggaaagtgc    5700 attgacaaa agatggagaa atgggaaat ttaaagcaag gaaaaatatg ctgttacaaa    5760
tttatacacc gcaagaattg gccaacattg tttatgcttg ggatggaaag ttacattcac    5820
gtgtatttat taaaacgaa atgagtaaat taagacttgc tgtggcatct aacatcgaag    5880
catatattca tgaatcttat atgctttcc tatatggtca tggttttaaa gaatactttg    5940
gagtgacgct tgacgaaaaa ccagatcaac agcatcagag agaaattgaa atgattgaga    6000
aactacaagc tggatacttt ggattaccat ttgactatgc atcatttgat catcagccaa    6060
caactttcga agttaagaca atggtgagaa gagttggaga aattgtagtt agtcaagtac    6120
```

```
ctaagaatta ttactatcag acacaattgc tagtcaataa gattgttaat gcatatgata    6180
aaagttattt gtctggaaat attaaaaata caaaatttga aaatataaaa gtcaaaggtg    6240
gagtaccatc aggagtgaga ataacgagtt tgttgggtaa tatgtggaac gctataatta    6300
caaagatcgc aataaataat gttattggaa ttattggata cgacccaatc tcccaaatct    6360
cgttacgcgg agacgacgtt gctatattaa gtaaagatcc agcagctctt tatttactta    6420
gactatcata tgctgcaatt aatgcaattg gcaaagatag taagttaggt atatctccaa    6480
aagtatgtga atttttacgg aatgagatat cagtgacagg agtacgcggt tggacatgta    6540
gaggaatagg tggcataagt caacgaaaac catggaatcc acaaccttgg agtccaaatg    6600
atgaagtcga aacaaatgca agcaacattt cattattaga aagacgagca ggaattgaac    6660
ttcaacaatt acaccacata aacaaagtta aatggtcgag acacgtcaga caaagttata    6720
aatatctaga attgccaaaa cgacttggtg gttttggaat ctatcgATTT cagGGgtggt    6780
```

```
tacctaacgg caaattacca cttgccaaaa agcccttggt taacgtagag gacatacatc    6840
caagccaaga gctgtttttg cctttaagtg aacaacagaa aaagatctta gcacaggttg    6900
aaatgacaaa caaaatgcaa acagatgata tacctgggac acaaaaatta ttttcaaagg    6960
aatggataca gaaagtgcgt gcaaaaaaga tcatatggag tagaaatcag acaataccaa    7020
tccatactga tcacacagta cgtataccaa gatgggacga gaaaatcaaa ttcccaaggt    7080
ataaatcaga atatatatta aataataaaa tcaacttaac aatggagcaa gtgctaagac    7140 agtataaccct cctaaaagaa gtggaacggt acgataaaga tctaaaagtg ccaaagttat    7200
tagacatttt ggacaatggt tcccggtcc aaagtagtaa aattaaaaca tatgaaagtc    7260
aaggttttca tagaacagac gcaattaatc ttgctgttgg tgaaattcca actgaaccag    7320
cagttaaaat aaatcctata ctaataaact ttgtcaagtt acatcttgaa agacaaggta    7380
ttagacatca gagaggtaga aataagatcg ccaaatttat ttaccaaaaa acaaaacaag    7440
cagagaacat gatactgcaa agtagtttac aacaaatgta taggtactaa attaagggac    7500
caataaagaa acttcgagtt tcctataaca cattcccagt tgggttttgt ggccagccat    7560
g                                                                    7561
```

<210> SEQ ID NO 68
<211> LENGTH: 908
<212> TYPE: PRT
<213> ORGANISM: Penaeid shrimp infectious myonecrosis virus

<400> SEQUENCE: 68

```
Met His Val Glu Asn Gly Asn Ile Val Ser Met Glu Asn Gln Ser Glu
1               5                   10                  15

Ile Asp Ser Gln Thr Lys Phe Phe Ser Leu Leu Glu Asp Asp Asn Lys
            20                  25                  30

Leu Pro Ile Val Asp Glu Leu Arg Val Leu Ala Asp Met Thr Ala Gln
        35                  40                  45

Arg Ser Asn Val Asn Thr Ala Gly Asn His Leu Arg Asp Asn Asp Ser
    50                  55                  60

Ile Arg Ala Asp Ala Val Leu Ala Asn Asn Thr Val Arg Asn Cys
65                  70                  75                  80

Gln Ile Pro Ile Pro Val Thr Thr Leu Ile Pro Arg Gln Ile Arg Gly
                85                  90                  95

Leu Asn Gly Val Leu Val Asn Gln Gln Leu Arg Leu Gln Gly Ile Glu
            100                 105                 110
```

-continued

```
Thr His Ile Thr Asp Ser Tyr Ile Ser Lys Ala Glu Pro Ser Asp Tyr
        115                 120                 125
Ser Lys Gln Leu Ser Glu Met Val Asn Ala Gln Lys Thr Ser Thr Trp
    130                 135                 140
Arg Ala Asn Asn Ile Ala Ser Gln Gly Trp Asp Met Phe Asp Thr Val
145                 150                 155                 160
Gln Leu Asn Thr Asn Ile Ser Gln Lys Asp Leu Ser Met Asp Thr Ala
                165                 170                 175
Leu Thr Lys Leu Met Leu Leu Tyr Gln Leu Thr Thr Gln Asn Leu Pro
            180                 185                 190
Ala Thr Gln Leu Pro Ser Ser Ile Tyr Ser Ala Phe Asp Ser Arg Thr
        195                 200                 205
Gln Pro Thr Leu Gln Asp Gly Ile Trp Gly Ile Asn Asn Gly Val Asn
    210                 215                 220
Ile Phe Gly Glu Gln Cys Gly Gly Leu Ala Ala Pro Val Phe Pro Phe
225                 230                 235                 240
Ser Gly Gly Thr Gly Glu Ile Thr Phe His Leu Thr Leu Gln Ser Val
                245                 250                 255
Pro Gln Glu Phe Gln Glu Ser Ala Ile Phe Val Pro Ala Thr Ala Leu
            260                 265                 270
Gln Ala Ala Lys Glu Gly Ala Arg Thr Leu Ala Met Tyr Val Leu Met
        275                 280                 285
Phe Ala Glu Trp Pro Phe Gly Met Tyr Thr Lys Thr Lys Gln Thr Thr
    290                 295                 300
Asp Asn Ala Gly Asn Asn Gln Ser Asp Gln Ile Phe Ile His Ser Glu
305                 310                 315                 320
Ser Thr Val His Ile Pro Gly Gln Lys Gln Met His Ile Val Leu Pro
                325                 330                 335
Arg Lys Val Asn Met Val Asn Pro Thr Thr Ile Ala Glu Ala Asn Ala
            340                 345                 350
Arg Val Val Ile Gln Pro Thr Tyr Gly Thr Val Ala Ala Gly Ala Gly
        355                 360                 365
Val Ala Asn Gly Asn Ile Asn Val Ala Ala Val Gly Val Ala Leu Pro
    370                 375                 380
Thr Val Asn Leu Thr Asp Tyr Leu Val Ser Trp Ala Thr Asp Phe Thr
385                 390                 395                 400
Leu Gly Asp Ile Lys Gln Leu Val Glu Arg Met Lys Thr Thr Leu Pro
                405                 410                 415
Ile Ser Arg Asp Leu Met Ala Ala Arg Gln Asn Ala Met Leu Leu Ser
            420                 425                 430
Thr Leu Phe Pro Pro Leu Ile Gln Ser Asn Val Ala Ser Asp Thr Lys
        435                 440                 445
Glu Val Pro Gly Thr Ala Gly Ala Tyr Thr Ala Cys Leu Ala Asn Leu
    450                 455                 460
Gly Ile Pro Glu Thr Leu Thr Val Asn Trp Gly Val Asp Ile Asn Val
465                 470                 475                 480
Gln Pro Leu Tyr Gln Leu Leu Glu Thr Asp Ile Thr Ala His Asn Arg
                485                 490                 495
Tyr Val Leu Asn Leu Phe Lys Arg Glu Val Val Ala Gly Ala Tyr
            500                 505                 510
Glu Phe Gly Trp Leu Gly His Met Ala Ser Tyr Met Met Gly Leu Leu
        515                 520                 525
Leu Thr Met Asn Ile Ser Ser Val Phe Asn Val Trp Tyr Ser Thr Arg
```

```
            530                 535                 540
Arg Ile Ser Thr Lys Ala Trp Asp Thr Ala Tyr Asp Ser Asn Ile Gln
545                 550                 555                 560

Ala Tyr Gln Asp Met His Tyr Gln Met Phe Ser Trp Ser Ser Met Gln
                565                 570                 575

Gly Ser Ile Ala Pro Ala Met Val Asp Glu Ile Leu His Asn Leu Cys
            580                 585                 590

Gly Gln Met Phe Gly Phe Ser Leu Pro Leu Arg Gln Val Leu Phe Asn
        595                 600                 605

Ala Leu Pro Ile Thr Phe Ser Ser Phe Gly Ser Trp Met Leu Pro Arg
    610                 615                 620

Val Ser Asp Gly Phe Gln Thr Val Arg Tyr Tyr Asp Val Gly Pro Pro
625                 630                 635                 640

Val Ile Asn Ala Lys Arg Asp Gly Glu Val Pro Val Ser Met Ile Asp
                645                 650                 655

Ala Trp Thr Tyr Lys Phe Thr Glu Lys Leu Pro Lys Ser Phe Leu Pro
            660                 665                 670

Trp Pro Met Pro Glu Gly Lys Asp Ser Thr Met Gly Tyr Asp Pro Glu
        675                 680                 685

Lys Glu Pro Ala Leu Ile Asp Asn Ser Asn Glu Thr Gly Asn Val Phe
    690                 695                 700

Arg Pro Phe Met Ala Arg Asn Gly Asn Ser Asn Tyr Leu Pro Thr
705                 710                 715                 720

Asn Tyr Thr Ile Asp Val Ser Gln Asn Gly His Asp Glu Ser Cys Ile
                725                 730                 735

Asn Val Asp Leu Phe Asn Asn Val Ala Gly Val Thr Leu Thr Asn Tyr
            740                 745                 750

Asp Gly Thr Ala Thr Asn Ala Asp Val Val Pro Thr Gly Ser Tyr Ile
        755                 760                 765

Lys Gln Arg Ala Met Pro Ile Asn Ala Asn Ala Val Arg Pro Thr Glu
    770                 775                 780

Thr Leu Asp Ala Ala Asn His Thr Lys Pro Phe Ala Ile Glu Gly Gly
785                 790                 795                 800

Arg Leu Val Tyr Leu Gly Gly Thr Ile Ala Asn Thr Thr Asn Val Val
                805                 810                 815

Asn Ala Met Gln Arg Lys Gln Arg Leu Ser Lys Pro Ala Phe Lys Trp
            820                 825                 830

Ala His Ala Gln Arg Gln Arg Val Tyr Asp Ser Ser Arg Pro Gly Met
        835                 840                 845

Asp Ala Ile Thr Lys Leu Cys Ala Arg Lys Ser Gly Phe Met Asn Ala
    850                 855                 860

Arg Ser Thr Ala Met Met Ala Pro Lys Thr Gly Leu Ser Ala Val Ile
865                 870                 875                 880

Asp Gln Ala Pro Asn Thr Ser Gln Asp Leu Ile Glu Gln Pro Ser Gln
                885                 890                 895

Gln Glu Val Met Asp Met Gln Ala Thr Ala Thr Val
            900                 905
```

<210> SEQ ID NO 69
<211> LENGTH: 908
<212> TYPE: PRT
<213> ORGANISM: Penaeid shrimp infectious myonecrosis virus

<400> SEQUENCE: 69

```
Met His Val Glu Asn Gly Asn Ile Val Ser Met Glu Asn Gln Ser Glu
1               5                   10                  15

Ile Asp Ser Gln Thr Lys Phe Phe Ser Leu Leu Glu Asp Asp Asn Lys
            20                  25                  30

Leu Pro Ile Val Asp Glu Leu Arg Val Leu Ala Asp Met Thr Ala Gln
        35                  40                  45

Arg Ser Asn Val Asn Thr Ala Gly Asn His Leu Arg Asp Asn Asp Ser
    50                  55                  60

Ile Arg Ala Asp Ala Val Leu Ala Asn Asn Thr Val Arg Asn Asn Cys
65                  70                  75                  80

Gln Ile Pro Ile Pro Val Thr Thr Leu Ile Pro Arg Gln Ile Arg Gly
                85                  90                  95

Leu Asn Gly Val Leu Val Asn Gln Gln Leu Arg Leu Gln Gly Ile Glu
            100                 105                 110

Thr His Ile Thr Asp Ser Tyr Ile Ser Lys Ala Glu Pro Ser Asp Tyr
        115                 120                 125

Ser Lys Gln Leu Ser Glu Met Val Asn Ala Gln Lys Thr Ser Thr Trp
    130                 135                 140

Arg Ala Asn Asn Ile Ala Ser Gln Gly Trp Asp Met Phe Asp Thr Val
145                 150                 155                 160

Gln Leu Asn Thr Asn Ile Ser Gln Lys Asp Leu Ser Met Asp Thr Ala
                165                 170                 175

Leu Thr Lys Leu Met Leu Leu Tyr Gln Leu Thr Thr Gln Asn Leu Pro
            180                 185                 190

Ala Thr Gln Leu Pro Ser Ser Ile Tyr Ser Ala Phe Asp Ser Arg Thr
        195                 200                 205

Gln Pro Thr Leu Gln Asp Gly Ile Trp Gly Ile Asn Asn Gly Ala Asn
    210                 215                 220

Ile Phe Gly Glu Gln Cys Gly Gly Leu Ala Ala Pro Val Phe Pro Phe
225                 230                 235                 240

Ser Gly Gly Thr Gly Glu Ile Thr Phe His Leu Thr Leu Gln Ser Val
                245                 250                 255

Pro Gln Glu Phe Gln Glu Ser Ala Ile Phe Val Pro Ala Thr Ala Leu
            260                 265                 270

Gln Ala Ala Lys Glu Gly Ala Arg Thr Leu Ala Met Tyr Val Leu Met
        275                 280                 285

Phe Ala Glu Trp Pro Phe Gly Met Tyr Thr Lys Thr Lys Gln Thr Thr
    290                 295                 300

Asp Asn Ala Gly Asn Asn Gln Ser Asp Gln Ile Phe Ile His Ser Glu
305                 310                 315                 320

Ser Thr Val His Ile Pro Gly Gln Lys Gln Met His Ile Val Leu Pro
                325                 330                 335

Arg Lys Val Asn Met Val Asn Pro Thr Thr Ile Ala Glu Ala Asn Ala
            340                 345                 350

Arg Val Val Ile Gln Pro Thr Tyr Gly Thr Val Ala Ala Gly Ala Gly
        355                 360                 365

Val Ala Asn Gly Asn Ile Asn Val Ala Ala Val Gly Val Ala Leu Pro
    370                 375                 380

Thr Val Asn Leu Thr Asp Tyr Leu Val Ser Trp Ala Thr Asp Phe Thr
385                 390                 395                 400

Leu Gly Asp Ile Lys Gln Leu Val Glu Arg Met Lys Thr Thr Leu Pro
                405                 410                 415

Ile Ser Arg Asp Leu Met Ala Ala Arg Gln Asn Ala Met Leu Leu Ser
```

```
            420                 425                 430
Thr Leu Phe Pro Pro Leu Ile Gln Ser Asn Val Ala Ser Asp Thr Lys
            435                 440                 445
Glu Val Pro Gly Thr Ala Gly Ala Tyr Thr Ala Cys Leu Ala Asn Leu
            450                 455                 460
Gly Ile Pro Glu Thr Leu Thr Val Asn Trp Gly Glu Asp Ile Asn Val
465                 470                 475                 480
Gln Pro Leu Tyr Gln Leu Leu Glu Thr Asp Ile Thr Ala His Asn Arg
            485                 490                 495
Tyr Val Leu Asn Leu Phe Lys Arg Glu Glu Val Ile Ala Gly Ala Tyr
            500                 505                 510
Glu Phe Gly Trp Leu Gly His Met Ala Ser Tyr Met Met Gly Leu Leu
            515                 520                 525
Leu Thr Met Asn Ile Ser Ser Val Phe Asn Val Trp Tyr Ser Thr Arg
            530                 535                 540
Arg Ile Ser Thr Lys Ala Trp Asp Thr Ala Tyr Asp Ser Asn Ile Gln
545                 550                 555                 560
Ala Tyr Gln Asp Met His Tyr Arg Met Phe Ser Trp Ser Ser Met Gln
                565                 570                 575
Gly Ser Ile Ala Pro Ala Met Val Asp Glu Ile Leu His Asn Leu Cys
            580                 585                 590
Gly Gln Met Phe Gly Phe Ser Leu Pro Leu Arg Gln Val Leu Phe Asn
            595                 600                 605
Ala Leu Pro Ile Thr Phe Ser Ser Phe Gly Ser Trp Met Ser Pro Arg
            610                 615                 620
Val Ser Asp Gly Phe Gln Thr Val Arg Tyr Tyr Asp Ile Gly Pro Pro
625                 630                 635                 640
Val Ile Asn Ala Lys Arg Asp Gly Glu Val Pro Val Ser Met Ile Asp
                645                 650                 655
Ala Trp Thr Tyr Lys Phe Thr Glu Lys Leu Pro Lys Ser Phe Leu Pro
            660                 665                 670
Trp Pro Met Pro Glu Gly Lys Asp Ser Thr Met Gly Tyr Asp Pro Glu
            675                 680                 685
Lys Glu Pro Ala Leu Ile Asp Asn Ser Asn Glu Thr Gly Asn Val Phe
            690                 695                 700
Arg Pro Phe Met Ala Arg Asn Gly Asn Ser Asn Tyr Leu Pro Thr
705                 710                 715                 720
Asn Tyr Thr Ile Asp Val Ser Gln Asn Gly His Asp Glu Ser Cys Ile
                725                 730                 735
Asn Val Asp Leu Phe Asn Asn Val Ala Gly Val Thr Leu Thr Asn Tyr
            740                 745                 750
Asp Gly Thr Ala Thr Asn Ala Asp Val Val Pro Thr Gly Ser Tyr Ile
            755                 760                 765
Lys Gln Arg Ala Met Pro Ile Asn Ala Asn Ala Val Arg Pro Thr Glu
            770                 775                 780
Thr Leu Asp Ala Ala Asn His Thr Lys Pro Phe Ala Ile Glu Gly Gly
785                 790                 795                 800
Arg Leu Val Tyr Leu Gly Gly Thr Ile Ala Asn Thr Thr Asn Val Val
                805                 810                 815
Asn Ala Met Gln Arg Lys Gln Arg Leu Ser Lys Pro Ala Phe Lys Trp
            820                 825                 830
Ala His Ala Gln Arg Gln Arg Val Tyr Asp Ser Ser Arg Pro Gly Met
            835                 840                 845
```

Asp Ala Ile Thr Lys Leu Cys Ala Arg Lys Ser Gly Phe Met Asn Ala
            850                 855                 860

Arg Ser Thr Ala Met Met Ala Pro Lys Thr Gly Leu Ser Ala Val Ile
865                 870                 875                 880

Asp Gln Ala Pro Asn Thr Ser Gln Asp Leu Ile Glu Gln Pro Ser Gln
            885                 890                 895

Gln Glu Val Met Asp Met Gln Ala Thr Ala Thr Val
            900                 905

<210> SEQ ID NO 70
<211> LENGTH: 736
<212> TYPE: PRT
<213> ORGANISM: Penaeid shrimp infectious myonecrosis virus

<400> SEQUENCE: 70

Met Asp Glu Ile Arg Asn Tyr Thr His Leu Asp Tyr Ile Phe Val Gln
1               5                   10                  15

Asn Ile Cys Ile Tyr Met Leu Val Phe Gly Ile Asp Thr Val Lys His
                20                  25                  30

Phe Arg Gln Ile Gly Leu Phe Asn Glu Arg Asn Glu Phe Ile Glu Ile
            35                  40                  45

Ala Lys Gln Leu Ser Thr Lys Gly Lys Arg Phe Val Asp Asp Val Asp
        50                  55                  60

Asn Met Lys Gln Lys Val Cys Glu Ile Ala Thr Ile Val Gly Tyr Met
65                  70                  75                  80

Asp Pro Asn Val Asp Lys Ile Asp Val Met Glu Glu Val Asn Ser Leu
                85                  90                  95

Ala Ala Glu Gly Asn Glu His Gly Ile Asp Arg Asp Asn Trp Asn Asp
            100                 105                 110

Leu Phe Thr Lys Thr Cys Lys Glu Val Met Thr Trp Tyr Lys Gly His
        115                 120                 125

Glu Phe Ile Ser Phe Asp Asp Tyr Ile Lys Glu Gly Met Trp Leu Thr
130                 135                 140

Ser Gly Ser Ser Ser Ile Gly Lys Val His Trp Thr Lys Asp Gly Glu
145                 150                 155                 160

Asn Gly Lys Phe Lys Ala Arg Lys Asn Met Leu Leu Gln Ile Tyr Thr
                165                 170                 175

Pro Gln Glu Leu Ala Asn Ile Val Tyr Ala Trp Asp Gly Lys Leu His
            180                 185                 190

Ser Arg Val Phe Ile Lys Asn Glu Met Ser Lys Leu Arg Leu Ala Val
        195                 200                 205

Ala Ser Asn Ile Glu Ala Tyr Ile His Glu Ser Tyr Met Leu Phe Leu
210                 215                 220

Tyr Gly His Gly Phe Lys Glu Tyr Phe Gly Val Thr Leu Asp Glu Lys
225                 230                 235                 240

Pro Asp Gln Gln His Gln Arg Glu Ile Glu Met Ile Glu Lys Leu Gln
                245                 250                 255

Ala Gly Tyr Phe Gly Leu Pro Phe Asp Tyr Ala Ser Phe Asp His Gln
            260                 265                 270

Pro Thr Thr Phe Glu Val Lys Thr Met Val Arg Arg Val Gly Glu Ile
        275                 280                 285

Val Val Ser Gln Val Pro Lys Asn Tyr Tyr Gln Thr Gln Leu Leu
290                 295                 300

Val Asn Lys Ile Val Asn Ala Tyr Asp Lys Ser Tyr Leu Ser Gly Asn

-continued

```
                305                 310                 315                 320
        Ile Lys Asn Thr Lys Phe Glu Asn Ile Lys Val Lys Gly Gly Val Pro
                        325                 330                 335

Ser Gly Val Arg Ile Thr Ser Leu Leu Gly Asn Met Trp Asn Ala Ile
                        340                 345                 350

Ile Thr Lys Ile Ala Ile Asn Asn Val Ile Gly Ile Gly Tyr Asp
                        355                 360                 365

Pro Ile Ser Gln Ile Ser Leu Arg Gly Asp Val Ala Ile Leu Ser
            370                 375                 380

Lys Asp Pro Ala Ala Leu Tyr Leu Leu Arg Leu Ser Tyr Ala Ala Ile
        385                 390                 395                 400

Asn Ala Ile Gly Lys Asp Ser Lys Leu Gly Ile Ser Pro Lys Val Cys
                        405                 410                 415

Glu Phe Leu Arg Asn Glu Ile Ser Val Thr Gly Val Arg Gly Trp Thr
                        420                 425                 430

Cys Arg Gly Ile Gly Gly Ile Ser Gln Arg Lys Pro Trp Asn Pro Gln
                        435                 440                 445

Pro Trp Ser Pro Asn Asp Glu Val Glu Thr Asn Ala Ser Asn Ile Ser
                        450                 455                 460

Leu Leu Glu Arg Arg Ala Gly Ile Glu Leu Gln Gln Leu His His Ile
        465                 470                 475                 480

Asn Lys Val Lys Trp Ser Arg His Val Arg Gln Ser Tyr Lys Tyr Leu
                        485                 490                 495

Glu Leu Pro Lys Arg Leu Gly Gly Phe Gly Ile Tyr Arg Phe Gln Gly
                        500                 505                 510

Trp Leu Pro Asn Gly Lys Leu Pro Leu Ala Lys Lys Pro Leu Val Asn
                        515                 520                 525

Val Glu Asp Ile His Pro Ser Gln Glu Leu Phe Pro Leu Ser Glu
                        530                 535                 540

Gln Gln Lys Lys Ile Leu Ala Gln Val Glu Met Thr Asn Lys Met Gln
        545                 550                 555                 560

Thr Asp Asp Ile Pro Gly Thr Gln Lys Leu Phe Ser Lys Glu Trp Ile
                        565                 570                 575

Gln Lys Val Arg Ala Lys Lys Ile Ile Trp Ser Arg Asn Gln Thr Ile
                        580                 585                 590

Pro Ile His Thr Asp His Thr Val Arg Ile Pro Arg Trp Asp Glu Lys
                        595                 600                 605

Ile Lys Phe Pro Arg Tyr Lys Ser Glu Tyr Ile Leu Asn Asn Lys Ile
                        610                 615                 620

Asn Leu Thr Met Glu Gln Val Leu Arg Gln Tyr Asn Leu Leu Lys Glu
        625                 630                 635                 640

Val Glu Arg Tyr Asp Lys Asp Leu Lys Val Pro Lys Leu Leu Asp Ile
                        645                 650                 655

Leu Asp Lys Trp Phe Pro Val Gln Ser Ser Lys Ile Lys Thr Tyr Glu
                        660                 665                 670

Ser Gln Gly Phe His Arg Thr Asp Ala Ile Asn Leu Ala Val Gly Glu
                        675                 680                 685

Ile Pro Thr Glu Pro Ala Val Lys Ile Asn Pro Ile Leu Ile Asn Phe
                        690                 695                 700

Val Lys Leu His Leu Glu Arg Gln Gly Ile Arg His Gln Arg Gly Arg
        705                 710                 715                 720

Asn Lys Ile Ala Lys Phe Ile Tyr Gln Lys Gln Asn Lys Gln Arg Thr
                        725                 730                 735
```

<210> SEQ ID NO 71
<211> LENGTH: 749
<212> TYPE: PRT
<213> ORGANISM: Penaeid shrimp infectious myonecrosis virus

<400> SEQUENCE: 71

```
Met Asp Glu Ile Arg Asn Tyr Thr His Leu Asp Tyr Ile Phe Val Gln
1               5                   10                  15

Asn Ile Cys Ile Tyr Met Leu Val Phe Gly Ile Asp Thr Val Lys His
            20                  25                  30

Phe Arg Gln Ile Gly Leu Phe Asn Glu Arg Asn Glu Phe Ile Glu Ile
        35                  40                  45

Ala Lys Gln Leu Ser Thr Lys Gly Lys Arg Phe Val Asp Asp Val Asp
    50                  55                  60

Asn Met Lys Gln Lys Val Cys Glu Ile Ala Thr Ile Val Gly Tyr Met
65                  70                  75                  80

Asp Pro Asn Val Asp Lys Ile Asp Val Met Glu Glu Val Asn Ser Leu
                85                  90                  95

Ala Ala Glu Gly Asn Glu His Gly Ile Asp Arg Asp Asn Trp Asn Asp
            100                 105                 110

Leu Phe Thr Lys Thr Cys Lys Glu Val Met Thr Trp Tyr Lys Gly His
        115                 120                 125

Glu Phe Ile Ser Phe Asp Asp Tyr Ile Lys Glu Gly Met Trp Leu Thr
    130                 135                 140

Ser Gly Ser Ser Ile Gly Lys Val His Trp Thr Lys Asp Gly Glu
145                 150                 155                 160

Asn Gly Lys Phe Lys Ala Arg Lys Asn Met Leu Leu Gln Ile Tyr Thr
                165                 170                 175

Pro Gln Glu Leu Ala Asn Ile Val Tyr Ala Trp Asp Gly Lys Leu His
            180                 185                 190

Ser Arg Val Phe Ile Lys Asn Glu Met Ser Lys Leu Arg Leu Ala Val
        195                 200                 205

Ala Ser Asn Ile Glu Ala Tyr Ile His Glu Ser Tyr Met Leu Phe Leu
    210                 215                 220

Tyr Gly His Gly Phe Lys Glu Tyr Phe Gly Val Thr Leu Asp Glu Lys
225                 230                 235                 240

Pro Asp Gln Gln His Gln Arg Glu Ile Glu Met Ile Glu Lys Leu Gln
                245                 250                 255

Ala Gly Tyr Phe Gly Leu Pro Phe Asp Tyr Ala Ser Phe Asp His Gln
            260                 265                 270

Pro Thr Thr Phe Glu Val Lys Thr Met Val Arg Arg Val Gly Glu Ile
        275                 280                 285

Val Val Ser Gln Val Pro Lys Asn Tyr Tyr Gln Thr Gln Leu Leu
    290                 295                 300

Val Asn Lys Ile Val Asn Ala Tyr Asp Lys Ser Tyr Leu Ser Gly Asn
305                 310                 315                 320

Ile Lys Asn Thr Lys Phe Glu Asn Ile Lys Val Lys Gly Gly Val Pro
                325                 330                 335

Ser Gly Val Arg Ile Thr Ser Leu Leu Gly Asn Met Trp Asn Ala Ile
            340                 345                 350

Ile Thr Lys Ile Ala Ile Asn Asn Val Ile Gly Ile Gly Tyr Asp
        355                 360                 365

Pro Ile Ser Gln Ile Ser Leu Arg Gly Asp Asp Val Ala Ile Leu Ser
```

```
                    370                 375                 380
Lys Asp Pro Ala Ala Leu Tyr Leu Leu Arg Leu Ser Tyr Ala Ala Ile
385                 390                 395                 400

Asn Ala Ile Gly Lys Asp Ser Lys Leu Gly Ile Ser Pro Lys Val Cys
                405                 410                 415

Glu Phe Leu Arg Asn Glu Ile Ser Val Thr Gly Val Arg Gly Trp Thr
            420                 425                 430

Cys Arg Gly Ile Gly Gly Ile Ser Gln Arg Lys Pro Trp Asn Pro Gln
        435                 440                 445

Pro Trp Ser Pro Asn Asp Glu Val Glu Thr Asn Ala Ser Asn Ile Ser
    450                 455                 460

Leu Leu Glu Arg Arg Ala Gly Ile Glu Leu Gln Gln Leu His His Ile
465                 470                 475                 480

Asn Lys Val Lys Trp Ser Arg His Val Arg Gln Ser Tyr Lys Tyr Leu
                485                 490                 495

Glu Leu Pro Lys Arg Leu Gly Gly Phe Gly Ile Tyr Arg Phe Gln Gly
            500                 505                 510

Trp Leu Pro Asn Gly Lys Leu Pro Leu Ala Lys Lys Pro Leu Val Asn
        515                 520                 525

Val Glu Asp Ile His Pro Ser Gln Glu Leu Phe Leu Pro Leu Ser Glu
    530                 535                 540

Gln Gln Lys Lys Ile Leu Ala Gln Val Glu Met Thr Asn Lys Met Gln
545                 550                 555                 560

Thr Asp Asp Ile Pro Gly Thr Gln Lys Leu Phe Ser Lys Glu Trp Ile
                565                 570                 575

Gln Lys Val Arg Ala Lys Lys Ile Ile Trp Ser Arg Asn Gln Thr Ile
            580                 585                 590

Pro Ile His Thr Asp His Thr Val Arg Ile Pro Arg Trp Asp Glu Lys
        595                 600                 605

Ile Lys Phe Pro Arg Tyr Lys Ser Glu Tyr Ile Leu Asn Asn Lys Ile
    610                 615                 620

Asn Leu Thr Met Glu Gln Val Leu Arg Gln Tyr Asn Leu Leu Lys Glu
625                 630                 635                 640

Val Glu Arg Tyr Asp Lys Asp Leu Lys Val Pro Lys Leu Leu Asp Ile
                645                 650                 655

Leu Asp Lys Trp Phe Pro Val Gln Ser Ser Lys Ile Lys Thr Tyr Glu
            660                 665                 670

Ser Gln Gly Phe His Arg Thr Asp Ala Ile Asn Leu Ala Val Gly Glu
        675                 680                 685

Ile Pro Thr Glu Pro Ala Val Lys Ile Asn Pro Ile Leu Ile Asn Phe
    690                 695                 700

Val Lys Leu His Leu Glu Arg Gln Gly Ile Arg His Gln Arg Gly Arg
705                 710                 715                 720

Asn Lys Ile Ala Lys Phe Ile Tyr Gln Lys Thr Lys Gln Ala Glu Asn
                725                 730                 735

Met Ile Leu Gln Ser Ser Leu Gln Gln Met Tyr Arg Tyr
            740                 745

<210> SEQ ID NO 72
<211> LENGTH: 4818
<212> TYPE: DNA
<213> ORGANISM: Penaeid shrimp infectious myonecrosis virus

<400> SEQUENCE: 72
```

```
atggctataa acgaactagc cgttaaagtt ggaaagaagc ctaaatacac atcgacgaaa      60
accggagctg accacattcc aagctggact gtattggttg agttcgcagg ttttagcgaa     120
gcagcaacat gtgacacagt taaaaacgca aaaatgattg ctgcttacaa attagttaaa     180
agattttgta atgggaccca acctacatt gaaatttctg attgtatgct gccacctcca      240
gaccttacat cgtgcgggga cgttgagagt aatcctggac ctatcataca tagcgttgca     300
tttgcaagaa ctggttcagt atggacacct gccacctta ctttcaatac tacatcatcc      360
ccgggtagac tgcaagtaca aatgtcatcc agcgacaata gatatgggtt caattctgtt    420
ttacttgcag caggtggtac aacatggggc acagcttatt tttcacaacg ttggaacagt    480
gactttggat tacagccaga tctaactata actgtaacac cacaactaac tggagaagaa    540
cttggttcaa tttatttga tgctgttgaa actacaaatg cagaggaagc tatagaggca    600
acaattataa atactactcc aattgatgta atggtagaca acagcagg ccctgtacca      660
attgaaggtg atttcaaacc cacaaatgaa actcccacgt gggtaagtaa cacaaagccc     720
attgatgtag caacacctaa gactcgtgac tacgtaaatc ggtcagtact gactccacaa    780
ctgatcacaa aaatgaaaga ccatgtctat gccttacaaa aggatgaagt taaagatgta    840
acacttgcct cactcgattt cggcttaaat ccatcaagtg tactcggaag atggttgaaa    900
tggttaactg gcatagacat gagactccat cttgggaaga agtcacaaa ccataaagtt     960
agaatgtttg tgcaaaaaac aaggtttcca ctaaagacag caattgagga actaaacaat   1020
ggtactgttc cacgtagatt aaggagggat gttcgttaca ttgaaaagcc gttcgataaa    1080
gaggaacata ccgatatact gttatctggt gatgttgagg aaaaccccgg gcctgaaggg    1140
atggaacagg tatcaataac gccagaacaa cttcaaatga ttctggcaat gcaaaaatca   1200
ccaccaaagc caaagatcaa agaactaagt gaaagggaaa ttcagttaag gctccaagga   1260
aatgaagcaa cccgcagaca tcaaagattt aaaggtgagc ccattgatcc agttctaact    1320
agagaagata taattagaaa gcacaatcag cagaatggaa tattgcctga tgaaaaagaa    1380
cagccggtag tggtaaataa cgtacaccct ttggagaagg agtattccat tgaaaaggaa    1440
ggaatggtgt gggacgagga acaatttttg acgtatatac atgacaaatc atcaagcaac    1500
gatcactatg cctgcatcta taacgttgtt acacataaca gattcggtgt acttgaaatg    1560
ccagaagatc cacttgaaat gattgatcat tatgaaccag gggaagaacc aaaaacaaaa    1620
cctaaaacta aagtggtaa caaaagagaa ctaaatgatg aaacctttta cagaaagaag    1680
aagacaaaaa caacaaaaga gccaaaaaca caagagcaaa agaaaattga ccacgataac    1740
atgttttcac gattgctgag aaggcttgac aaaccacaaa ttgtagcagc ttggctaaac    1800
aacagaccat cacgtaaatt ggtcgaaaaa ttagctgaca gtaaattcgg aattggatgg    1860
caagcaaaag aagagtacac aaccagcatg gtaattgtat ctggatatat caattgtgaa    1920
ccattacccc taatcgtaga taagcttctc tccgtcgata caactatga catgtggcaa    1980
cagactgaca agtattttga caatttgatc acactgtgta accgcgtcag tgacgttacc    2040
tacactagcg ctcagctgtg tagagatgca tctatcttga ataacaagaa gatgcatgtt    2100
gaaaatggaa acattgtttc aatggaaaat cagtctgaaa ttgatagtca aactaaattc    2160
ttttcactgt tagaagatga taacaaactt ccaattgtag atgagctaag agtattagct    2220
gatatgacgg cacaaagaag caacgtaaac actgctggta atcatcttcg tgataatgac    2280
tctattaggg ccgacgctgt tctagctaac aatacagtac gtaacaattg tcaaattcca    2340
attcctgtaa caacactaat accaagacaa attcgtggat tgaatggtgt acttgtaaat    2400
```

```
cagcaattac ggttacaggg aattgaaaca cacattacag acagttatat ttcaaaagct    2460
gagccatctg actattcgaa acaactgtct gaaatggtta atgctcaaaa gacatcaact    2520
tggcgagcaa acaatatcgc atcacagggg tgggacatgt ttgatactgt acagttaaat    2580
acaaacatat cacaaaaaga tctttcaatg gacactgctt tgacaaagct tatgttgttg    2640
taccagctaa caacacaaaa tctgccagca acacaattac catcaagcat ttattctgca    2700
tttgattcaa gaacacagcc tactttacag gatggaattt ggggtataaa taatggtgtt    2760
aatatatttg gtgaacaatg cggtggatta gccgcgccag tctttccatt cagtgggggc    2820 accgagaaa ttactttcca tcttacttta caatctgttc cacaggaatt tcaagaatca     2880
gcaattttcg taccagcaac tgcactacaa gctgcaaaag agggtgctcg aacattggca    2940
atgtatgttt taatgtttgc agaatggcca tttggtatgt atacaaaaac taaacaaaca    3000
acagacaatg ctggtaataa tcaatcagat caaattttca ttcactccga atctactgta    3060
catattccag gacaaaaaca aatgcatatt gtgctgccaa gaaaagtgaa catggtgaac    3120
cccactacaa ttgcagaagc aaatgcacgt gtagtaattc aaccaacata cggtacagtg    3180
gcagctgggg caggtgtcgc aaatggtaat attaacgtag ctgctgttgg tgtggccctg    3240
ccaactgtaa atttgactga ctatcttgta tcctgggcaa ccgatttcac acttggcgac    3300
ataaaacaat tggttgaaag aatgaaaaca cactgccaa ttagtcgaga cttgatggca     3360
gcacgtcaaa atgctatgtt attgagtact ctatttcctc cactaattca gagcaatgtg    3420
gcttcagaca caaggaagt cccaggaaca gctggagcat acactgcatg tcttgcaaac     3480
ttaggtattc ctgaaacact aacagttaac tggggagtag atataaatgt tcagccattg    3540
tatcagctac ttgaaacgga catcacagcc acaatcggt acgtattaaa cctgttcaaa      3600
agagaagaag tggtagcagg tgcatatgaa tttgggtggt tgggacacat ggccagttat    3660
atgatgggac tccttctaac aatgaatata tcatcagtgt ttaacgtttg gtattcaaca    3720
agacgtattt caacaaaggc gtgggacaca gcatatgata gtaacatcca agcatatcag    3780
gacatgcatt atcaaatgtt ttcgtggagt tcaatgcaag gtagtattgc accagcaatg    3840
gtggacgaaa ttcttcataa cctttgtggc caaatgtttg ggttcagctt accattgaga    3900
caagtcttat ttaacgcatt gccaatcact ttttcatcgt ttggaagttg gatgttgcct    3960
agagtttctg atggtttcca aactgtaagg tattatgatg taggtccacc agtcattaat    4020
gcaaaacgtg atggggaagt accagtaagt atgattgacg catggaccta taaatttaca    4080
gaaaaattgc caaaaagttt tttgccatgg ccaatgccag aaggaaagga cagtacaatg    4140
ggatatgatc cggaaaaaga accagcacta attgataatt caaatgagac aggcaatgta    4200
ttcagaccat ttatggcaag aaatggcaac aattctaatt atttgccaac caactacaca    4260
attgacgtat cacagaatgg tcatgatgag agttgtatta atgttgacct ttttaacaat    4320
gttgcaggag taacactaac aaaattatgat ggaaccgcaa caaacgcaga cgtcgtacca    4380
acaggatcat atattaagca gagagcaatg cctatcaatg caaatgcggt acgaccaact    4440
gaaacactcg acgctgctaa ccatacaaaa cctttgcta ttgaaggagg aagactcgta    4500
tatttgggtg aacaattgc aaatacaacc aatgtgtaa acgcaatgca gaggaaacaa      4560 aggcttttcaa aaccggcatt caagtgggca catgctcaga caacgtgt atatgacagc     4620 agtcgtccag gatggacgc aatcacaaag ttgtgtgcac gaaagtcggg ttttatgaat     4680
gcccgttcca cagcaatgat ggcacccaag actggactca gcgctgttat agatcaagca    4740
```
ccaaatacat ctcaagactt gatcgaacag ccgagtcagc aagaggttat ggatatgcaa 4800
gcgacagcaa cagtataa 4818

<210> SEQ ID NO 73
<211> LENGTH: 2211
<212> TYPE: DNA
<213> ORGANISM: Penaeid shrimp infectious myonecrosis virus

<400> SEQUENCE: 73
atggacgaga ttcgtaatta cactcatcta gattatatct ttgtacaaaa catttgtatc 60
tatatgttag tatttggaat agacacagtt aaacacttta gacaaatagg tctattcaat 120
gaaaggaatg aatttattga aattgcaaaa cagttatcaa ccaaagggaa aagatttgtt 180
gatgatgttg ataatatgaa acaaaaggta tgtgaaatag ctactattgt tggttatatg 240
gacccaaatg ttgataaaat agacgtaatg gaagaagtca actcactcgc agctgaaggt 300
aatgaacatg gtatagatag agataattgg aatgatttgt ttacaaaaac atgcaaagaa 360
gtaatgacat ggtacaaagg acatgaattt attagttttg atgattacat aaaggaagga 420
atgtggttaa caagtggaag ttcaagtatt gggaaagtgc attggacaaa agatggagaa 480
aatgggaaat ttaaagcaag gaaaaatatg ctgttacaaa tttatacacc gcaagaattg 540
gccaacattg tttatgcttg ggatggaaag ttacattcac gtgtctttat taaaaacgaa 600
atgagtaaat taagacttgc tgtggcatct aacatcgaag catatattca tgaatcttat 660
atgcttttcc tatatggtca tggttttaaa gaatactttg gagtgacgct tgacgaaaaa 720
ccagatcaac agcatcagag agaaattgaa atgattgaga aactacaagc tggatacttt 780
ggattaccat ttgactatgc atcatttgat catcagccaa caactttcga agttaagaca 840
atggtgagaa gagttggaga aattgtagtt agtcaagtac ctaagaatta ttactatcag 900
acacaattgc tagtcaataa gattgttaat gcatatgata aaagttattt gtctggaaat 960
attaaaaata caaaatttga aaatataaaa gtcaaaggtg gagtaccatc aggagtgaga 1020
ataacgagtt tgttgggtaa tatgtggaac gctataatta caaagatcgc aataaataat 1080
gttattggaa ttattggata cgacccaatc tcccaaatct cgttacgcgg agacgacgtt 1140
gctatattaa gtaaagatcc agcagctctt tatttactta gactatcata tgctgcaatt 1200
aatgcaattg gcaaagatag taagttaggt atatctccaa aagtatgtga atttttacgg 1260
aatgagatat cagtgacagg agtacgcggt tggacatgta gaggaatagg tggcataagt 1320
caacgaaaac catggaatcc acaaccttgg agtccaaatg atgaagtcga aacaaatgca 1380
agcaacattt cattattaga aagacgagca ggaattgaac ttcaacaatt acaccacata 1440
aacaaagtta aatggtcgag acacgtcaga caaagttata aatatctaga attgccaaaa 1500
cgacttggtg gttttggaat ctatcgattc caggggtggt tacctaacgg caaattacca 1560
cttgccaaaa agcccttggt taacgtagag gacatacatc caagccaaga gctgtttttg 1620
cctttaagtg aacaacagaa aaagatctta gcacaggttg aaatgacaaa caaaatgcaa 1680
acagatgata tacctgggac acaaaaatta ttttcaaagg aatggataca gaaagtgcgt 1740
gcaaaaaaga tcatatggag tagaaatcag acaataccaa tccatactga tcacacagta 1800
cgtataccaa gatgggacga gaaaatcaaa ttcccaaggt ataaatcaga atatatatta 1860
aataataaaa tcaacttaac aatggagcaa gtgctaagac agtataacct cctaaaagaa 1920
gtggaacggt acgataaaga tctaaaagtg ccaaagttat tagacatttt ggacaaatgg 1980
ttcccggtcc aaagtagtaa aattaaaaca tatgaaagtc aaggttttca tagaacagac 2040

```
gcaattaacc ttgctgttgg tgaaattcca actgaaccag cagttaaaat aaatcctata    2100
ctaataaact ttgtcaagtt acatcttgaa agacaaggta ttagacatca gagaggtaga    2160
aataagatcg ccaaatttat ttaccaaaaa caaaacaagc agagaacatg a             2211
```

<210> SEQ ID NO 74
<211> LENGTH: 280
<212> TYPE: DNA
<213> ORGANISM: Penaeid shrimp infectious myonecrosis virus

<400> SEQUENCE: 74

```
atggctataa acgaactagc cgttaaagtt ggaaagaagc ctaaatacac atcgacgaaa      60
accggagctg accacattcc aagctggact gtattggttg agttcgcagg ttttagcgaa     120
gcagcaacat gtgacacagt taaaaacgca aaaatgattg ctgcttacaa attagttaaa     180
agattttgta atgggaccc aacctacatt gaaatttctg attgtatgct gccacctcca      240
gaccttacat cgtgcgggga cgttgagagt aatcctggac                           280
```

<210> SEQ ID NO 75
<211> LENGTH: 852
<212> TYPE: DNA
<213> ORGANISM: Penaeid shrimp infectious myonecrosis virus

<400> SEQUENCE: 75

```
cctatcatac atagcgttgc atttgcaaga actggttcag tatggacacc tgccacctttt    60 actttcaata ctacatcatc cccgggtaga ctgcaagtac aaatgtcatc cagcgacaat    120
agatatgggt tcaattctgt tttacttgca gcaggtggta acatggggg cacagcttat    180 ttttcacaac gttggaacag tgactttgga ttacagccag atctaactat aactgtaaca    240
ccacaactaa ctggagaaga acttggttca atttattttg atgctgttga aactacaaat    300
gcagaggaag ctatagaggc aacaattata aatactactc caattgatgt aatggtagac    360
acaacagcag gccctgtacc aattgaaggt gatttcaaac ccacaaatga aactcccacg    420
tgggtaagta acacaaagcc cattgatgta gcaacaccta agactcgtga ctacgtaaat    480
cggtcagtac tgactccaca actgatcaca aaaatgaaag accatgtcta tgccttacaa    540
aaggatgaag ttaaagatgt aacacttgcc tcactcgatt tcggcttaaa tccatcaagt    600
gtactcggaa gatggttgaa atggttaact ggcatagaca tgagactcca tcttgggaag    660
aaagtcacaa accataaagt tagaatgttt gtgcaaaaaa caaggttttcc actaaagaca    720 gcaattgagg aactaaacaa tggtactgtt ccacgtagat taaggaggga tgttcgttac    780
attgaaaagc cgttcgataa agaggaacat accgatatac tgttatctgg tgatgttgag    840
gaaaaccccg gg                                                         852
```

<210> SEQ ID NO 76
<211> LENGTH: 981
<212> TYPE: DNA
<213> ORGANISM: Penaeid shrimp infectious myonecrosis virus

<400> SEQUENCE: 76

```
cctgaaggga tggaacaggt atcaataacg ccagaacaac ttcaaatgat tctggcaatg     60
caaaaatcac caccaaagcc aaagatcaaa gaactaagtg aaagggaaat tcagttaagg    120
ctccaaggaa atgaagcaac ccgcagacat caaagattta aggtgagcc cattgatcca    180 gttctaacta gagaagatat aattagaaag cacaatcagc agaatggaat attgcctgat    240
```

```
gaaaaagaac agccggtagt ggtaaataac gtacaccctt tggagaagga gtattccatt    300
gaaaaggaag gaatggtgtg ggacgaggaa caatttttga cgtatataca tgacaaatca    360
tcaagcaacg atcactatgc ctgcatctat aacgttgtta cacataacag attcggtgta    420
cttgaaatgc cagaagatcc acttgaaatg attgatcatt atgaaccagg ggaagaacca    480
aaaacaaaac ctaaaactaa aagtggtaac aaaagagaac taaatgatga aacctttac     540
agaaagaaga agacaaaaac aacaaaagag ccaaaaacac aagagcaaaa gaaaattgac    600
cacgataaca tgttttcacg attgctgaga aggcttgaca aaccacaaat tgtagcagct    660
tggctaaaca acagaccatc acgtaaattg gtcgaaaaat tagctgacag taaattcgga    720
attggatggc aagcaaaaga agagtacaca accagcatgg taattgtatc tggatatatc    780
aattgtgaac cattacccct aatcgtagat aagcttctct ccgtcgataa caactatgac    840
atgtggcaac agactgacaa gtattttgac aatttgatca cactgtgtaa ccgcgtcagt    900
gacgttacct acactagcgc tcagctgtgt agagatgcat ctatcttgaa taacaagaag    960
atgcatgttg aaaatggaaa c                                              981
```

```
<210> SEQ ID NO 77
<211> LENGTH: 2727
<212> TYPE: DNA
<213> ORGANISM: Penaeid shrimp infectious myonecrosis virus

<400> SEQUENCE: 77
atgcatgttg aaaatggaaa cattgtttca atggaaaatc agtctgaaat tgatagtcaa     60
actaaattct tttcactgtt agaagatgat aacaaacttc caattgtaga tgagctaaga    120
gtattagctg atatgacggc acaaagaagc aacgtaaaca ctgctggtaa tcatcttcgt    180
gataatgact ctattagggc cgacgctgtt ctagctaaca atacagtacg taacaattgt    240
caaattccaa ttcctgtaac aacactaata ccaagacaaa ttcgtggatt gaatggtgta    300
cttgtaaatc agcaattacg gttacaggga attgaaacac acattacaga cagttatatt    360
tcaaaagctg agccatctga ctattcgaaa caactgtctg aaatggttaa tgctcaaaag    420
acatcaactt ggcgagcaaa caatatcgca tcacaggggt gggacatgtt tgatactgta    480
cagttaaata caaacatatc acaaaaagat ctttcaatgg acactgcttt gacaaagctt    540
atgttgttgt accagctaac aacacaaaat ctgccagcaa cacaattacc atcaagcatt    600
tattctgcat ttgattcaag aacacagcct actttacagg atggaatttg ggggtataaat   660
aatggtgtta atatatttgg tgaacaatgc ggtggattag ccgcgccagt ctttccattc    720
agtgggggca ccggagaaat tactttccat cttactttac aatctgttcc acaggaattt    780
caagaatcag caattttcgt accagcaact gcactacaag ctgcaaaaga gggtgctcga    840
acattggcaa tgtatgtttt aatgtttgca gaatggccat ttggtatgta tacaaaaact    900
aaacaaacaa cagacaatgc tggtaataat caatcagatc aaattttcat tcactccgaa    960
tctactgtac atattccagg acaaaaacaa atgcatattg tgctgccaag aaaagtgaac   1020
atggtgaacc ccactacaat tgcagaagca aatgcacgtg tagtaattca accaacatac   1080
ggtacagtgg cagctggggc aggtgtcgca aatggtaata ttaacgtagc tgctgttggt   1140
gtggccctgc caactgtaaa tttgactgac tatcttgtat cctgggcaac cgatttcaca   1200
cttggcgaca taaaacaatt ggttgaaaga atgaaaacaa cactgccaat tagtcgagac   1260
ttgatggcag cacgtcaaaa tgctatgtta ttgagtactc tatttcctcc actaattcag   1320
agcaatgtgg cttcagacac aaaggaagtc ccaggaacag ctggagcata cactgcatgt   1380
```

```
cttgcaaact taggtattcc tgaaacacta acagttaact ggggagtaga tataaatgtt    1440
cagccattgt atcagctact tgaaacggac atcacagccc acaatcggta cgtattaaac    1500
ctgttcaaaa gagaagaagt ggtagcaggt gcatatgaat ttgggtggtt gggacacatg    1560
gccagttata tgatgggact ccttctaaca atgaatatat catcagtgtt taacgtttgg    1620
tattcaacaa gacgtatttc aacaaaggcg tgggacacag catatgatag taacatccaa    1680
gcatatcagg acatgcatta tcaaatgttt tcgtggagtt caatgcaagg tagtattgca    1740
ccagcaatgg tggacgaaat tcttcataac ctttgtggcc aaatgtttgg gttcagctta    1800
ccattgagac aagtcttatt taacgcattg ccaatcactt tttcatcgtt tggaagttgg    1860
atgttgccta gagtttctga tggttttcaa actgtaaggt attatgatgt aggtccacca    1920
gtcattaatg caaacgtga tggggaagta ccagtaagta tgattgacgc atggacctat    1980
aaatttacag aaaaattgcc aaaaagtttt ttgccatggc caatgccaga aggaaaggac    2040
agtacaatgg gatatgatcc ggaaaaagaa ccagcactaa ttgataattc aaatgagaca    2100
ggcaatgtat tcagaccatt tatggcaaga atggcaaca attctaatta tttgccaacc    2160
aactacacaa ttgacgtatc acagaatggt catgatgaga gttgtattaa tgttgaccctt   2220
```
(Note: line at 2220 contains "aactacacaa ttgacgtatc acagaatggt catgatgaga gttgtattaa tgttgaccttt")

```
tttaacaatg ttgcaggagt aacactaaca aattatgatg gaaccgcaac aaacgcagac    2280
gtcgtaccaa caggatcata tattaagcag agagcaatgc ctatcaatgc aaatgcggta    2340
cgaccaactg aaacactcga cgctgctaac catacaaaac cttttgctat tgaaggagga    2400
agactcgtat atttgggtgg aacaattgca aatacaacca atgtggtaaa cgcaatgcag    2460
aggaaacaaa ggctttcaaa accggcattc aagtgggcac atgctcagag acaacgtgta    2520
tatgacagca gtcgtccagg gatggacgca atcacaaagt tgtgtgcacg aaagtcgggt    2580
tttatgaatg cccgttccac agcaatgatg gcacccaaga ctggactcag cgctgttata    2640
gatcaagcac caaatacatc tcaagacttg atcgaacagc cgagtcagca agaggttatg    2700
gatatgcaag cgacagcaac agtataa                                        2727
```

<210> SEQ ID NO 78
<211> LENGTH: 2211
<212> TYPE: DNA
<213> ORGANISM: Penaeid shrimp infectious myonecrosis virus

<400> SEQUENCE: 78

```
atggacgaga ttcgtaatta cactcatcta gattatatct ttgtacaaaa catttgtatc      60
tatatgttag tatttggaat agacacagtt aaacacttta gacaaatagg tctattcaat     120
gaaaggaatg aatttattga aattgcaaaa cagttatcaa ccaaagggaa aagatttgtt     180
gatgatgttg ataatatgaa acaaaaggta tgtgaaatag ctactattgt tggttatatg     240
gacccaaatg ttgataaaat agacgtaatg gaagaagtca actcactcgc agctgaaggt     300
aatgaacatg gtatagatag agataattgg aatgatttgt ttacaaaaac atgcaaagaa     360
gtaatgacat ggtacaaagg acatgaattt attagttttg atgattacat aaaggaagga     420
atgtggttaa caagtggaag ttcaagtatt gggaaagtgc attggacaaa agatggagaa     480
aatgggaaat ttaaagcaag gaaaaatatg ctgttcaaaa tttatacacc gcaagaattg     540
gccaacattg tttatgcttg ggatggaaag ttacattcac gtgtctttat taaaaacgaa     600
atgagtaaat taagacttgc tgtggcatct aacatcgaag catatattca tgaatcttat     660
atgcttttcc tatatggtca tggttttaaa gaatactttg gagtgacgct tgacgaaaaa     720
```

```
ccagatcaac agcatcagag agaaattgaa atgattgaga aactacaagc tggatacttt      780
ggattaccat ttgactatgc atcatttgat catcagccaa caactttcga agttaagaca      840
atggtgagaa gagttggaga aattgtagtt agtcaagtac ctaagaatta ttactatcag      900
acacaattgc tagtcaataa gattgttaat gcatatgata aaagttattt gtctggaaat      960
attaaaaata caaatttgaa aatataaaa gtcaaggtg gagtaccatc aggagtgaga       1020
ataacgagtt tgttgggtaa tatgtggaac gctataatta caaagatcgc aataaataat     1080
gttattggaa ttattggata cgacccaatc tcccaaatct cgttacgcgg agacgacgtt     1140
gctatattaa gtaaagatcc agcagctctt tatttactta gactatcata tgctgcaatt     1200
aatgcaattg gcaaagatag taagttaggt atatctccaa agtatgtga atttttacgg     1260
aatgagatat cagtgacagg agtacgcggt tggacatgta gaggaatagg tggcataagt     1320
caacgaaaac catggaatcc acaaccttgg agtccaaatg atgaagtcga aacaaatgca     1380
agcaacattt cattattaga aagacgagca ggaattgaac ttcaacaatt acaccacata     1440
aacaaagtta aatggtcgag acacgtcaga caaagttata aatatctaga attgccaaaa     1500
cgacttggtg gttttggaat ctatcgattc caggggtggt tacctaacgg caaattacca     1560
cttgccaaaa agcccttggt taacgtagag gacatacatc caagccaaga gctgtttttg     1620
cctttaagtg aacaacagaa aaagatctta gcacaggttg aaatgacaaa caaatgcaa      1680
acagatgata tacctgggac acaaaaatta ttttcaaagg aatggataca gaaagtgcgt     1740
gcaaaaaaga tcatatggag tagaaatcag acaataccaa tccatactga tcacacagta     1800
cgtataccaa gatgggacga gaaaatcaaa ttcccaaggt ataaatcaga atatatatta     1860
aataataaaa tcaacttaac aatggagcaa gtgctaagac agtataaccct cctaaaagaa     1920
gtggaacggt acgataaaga tctaaaagtg ccaaagttat tagacattt ggacaaatgg      1980
ttcccggtcc aaagtagtaa aattaaaaca tatgaaagtc aaggtttca tagaacagac     2040
gcaattaacc ttgctgttgg tgaaattcca actgaaccag cagttaaaat aaatcctata     2100
ctaataaaact ttgtcaagtt acatcttgaa agacaaggta ttagacatca gagaggtaga    2160
aataagatcg ccaaatttat ttaccaaaaa caaaacaagc agagaacatg a              2211
```

<210> SEQ ID NO 79
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79

```
taatacgact cactataggg aaaaccggag ctgaccacat tcca                        44
```

<210> SEQ ID NO 80
<211> LENGTH: 380
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80

```
agaaagtttg tttcgtagag cgagaaaaac agaatccact tatggctata aacgaactag       60
ccgttaaagt tggagagaag cctaaataca catcgacgaa aaccggagct gaccacattc      120
caagctggac tgtattggtt gagttcgcag gttttagcga agcagcgaca tgtgacacag      180
```

```
ttaaaaacgc aaaaatgatt gctgcttaca aattagttaa aagatttgt aaatgggacc      240 caacctacat tgaaatttct gattgtatgc tgccacctcc agaccttaca tcgtgcgggg     300
acgttgagag taatcctgga cctatcatac atagcgttgc atttgcaaga actggttcag    360
tatggacacc tgccaccttt                                                 380
```

<210> SEQ ID NO 81
<211> LENGTH: 281
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

```
aaaccggagc tgaccacatt ccaagctgga ctgtattggt tgagttcgca ggttttagcg      60
aagcagcgac atgtgacaca gttaaaaacg caaaaatgat tgctgcttac aaattagtta    120
aaagattttg taaatgggac ccaacctaca ttgaaatttc tgattgtatg ctgccacctc    180
cagaccttac atcgtgcggg gacgttgaga gtaatcctgg acctatcata catagcgttg    240
catttgcaag aactggttca gtatggacac tgccaccttt t                        281
```

<210> SEQ ID NO 82
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82

```
ctggactgta ttggttgagt tcgcaggttt tagcgaagca gcgacatgtg acacagt        57
```

<210> SEQ ID NO 83
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83

```
aaaccggagc tgaccacatt ccaagctgga ctgtattggt tgagttcgca ggttttagcg      60
aagcagcgac atgtgacaca gt                                              82
```

<210> SEQ ID NO 84
<211> LENGTH: 154
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84

```
actgtattgg ttgagttcgc aggttttagc gaagcagcga catgtgacac agttaaaaac      60
gcaaaaatga ttgctgctta caaattagtt aaaagatttt gtaaatggga cccaacctac    120
attgaaattt ctgattgtat gctgccacct ccag                                154
```

<210> SEQ ID NO 85
<211> LENGTH: 871
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 85

```
tcaactcact cgcatctgaa ggtaatgaac atggtataga tagagataat tggaatgatt        60
tgtttacaaa aacatgcaaa gaagtaatga catggtacaa aggacatgaa tttattagtt       120
ttgatgatta cataaaggaa ggaatgtggt taacaagtgg aagttcaagt attgggaaag       180
tgcattggac aaaagatgga gaaaatggga aatttaaagc aaggaaaaat atgctgttac       240
aaatttatac accgcaagaa ttggccaaca ttgtttatgc ttgggatgga aagttacatt       300
cacgtgtctt tattaaaaac gaaatgagta aattaagact tgctgtcgca tctaacatcg       360
aagcatatat tcatgaatct tatatgcttt tcctatatgg tcatggtttt aaggaacact       420
ttggagtgac gcttgatgaa aaaccagatc aacagcatca gagagaaatt gaaatgattg       480
agaaactaca agctggatac tttggattac catttgacta tgcatcattt gatcatcagc       540
caacaacttt tgaagttaag acaatggtga gaagagttgg agaaattgta gttagtcaag       600
tacctaagaa ttattactat cagacacaat tgctagtcaa taagattgtt aatgcatatg       660
ataaaagtta tttgtctgga aatattaaaa atacaaaatt tgaaaatata aaagtcaaag       720
gtggagtacc atcaggagtg agaataacga gtttgttggg taatatgtgg aacgctataa       780
ttacaaagat cgcaataaat aatgttattg gaattattgg atacgaccca atctcccaaa       840
tctcgttacg cggagacgac gttgctatat t                                     871
```

METHODS AND COMPOSITIONS TO PROTECT AQUATIC INVERTEBRATES FROM DISEASE

RELATED APPLICATIONS

This application claims priority to previously filed and provisional application U.S. Ser. No. 61/407,297, filed Oct. 27, 2010; to previously filed and provisional application U.S. Ser. No. 61/418,433, filed Dec. 1, 2010; to previously filed and application U.S. Ser. No. 61/449,940 filed Mar. 7, 2011; to previously filed and application U.S. Ser. No. 61/484,255 filed May 10, 2011; to previously filed and application U.S. Ser. No. 61/508,172 filed Jul. 15, 2011; and to previously filed and application U.S. Ser. No. 61/525,332 filed Aug. 19, 2011, the contents of each of which are incorporated herein by reference in their entirety.

STATEMENT REGARDING FEDERALLY SPONSORED RESEARCH OR DEVELOPMENT

This invention was made with Government support awarded by The U.S. Department of Agriculture, National Institute of Food and Agriculture SBIR under contract 2010-33610-20936. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Oct. 4, 2011 and amended Aug. 30, 2012, is named 150004.txt and is 107,592 bytes in size.

BACKGROUND OF THE INVENTION

Aquaculture has become one of the fastest growing segments of food animal production in the world. This precipitous increase is being driven by decreasing stocks within wild fisheries and increasing demand for seafood throughout the United States, Europe, and Japan. Disease in aquatic invertebrates is a serious problem for the industry.

For example, one of the fastest growing areas of demand is imported farm raised shrimp. According to FAO data, the last twenty years has seen farmed aquatic and in particular farmed shrimp production of *Litopenaeus vannamei*, commonly the Pacific White Shrimp or the Pacific Whiteleg Shrimp, rise from 8000 metric tons in 1980 to 1,380,000 metric tons produced in 2004 Fisheries and Aquaculture Department. FishStatPlus—Fishery Statistical software 2009 (www.fao.org/fishery/statistics/software/fishstat/en.) Most of this dramatic increase can be accounted for by increases in production throughout Asia as they began to intensively culture *Litopenaeus vannamei* in lieu of the native *Penaeus monodon*, the black tiger shrimp, for export to the United States, specifically countries such as China, Thailand, Indonesia, and Vietnam. Fishery Statistical software 2009, supra. Following the introduction of *Litopenaeus vannamei* into Asia as a domesticated species, it became dominant, where in 2004 it accounted for half the shrimp produced globally. (Lightner, D. V., 2005. Biosecurity in shrimp farming: pathogen exclusion through use of SPF stock and routine surveillance. Journal of the World Aquaculture Society 36, 229-248.)

As *L. vannamei* began to dominate cultivation abroad, so did domestic demand in the United States. Shrimp imports rose from $1.6 billion to $3.7 billion from 1990-2004 (USDA Foreign Agriculture Service, 2005, US Seafood Imports Continue to Soar. International Trade Reports. Aug. 8, 2005. Jul. 28, 2010) representing 34 percent of total seafood imports and 25 percent of total seafood consumption in 2004, respectively. As of 2004, 70% of the United States seafood was imported with 40% of it being farm-raised, mostly cultured in southeast Asia. Rapidly increasing production of *L. vannamei* has outgrown demand, and led to price depression in international markets, mostly in the United States and European Union. Farm value for 15-20 g size Pacific White shrimp has steadily decreased from $5 US to about $3 in 2005. (Fisheries and Aquaculture Department, 2009, supra).

As farm raised production continues to increase in market share in comparison to wild stocks, so does the impact of disease on shrimp farming. Producers have adopted practices such as higher stocking densities, smaller inland pond culture, and higher feeding rates to increase competitiveness. This has led to an increasing vulnerability to infectious disease, specifically viral pathogens followed by secondary bacterial infections. Viral diseases such as White Spot Syndrome Virus (WSSV) have become pandemic and resulted in worldwide losses in the billions of dollars. For example, WSSV was first discovered in 1992 after several outbreaks of a high mortality disease occurred in shrimp farms in Taiwan (Chou, H.-Y., Huang, C.-Y., Wang, C.-H., Chiang, H.-C., Lo, C.-F., 1995. Pathogenicity of a baculovirus infection causing white spot syndrome in cultured penaeid shrimp in Taiwan. Diseases of Aquatic Organisms 23, 165-173.) It is estimated that Asia alone has lost over $6 billion since 1992, and the Americas $1-2 billion since WSSV was introduced in 1999 (Lightner 2003 The penaeid shrimp viral pandemics due to IHHNV, WSSV, TSV and YHV: history in the Americas and current status, Proceedings of the 32nd Joint UJNR Aquaculture Panel Symposium, Davis and Santa Barbara, Calif., USA, pp. 17-20.) In another example, Ecuador experienced dramatic losses, a 65% percent loss in production was observed after the introduction of WSSV and this accounted for, in lost exports alone, over a half billion US dollars. In addition, 130,000 jobs were lost and over 100,000 hectares of ponds were abandoned. (McClennen, C. White Spot Syndrome Virus, The Economic, Environmental and Technical Implications on the Development of Latin American Shrimp Farming. Master of Arts in Law and Diplomacy Thesis. 2004.) Similarly, Peru experienced a precipitous drop in production to one tenth in 2000 of production in 1998 with 85% of shrimp ponds being abandoned, and $9 million in losses in feed costs alone. (McClennen, 2004, supra.) In China, it was estimated that 80% of total production losses annually were attributed to WSSV. (Zhan, W.-B., Wang, Y.-H., 1998. White Spot Syndrome Virus Infection of Cultured Shrimp in China. Journal of Aquatic Animal Health 10, 405-410.0

Currently there are no commercially available vaccines, therapeutics, or interventions for these pathogens causing devastating economic losses to aquatic invertebrates and in particular in shrimp producing countries.

All references cited are incorporated herein by reference in their entirety. Examples are provided by way of illustration and not intended to limit the scope of the invention.

SUMMARY

Vaccines and compositions are described in which aquatic invertebrates are protection from adverse impact of a microorganism causing disease. A protective molecule, which may be a nucleic acid molecule of the microorganism, a polypeptide encoded, an interfering RNA such as dsRNA or antisense RNA, or DNA encoding same or replicon vectors comprising or producing any of the above are provided in a vaccine. Such molecules protect the animal from disease. Methods of administration and preparation are also described.

BRIEF DESCRIPTION OF THE DRAWINGS

FIG. 19A is a graph showing results of Example 4, Experiment 3. Shrimp were injected with 0.02 µg of dsRNA #3, 5' truncate of dsRNA3, or a 5' truncate of dsRNA3 and challenged 10 days following administration. N=3 groups of 10 shrimp per treatment.

SUMMARY

Figure 1A:
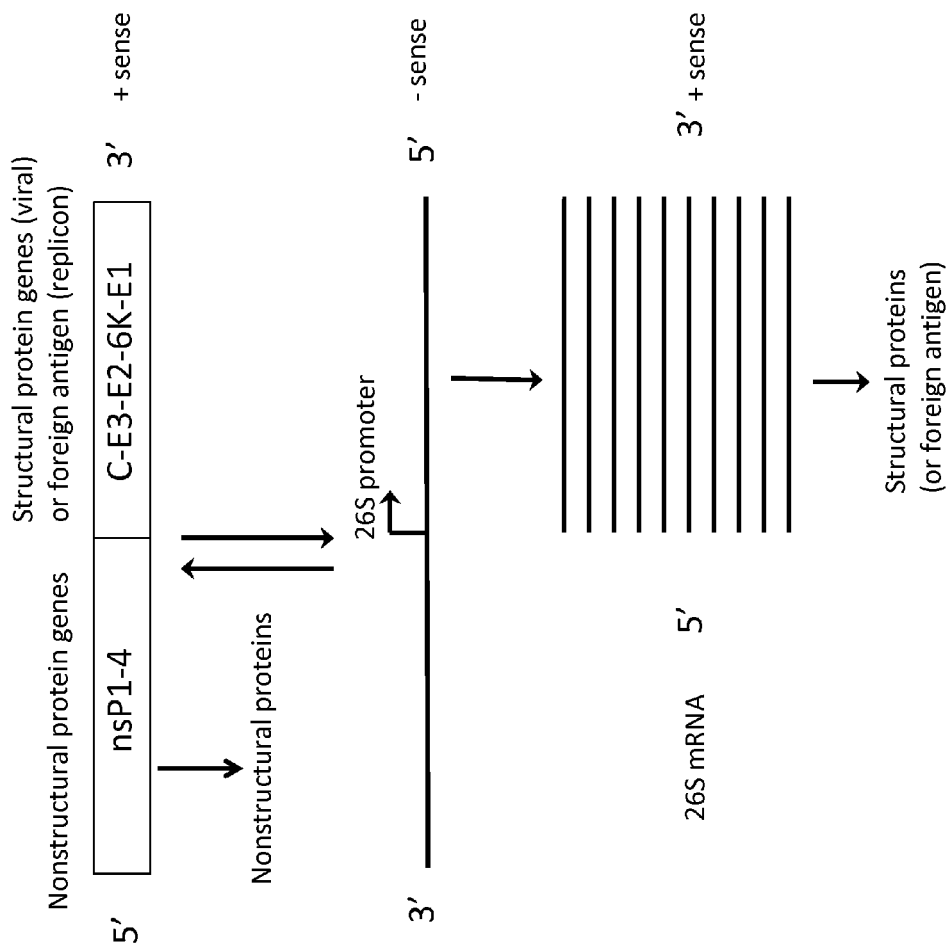
FIG. 1A is a schematic representation of VEE genome organization and replication strategy and FIG. 1B is a schematic of the VEE replicon particle vaccine and packaging system.

Methods of producing compositions used to protect aquatic invertebretes from disease are disclosed. A protective molecule is produced by identifying a target nucleic acid molecule of a microorganism causing disease, there interference of which protects the animal from the disease, and preparing a dsRNA molecule, an antisense RNA molecule or DNA producing same or a replicon particle comprising the same. When administered to the animal, it is protected form the disease. Nucleic acid molecules of WSSV VP19 and VP28 which protect animals from the disease are disclosed.

Also disclosed are antisense and dsRNA molecules which protect the animal from disease. Vaccines and compositions are also disclosed.

DESCRIPTION

Provided here is a method of protecting aquatic invertebrates, and in particular, shrimp, from disease. In an embodiment a delivery system is provided of specific nucleic acid molecules that can induce a protective and/or immune response in the invertebrate to the pathogen.

The examples provided here show use of the invention with shrimp, and it is considered to be particularly useful in protecting shrimp (as in the class Malacostraca which includes Decapods including Dendrobranchiates such as prawns and Carideans such as shrimp) from disease or disorders. However, other invertebrates and in particular aquatic invertebrates, freshwater and marine, are expected to benefit from protection from disease and disorder provided by the invention including, by way of example without limitation, crustacean (e.g. lobsters, crabs, shrimp, crayfish), mollusks (e.g., squid, clams, octopus, snails, abalone, mussels), Porifera (sponges), Cnidaria (e.g., jellyfish, sea anemones), Ctenophora, Echinodermata and aquatic worms. The invention is particularly useful in aquatic invertebrates having commercial value, and especially useful with farmed aquatic invertebrates (as opposed to those living in the wild at sea), as explained herein. As shown herein, it is possible to deliver the nucleic acid molecules and/or polypeptides or fragments thereof of the invention to the digestive tract of the animal (which can be found after administration throughout the digestive tract or a portion thereof), whether by immersion, oral delivery or the like. This greatly aids the delivery of a vaccine to the animal, as opposed to methods such as injection, and provides a practical and effective means of vaccinating the animals, especially with mass vaccination of a multitude of animals.

The methods of the invention include means of interference with expression of a nucleic acid molecule of the disease-causing agent or nucleic acid molecule of the disease-causing agent. When referring to interference with expression, it is meant that expression of the nucleic acid molecule is inhibited, disrupted, or otherwise interfered with such that the animal is protected from the disease. In one embodiment, the method uses an antisense RNA that is complimentary to a nucleic acid molecule of the disease-causing agent (target nucleic acid molecule). Antisense RNA is RNA that is complementary to a target, usually a messenger RNA (mRNA) of a target nucleic acid molecule. By antisense is intended a sequence that is in inverse orientation to the 5'-to-3' normal orientation of the target nucleic acid molecule. When delivered into a cell, expression of the antisense RNA sequence prevents normal expression of the protein encoded by the targeted nucleic acid molecule. When referring to RNA being a complement is meant to include that the polynucleotide for use in antisense suppression may correspond to all or part of the complement of the sequence encoding the target polypeptide, all or part of the complement of the 5' and/or 3' untranslated region of the target polypeptide transcript, or all or part of the complement of both the coding sequence and the untranslated regions of a transcript encoding the target polypeptide. A complementary nucleic acid molecule is that which is complementary to an mRNA transcript of all or part of a target nucleic acid molecule. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same cell. Furthermore, portions of the antisense nucleotides may be used to disrupt the expression of the target nucleic acid molecule. Generally, antisense sequences of at least 10 nucleotides, 20 nucleotides, 50 nucleotides, 100 nucleotides, 200 nucleotides, 300, 500, 550, 500, 550, or greater and any amount in-between may be used. The sequence may be complementary to any sequence of the messenger RNA, that is, it may be proximal to the 5'-terminus or capping site, downstream from the capping site, between the capping site and the initiation codon and may cover all or only a portion of the non-coding region, may bridge the non-coding and coding region, be complementary to all or part of the coding region, complementary to the 3'-terminus of the coding region, or complementary to the 3'-untranslated region of the mRNA. The antisense sequence may be complementary to a unique sequence or a repeated sequence, so as to enhance the probability of binding. Thus, the antisense sequence may be involved with the binding of a unique sequence, a single unit of a repetitive sequence or of a plurality of units of a repetitive sequence. Methods of preparing antisense nucleic acid molecules are known. See, e.g. Shewmaker et al, U.S. Pat. No. 5,759,829, incorporated herein by reference.

In another embodiment of the invention, RNA interference is used and in a preferred embodiment double-stranded RNA molecules (dsRNA) are employed. In this process, in summary, RNA which is double stranded, in part, or completely, is produced based upon the sequence of the target nucleic acid molecule. Specifics of the means of producing the dsRNA may vary as one skilled in the art appreciates, and include, by way of example without intending to be limiting, the approach of Graham et al., U.S. Pat. No. 6,573,099 where two copies of a sequence corresponding to a target sequence is used, or that of Fire et al., U.S. Pat. No. 6,326,193, where the first strand is an RNA sequence corresponding to the target nucleic acid, and the second is one which is complementary to the target sequence, each of which are incorporated herein by reference in their entirety. These strands hybridize with each other to form the inhibiting dsRNA. The strand which corresponds to the target nucleic acid molecule can correspond to all or a portion thereof, so long as a dsRNA is formed. Where a strand is used which is the complement (antisense) of the target nucleic acid is used, it can be complementary to all or a portion of the target nucleic acid molecule, so long as the dsRNA formed interferes with the target nucleic acid molecule. The dsRNA triggers a response in which the RNAse III Dicer enzyme process dsRNA into small interfering RNAs (siRNA) of approximately 21-23 nucleotides, which are formed into a RNA-induced silencing complex RISC which destroys homologous mRNAs. (See, Hammond, S. M., et al., Nature (2000) 404:293-296). When referring to a target nucleic acid molecule it is meant a nucleic acid molecule or fragment thereof of the disease agent, the expression of which is interfered with. Generally, sequences of at least 10 nucleotides 20 nucleotides, 30 nucleotides, 40 nucleotides, 50 nucleotides, 100 nucleotides, 200 nucleotides, 300, 500, 550, 500, 550, or greater and any amount in-between may be used.

The inventors have shown examples of dsRNA sequences which can be used in the invention, and have discovered that fragments of such dsRNA can be used to provide a protective response. For example, dsRNA #3 that interferes with IMNV and provides a protective response is a 380 base pair sequence. However, fragments of the dsRNA provide a protective response. Thus when referring to dsRNA of the invention, fragments of the dsRNA that provide such a protective response are included.

As discussed below, the inventors have also demonstrated that a nucleic acid molecule encoding a polypeptide or fragment thereof of the disease-causing agent may be administered to the aquatic invertebrate animal and a protective response observed.

In an embodiment, Replicon Particle technology is used to deliver the protective molecule to the animal. The nucleic acid molecule, polypeptide encoded, or fragments of the nucleic acid molecule or polypeptide, or the antisense or dsRNA are those which produce a protective response when administered to the animal and are referred to herein at times as the protective molecule. The protective molecule is introduced into a cell by any of the various means available to one skilled in the art, whether by uptake, absorption, through cellulase processes, or auxiliary agents or devices, injection or the like, examples of which are described below.

In one embodiment the vaccine of the invention comprises the protective molecule. In another embodiment the vaccine is made by producing the dsRNA which can then be introduced directly into the aquatic invertebrate animal cell, or placed in a vector or expression cassette and introduced into the cell. The inventors have discovered that the dsRNA can be introduced directly into the cell and a protective response is produced. The dsRNA could be delivered by a DNA vector that then produces the dsRNA from a promoter that is recognized by some cellular DNA-dependant RNA polymerase. In another embodiment, Replicon Particle technology may be employed in producing the vaccine. Where the antisense RNA is used as a vaccine, without wishing to be bound by any theory, it is believed it then forms a dsRNA in the cell into which it is introduced.

Prior to introducing the protective molecule, one identifies a nucleic acid sequence in the disease-causing agent which is to be expressed or inhibited (target nucleic acid molecule or target gene). The protective molecules may either express, inhibit, or compete for binding sites with any such target nucleic acid molecule which, when administered, results in protection to the animal from the disease causing agent. Any such protective molecule may be employed in the invention. Examples, without intending to be limiting of such protective molecules are those encoding or inhibiting White Spot Syndrome Virus (WSSV) or fragments thereof, and in a preferred embodiment, encoding or inhibiting VP28, and VP19 polypeptides of WSSV or fragments thereof, or Infectious Myonecrosis Virus (IMNV) or fragments thereof and which stimulate a protective response. The inventors have also shown in one embodiment that a Replicon Particle expressing VP19 antisense and VP19 protein provides protection. Further, fragments of dsRNAs of target molecules are shown here to also provide protection.

Once that genetic information is obtained, a nucleic acid molecule or an antisense or dsRNA of such target nucleic acid molecule is provided as a vaccine.

In one embodiment, the "naked" nucleic acid molecules or naked dsRNA or antisense molecule may be administered to the aquatic animal, that is the dsRNA or antisense need not be provided in a conventional expression cassette or vector. Such a molecule may be produced by any convenient method, such as primer amplification and reverse transcription such as is described below.

In another embodiment, the protective molecule may be delivered by an expression cassette or vector which may optionally include other components. In a further embodiment, the protective molecule may be delivered by Replicon Particle. In yet another embodiment, delivery of the vaccine to the digestive tract of the animal provides protection.

A "vector" is any means for the transfer of a nucleic acid into a host cell. A vector may be a replicon to which a DNA segment may be attached so as to bring about the replication of the attached segment. A "replicon" is any genetic element (e.g., plasmid, phage, cosmid, chromosome, virus) that functions as an autonomous unit of DNA or RNA replication in vivo, i.e., capable of replication under its own control. The term "vector" includes both viral and nonviral means for introducing the nucleic acid into a cell in vitro, ex vivo or in vivo. Viral vectors include alphavirus, retrovirus, adeno-associated virus, pox, baculovirus, vaccinia, herpes simplex, Epstein-Barr and adenovirus vectors. Non-viral vectors include, but are not limited to plasmids, liposomes, electrically charged lipids (cytofectins), DNA- or RNA protein complexes, and biopolymers. In addition to a nucleic acid, a vector may also contain one or more regulatory regions, and/or selectable markers useful in selecting, measuring, and monitoring nucleic acid transfer results (transfer to which tissues, duration of expression, etc.).

A "cassette" refers to a segment of DNA that can be inserted into a vector at specific restriction sites. The segment of DNA encodes a polypeptide of interest or produces RNA, and the cassette and restriction sites are designed to ensure insertion of the cassette in the proper reading frame for transcription and translation.

A nucleic acid molecule is introduced into a cell when it is inserted in the cell. A cell has been "transfected" by exogenous or heterologous DNA or RNA when such DNA or RNA has been introduced inside the cell.

A cell has been "transformed" by exogenous or heterologous DNA when the transfected DNA effects a phenotypic change. The transforming DNA can be integrated (covalently linked) into chromosomal DNA making up the genome of the cell.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent substitutions" or "silent variations," which are one species of "conservatively modified variations." Every polynucleotide sequence described herein which encodes a polypeptide also describes every possible silent variation, except where otherwise noted. Thus, silent substitutions are an implied feature of every nucleic acid sequence which encodes an amino acid. One of skill will recognize that each codon in a nucleic acid (except AUG, which is ordinarily the only codon for methionine) can be modified to yield a functionally identical molecule by standard techniques. In some embodiments, the nucleotide sequences that encode a protective polypeptide are preferably optimized for expression in a particular host cell (e.g., yeast, mammalian, plant, fungal, and the like) used to produce the polypeptide or RNA.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" referred to herein as a "variant" where the alteration results in the substitution of an amino acid with a chemically similar amino acid. Conservative substitution tables providing functionally similar amino acids are well known in the art. See, for example, Davis et al., "Basic Methods in Molecular Biology" Appleton & Lange, Norwalk, Conn. (1994). Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, 1984, Proteins).

The isolated variant proteins can be purified from cells that naturally express it, purified from cells that have been altered to express it (recombinant), or synthesized using known protein synthesis methods. For example, a nucleic acid molecule encoding the variant polypeptide is cloned into an expression vector, the expression vector introduced into a host cell and the variant protein expressed in the host cell. The variant protein can then be isolated from the cells by an appropriate purification scheme using standard protein purification techniques.

A protein is comprised of an amino acid sequence when the amino acid sequence is at least part of the final amino acid sequence of the protein. In such a fashion, the protein may be a the original polypeptide, a variant polypeptide and/or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids.

The variant proteins used in the present invention can be attached to heterologous sequences to form chimeric or fusion proteins. Such chimeric and fusion proteins comprise a variant protein fused in-frame to a heterologous protein having an amino acid sequence not substantially homologous to the variant protein. The heterologous protein can be fused to the N-terminus or C-terminus of the variant protein.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A variant protein-encoding nucleic acid can be cloned into such an expression vector such that the fusion moiety is linked in-frame to the variant protein.

Polypeptides sometimes contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art. Accordingly, the variant peptides of the present invention also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cros slinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

The present invention further provides fragments of the variant proteins of the present invention, in addition to proteins and peptides that comprise and consist of such fragments, provided that such fragments act as an antigen and/or provide treatment for and/or protection against infections as provided by the present invention.

The phrase "biological sample" refers to a fluid or tissue of an animal. Such components are known in the art and include, without limitation, blood, plasma, serum, and secretions of the intestinal or genitourinary tracts.

As used herein, an antibody is defined in terms consistent with that recognized within the art: they are multi-subunit proteins produced by an organism in response to an antigen challenge. The antibodies used with the present invention include monoclonal antibodies and polyclonal antibodies, as well as fragments of such antibodies, including, but not limited to, Fab or F(ab')hd 2, and Fv fragments.

As used herein, the term "subunit" refers to a portion of the microorganism which may itself antigenic, i.e., capable of inducing an immune response in an animal or protective. The term should be construed to include subunits which are obtained by both recombinant and biochemical methods.

As used herein, the term "isolate" refers to a virus obtained from a specific source. Isolate is used interchangeably with the term "strain".

As used herein, the term "vaccine" as used herein refers to a pharmaceutical composition comprising at least one protective molecule, nucleic acid or polypeptide or fragment thereof that induces an immunological and/or protective response in an animal and possibly, but not necessarily, one or more additional components that enhance the activity of said active component. A vaccine may additionally comprise further components typical to pharmaceutical compositions. In another form, the immunologically active component of a vaccine may comprise appropriate elements of said organisms (subunit vaccines) whereby these elements are generated either by destroying the whole organism or the growth cultures of such microorganisms and subsequent purification steps yielding in the desired structure(s), or by synthetic processes induced by an appropriate manipulation of a suitable system such as, but not restricted to, bacteria, insects, mammalian, or other species, plus subsequent isolation and purification procedures or by induction of said synthetic processes in the animal needing a vaccine by direct incorporation of genetic material using suitable pharmaceutical compositions (polynucleotide vaccination). A vaccine may comprise one or simultaneously more than one of the elements described above.

The terms "protecting", "protection", "protective immunity" or "protective immune response," as used herein, are intended to mean that the host animal mounts an active immune response to the vaccine or polypeptides of the present invention, such that upon exposure to the disease challenge, the animal is able to combat the infection. Thus, a protective immune response will decrease the incidence of morbidity and mortality from exposure to the microorganism among a host animal. The animal will be protected from subsequent exposure to the disease-causing agent. In an embodiment, the animal may be protected by treating the animal which has already been exposed to the disease-causing agent by administration of the vaccine or polypeptide after such exposure. In such an instance there is also shown to be a lessening of morbidity and mortality. Those skilled in the art will understand that in a commercial animal setting, the production of a protective immune response may be assessed by evaluating the effects of vaccination on a pond, group, flock or herd as a whole, e.g., there may still be morbidity and mortality in a minority of vaccinated animals. Furthermore, protection also includes a lessening in severity of any gross or histopathological changes and/or of symptoms of the disease, as compared to those changes or symptoms typically caused by the isolate in similar animals which are unprotected (i.e., relative to an appropriate control). Thus, a protective immune response will decrease the symptoms of the disease, which will vary according to the disease. Those skilled in the art will also understand that in the case of an arthropod host, protective immunity does not necessarily equate to the traditional memory response characteristic of adaptive immunity in vertebrate animals. Disease morbidity and/or mortality is reduced and where there also may be a reduced titer of infection upon exposure to the microorganism.

As used herein, "immunogenically effective amount" refers to an amount, which is effective in reducing, eliminating, treating, preventing or controlling the symptoms of the infections, diseases, disorders, or condition.

In one embodiment, the present invention relates to a polypeptide comprising a polypeptide or fragment thereof of microorganism. The present inventors contemplate that the polypeptide may be a homologue, a derivative, or a variant of the polypeptide, or an immunologically active or a functional fragment thereof. The polypeptide may be isolated, synthesized, or recombinantly expressed using the polypeptide-encoding nucleic acids described herein.

The present invention also provides isolated and/or recombinant nucleic acids that encode a polypeptide or RNA of the invention. In addition, it should be understood based on the general state of the art that other equivalent sequences to the nucleotide or amino acid sequences of the polypeptides are covered by the present invention. For example, some deletions, insertions and substitutions in the amino acid sequence isolated from the microorganism or expressed by a nucleic acid sequence isolated from the microorganism are covered by the present invention, unless such mutation abolishes the ability of the polypeptide to induce the generation of protective response.

Nucleic acids of the invention include those that encode an entire polypeptide or produce an RNA sequence as well as those that encode a subsequence of the polypeptide or RNA or produce a fragment of a dsRNA. For example, the invention includes nucleic acids that encode a polypeptide or RNA which is not full-length but nonetheless has protective activity against infection. The invention includes not only nucleic acids that include the nucleotide sequences as set forth herein, but also nucleic acids that are substantially identical to, correspond to, or substantially complementary to, the exemplified embodiments. For example, the invention includes nucleic acids that include a nucleotide sequence that is at least about 70% identical to one that is set forth herein, more preferably at least 75%, still more preferably at least 80%, more preferably at least 85%, 86%, 87%, 88%, 89% still more preferably at least 90%, 91%, 92%, 93%, 94%, and even more preferably at least about 95%, 96%, 97%, 98%, 99%, 100% identical (or any percentage in between) to an exemplified nucleotide sequence. The nucleotide sequence may be modified as described previously, so long any polypeptide encoded or RNA or dsRNA produced is capable of inducing the generation of a protective response.

The inventors have shown that dsRNA sequences produced can include truncated fragments. Such fragments can be 9 or more base pairs, can be 10 base pairs, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 72, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000 base pairs or more or any number in-between, as long as a protective response is seen when administered to an animal. According to an embodiment of the invention, without wishing to be bound by any theory, at least nine bases are used to provide for sequence specificity such that interference with the target molecule occurs. A well-described mechanism of action for RNA interference (RNAi) is described for cellular microRNAs (miRNA) that is related to the action noted for the dsRNAs described above. The 5'-most seven to 8 nucleotides of a miRNA (sometimes referred to as the seed sequence) are involved in Watson-Crick base pairing with nucleotides in the 3' untranslated region of the target mRNA. (Lewis, B. P., C. B. Burge, and D. P. Bartel. 2005. Conserved seed pairing, often flanked by adenosines, indicates that thousands of human genes are miRNA targets *Cell* 120:15-20.) RNA-induced silencing complex (RISC) cleaves target mRNA where base pairing is perfect, and where imperfect, the target mRNA is translationally inactive, and protein expression is impacted without degrading mRNA. (Bartel, D. P. 2004. MicroRNAs: genomics, biogenesis, mechanism, and function. Cell. 116: 281-97.) It is likely that the same RISC-based activity is the mechanism by which the dsRNA described above are providing protection to shrimp. In a preferred embodiment, at least 20 bases are used, and in another preferred embodiment at least 30 bases are used, which further aids in transport into the cells. In another further preferred embodiment, higher efficacy is achieved with a dsRNA that is at least 50 bp or more in length.

To test such fragments, a process employment AEM (antiviral effector molecule) development is one of many available methods. According to successes in AEM development for IMNV, this process generally proceeds as follows: a long target region for AEM development is determined, protection from disease measured according to survival post challenge with the established disease challenge model, shorter length dsRNAs will be assessed in standard disease bioassays (described by way of example in Examples 1, 2 and 3 below) by designing dsRNAs to progressively shorter target regions within the proven, longer length AEM.

For each target of interest, in an example, a set of PCR primers with 5' T7 promoter sequence is designed to produce ~400 bp portions of the amplicon sequence AS. Amplicon sequence that is encompassed by the PCR primers are filtered by screening against the genome and transcriptome sequences to predict and minimize potential off-target effects. PCR products are generated from whole body cDNA derived from pooled larval and adult RNA. From this product, dsRNAs are produced using the Ambion Mega script in vitro transcription kit and yields 50-100 µg of high quality dsRNA per reaction. Typically, dsRNA yields of 50-100 ug are achieved from a single in vitro transcription reaction. It should be noted that the entire process of generating dsRNA production, from generating gene specific primers with 5' T7 promoter sequence, to product is usually 3 days (including primer synthesis and O/N shipping). Heterologous dsRNA to eGFP is used to control for the physiologic impact of triggering a dsRNA response. This process is repeated with successively truncated regions of proven targets. Gene suppression is measured by any available method, including quantitative RT-PCR or RT-PCR, nucleic acid hybridization or Northern blotting of whole body or specific tissues RNA extracts, using primer sets that extend beyond or are completely removed from the region encompassed by the dsRNA generating primer set.

The nucleic acids that encode a polypeptide or produce an RNA providing a protective response can be obtained using methods that are known to those of skill in the art. Suitable nucleic acids (e.g., cDNA, genomic, or subsequences) can be cloned, or amplified by in vitro methods such as the polymerase chain reaction (PCR) using suitable primers, the ligase chain reaction (LCR), the transcription-based amplification system (TAS), the self-sustained sequence replication system (SSR). A wide variety of cloning and in vitro amplification methodologies are well-known to persons of skill Examples of these techniques and instructions sufficient to direct persons of skill through many cloning exercises are found in Berger and Kimmel, Guide to Molecular Cloning Techniques, Methods in Enzymology 152 Academic Press, Inc., San Diego, Calif. (Berger); Sambrook et al. (2001) *Molecular Cloning—A Laboratory Manual* (Third ed.) Vol. 1-3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Amheim & Levinson (Oct. 1, 1990) C&EN 36-47; *The Journal Of NIH Research* (1991) 3: 81-94; (Kwoh et al. (1989) Proc. Natl. Acad. Sci. USA 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117. Improved methods of cloning in vitro amplified nucleic acids are described in Wallace et al., U.S. Pat. No. 5,426,039. Nucleic acids that encode the polypeptide or RNA of the invention, or subsequences of these nucleic acids, can be prepared by any suitable method as described above, including, for example, cloning and restriction of appropriate sequences.

"Codon optimization" can be used to optimize sequences for expression in an animal and is defined as modifying a nucleic acid sequence for enhanced expression in the cells of the aquatic animal of interest, e.g. shrimp, by replacing at least one, more than one, or a significant number, of codons of the native sequence with codons that are more frequently or most frequently used in the genes of that invertebrate. Various species exhibit particular bias for certain codons of a particular amino acid.

In one aspect, the present invention relates to polynucleotides comprising nucleic acid fragments of codon-optimized coding regions which encode polypeptides or produce RNA, or fragments, variants, or derivatives thereof, with the codon usage adapted for optimized expression in the cells of a given aquatic animal. These are prepared by incorporating codons preferred for use in the genes of the animal of interest into the DNA sequence. Also provided are constructs, vectors, and host cells comprising nucleic acid fragments of codon-optimized coding regions, and fragments, variants, or derivatives thereof, and various methods of using the polynucleotide expression constructs, vectors, host cells to treat or prevent disease in an animal.

A nucleic acid encoding a polypeptide or producing RNA may then be introduced into either a prokaryotic or eukaryotic host cell through the use of a vector, plasmid or construct and the like to produce the polypeptide. A typical expression cassette contains a promoter operably linked to a nucleic acid that encodes the product of interest. The expression cassettes are typically included on expression vectors that are introduced into suitable host cells, including for example, bacterial, insect, fungal, plant or animal cells. Either constitutive or regulated promoters can be used in the present invention. Promoters suitable for use in eukaryotic host cells are well known to those of skill in the art. The expression vectors of the invention can be transferred into the chosen host cell by methods known to those of ordinary skill in the art including, for example, calcium phosphate transfection, DEAE-dextran mediated transfection, transfection, microinjection, cationic lipid-mediated transfection, electroporation, transduction, scrape loading, ballistic introduction, infection or other methods. (See Molecule Cloning: A Laboratory Manual, 2d Ed. Vol. 1-3, ed. Sambrook et al., Cold Spring Harbor Laboratory Press (1989)). Transformed cells can be selected, for example, by resistance to antibiotics conferred by genes contained on the plasmids, such as the amp, gpt, neo and hyg genes.

In an example, the protective molecule may be expressed by a recombinant vector, viral vector, or virus. In another aspect, the recombinant vector, viral vector, or microorganism expressing the protective molecule may itself serve as a vaccine component acting as a as an protective agent or an adjuvant and eliciting or enhancing the protective response. By way of example, suitable recombinant virus vectors include but are not limited to live adenovirus, poxvirus, baculovirus, pseudorabies virus (PRV), Venezuelan equine encephalitis (VEE) vectors such as strains V3526 or TC-83, and viral replicon particles (VRPs) derived from VEE, equine arteritis virus (EAV), or transmissible gastroenteritis virus (TGE). The techniques employed to insert such a sequence into the viral vector and make ether alterations in the viral DNA, e.g., to insert linker sequences and the like, are known to one of skill in the art. (See, e.g., Molecular Cloning. A Laboratory Manual, supra.)

The nucleic acid molecule may be operably linked to a suitable promoter at the 5' end of the cDNA encoding a polypeptide or producing RNA and a termination signal and poly(A) signal at the 3' end of the cDNA. As used herein, the term "operably linked" means that the nucleic acid molecule containing an expression control sequence, e.g., transcription promoter and termination sequences, are situated in a vector or cell such that expression of the polypeptide or RNA produced by the nucleic acid molecule is regulated by the expression control sequence. Methods for cloning and operably linking such sequences are well known in the art. Examples of promoters suitable for expressing the antigen include but are not limited to are the cytomegalovirus immediate-early (CMV) promoter, the Rous sarcoma virus long terminal repeat (RSV-LTR) promoter, the simian virus 40 (SV40) immediate-early promoter, and inducible promoters such as the metallothionein promoter. Other examples of promoters include, T7 phage promoter, T3 phage promoter, beta-galactosidase promoter, and the Sp6 phage promoter. An example of a DNA having a termination and poly(A) signal is the SV40 late poly(A) region. Another example of a viral expression system suitable for producing the antigen is the Sindbis Expression system available from Invitrogen. The use of these commercially available expression vectors and systems are well known in the art.

The vaccine of the present invention may also contain multiple copies of one protective molecule or a combination of protective molecules.

In another embodiment, replicon particle (RP) vaccines are prepared. The RP vector has numerous advantages for vaccine development including accurate production of native proteins, tropism for lymphoid cells, lack of viral replication and transmission, induction of mucosal and systemic immunity, sequential immunization potential, and lack of preexisting immunity to VEE in animals although they clearly can respond to the virus immunologically. (Dickerman R W, Baker G J, Ordonez J V, Cherer W F (1973), Venezuelan Equine Encephalomyelitis Viremia and Antibody Responses of Pigs and Cattle, *American Journal of Veterinary Research* 34: 357-361.)

The replication strategy of VEE is similar to that of other alphaviruses. (Strauss J, Strauss E (1994), The alphaviruses: gene expression, replication, and evolution, *Microbiol Rev* 58: 491-562.) From positive-sense genomic RNA, four non-structural proteins (nsP1-nsP4) are translated and function to replicate a full-length negative-sense RNA. The negative-sense RNA serves as a template for replication of additional genomic RNA, and for synthesis of a subgenomic messenger RNA (26S mRNA), produced in 10-fold molar excess compared to genomic RNA, which directs the synthesis of the VEE structural proteins. The structural proteins are translated initially as a polyprotein that is co-translationally and post-translationally cleaved to release the capsid (C) protein and the two mature envelope glycoproteins (E1 and E2). Since VEE is a positive-sense RNA virus, full-length cDNA clones of VEE can be used to generate RNA transcripts that, when introduced into susceptible cells, will initiate a complete virus replication cycle and generate infectious virus. (Davis N L, Willis L V, Smith J F, Johnston R E (1989), In vitro synthesis of infectious Venezuelan equine encephalitis virus RNA from a cDNA clone: analysis of a viable deletion mutant, *Virology* 171: 189-204.)

Using site-directed mutagenesis of the DNA plasmid, VEE viruses can be generated containing mutations in the envelope glycoproteins that result in attenuated phenotypes. When inoculated into animals, such attenuated variants of VEE do not cause illness or significant viremia but are able to induce protective immunity against subsequent virulent VEE challenge in mice, horses and primates. (Davis N, Powell N, Greenwald G, Willis L, Johnson B, Smith J, Johnston R (1991), Attenuating mutations in the E2 glycoprotein gene of Venezuelan equine encephalitis virus: construction of single and multiple mutants in a full-length cDNA clone, *Virology* 183: 20-31; Grieder F, Davis N, Aronson J, Charles P, Sellon D, Suzuki K, Johnston R (1995), Specific restrictions in the progression of Venezuelan equine encephalitis virus-induced disease resulting from single amino acid changes in the glycoproteins, *Virology* 206: 994-1006.)

Similarly, foreign genes can be inserted in place of the VEE structural protein gene region in the cDNA plasmid, and an RNA transcript from such a plasmid, when introduced into cells, will replicate and express the heterologous genes. This self-amplifying replicon RNA will direct the synthesis of large amounts of the foreign gene product within the cell, typically reaching levels of 15-20% of total cell protein. (Pushko P, Parker M, Ludwig G V, Davis N, Johnston R E, Smith J F (1997), Replicon-Helper Systems from Attenuated Venezuelan Equine Encephalitis Virus: Expression of Heterologous Genes in Vitro and Immunization against Heterologous Pathogens in Vivo, *Journal of Virology* 239: 389-401.)

Figure 1B:
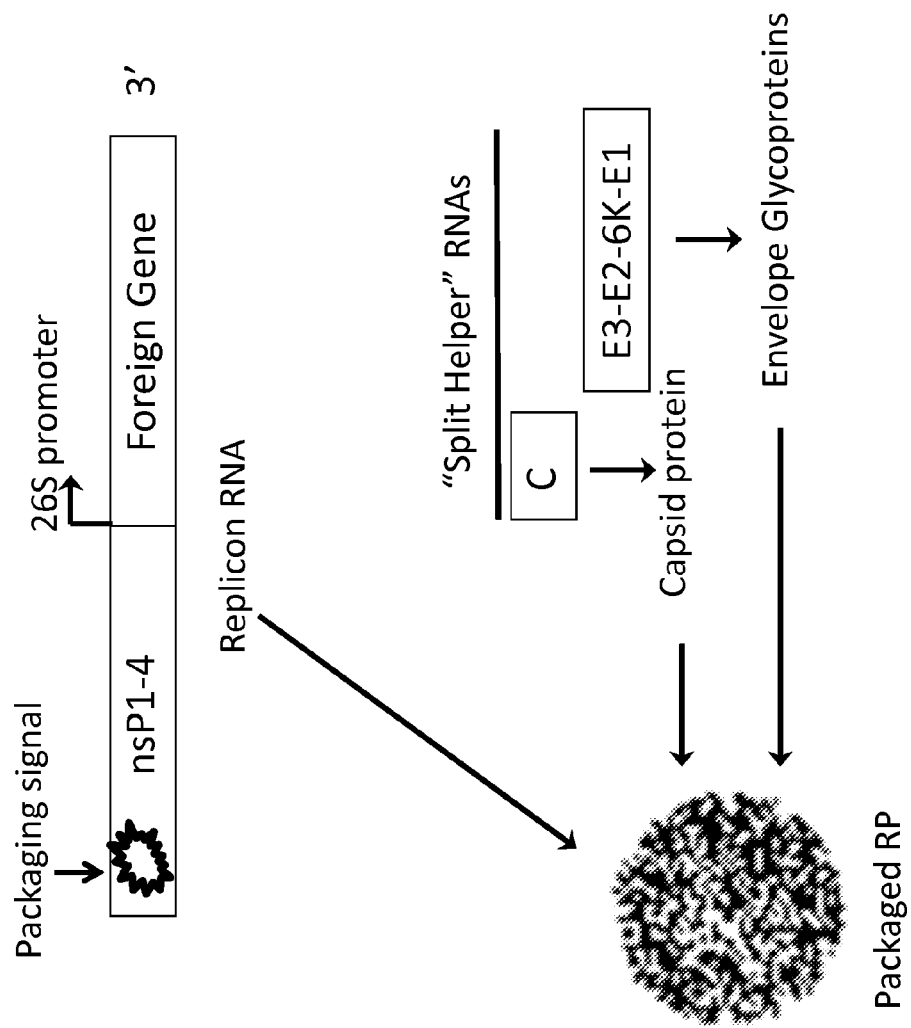
Figure 6:
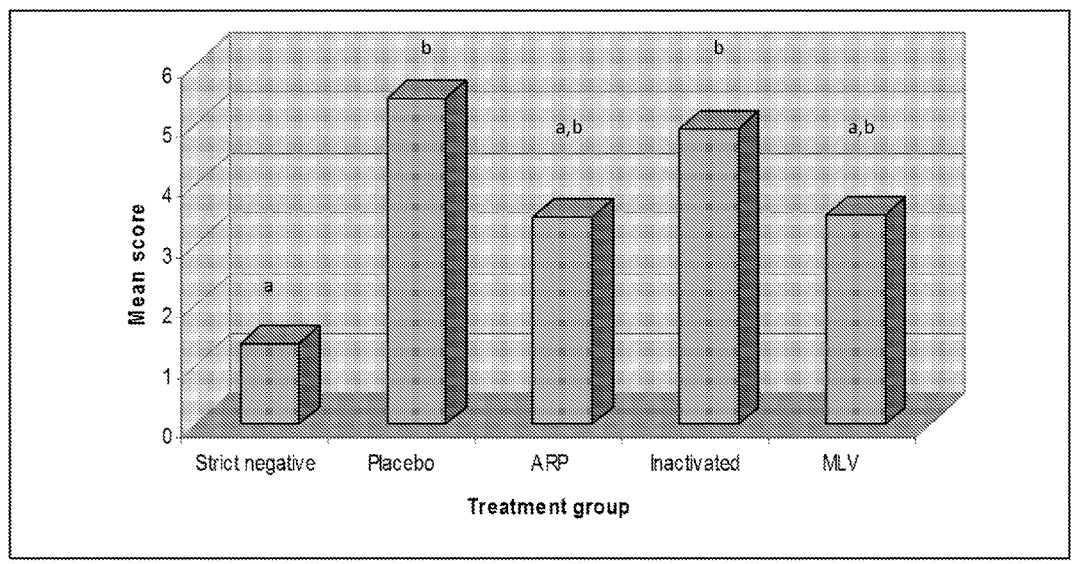
FIG. 6 is a graph showing a summary of lung lymphoid hyperplasia scores. Treatment groups with different letters are significantly different (ANOVA, $p<0.05$).

Because the replicon RNA does not contain the structural genes for VEE, it is a single-cycle, propagation-defective RNA and replicates only within the cell into which it is introduced. The replicon RNA can be packaged into RP by supplying the structural protein genes of VEE in trans (FIGS. 1A and 1B). Replicon RNA is packaged into RP when cells are co-transfected with replicon RNA and two separate helper RNAs, which together encode the full complement of VEE structural proteins. Pushko, supra. Importantly, only the replicon RNA is packaged into VRP, as the helper RNAs lack the packaging sequence required for encapsidation. Thus, the RP are propagation-defective, in that they can infect target cells in culture or in vivo, can express the foreign gene to high levels, but they lack critical portions of the VEE genome (i.e., the VEE structural protein genes) necessary to produce virus particles which could spread to other cells. The "split helper" system greatly reduces the chance of an intact genome being regenerated by RNA-RNA recombination and the possibility of functional recombination with helper RNAs was further reduced by removal of the 26S promoter from helper RNAs altogether (Kamrud et al 2010 Development and Characterization of Promoterless Helper RNAs for Production of Alphavirus Replicon Particles. Journal of General Virology. 91:pp. 1723-1727.). As an independent and additional layer of safety; attenuating mutations have been incorporated in the glycoprotein helper (Pushko et al 1997 *Journal of Virology* 239:389-401). FIG. 6 shows the VEE replicon particle vaccine and packaging system process. Expression of the nucleic acid molecule of interest can be varied up or down by introducing spacer elements upstream of the IRES/NOI cassette but downstream of the 26S promoter. (Kamrud et al. 2007, "Alphavirus Replicon Approach to Promoterless Analysis of IRES Elements", Virology 360(2), pp. 376-387) Also, where the gene of interest produces a potentially toxic protein, introducing a phosphoramidite morpholino oligomers at the same time the replicon and helper RNAs are electroporated into cells shuts down expression. The PMO blocks translation of the gene of interest during packaging of RP.

The methods and variations of same used to produce such replicons are known to one skilled in the art. Illustrative methodology can be found at U.S. Pat. No. 6,156,558, incorporated herein by reference in its entirety, and also at U.S. Pat. Nos. 6,521,235; 6,531,135; and U.S. Pat. Nos. 7,442,381; 6,541,010; 7,045,335; and 5,792,462 all of which are incorporated herein by reference in their entirety.

Alphavirus vectors and alphavirus replicon particles are used in embodiments of the invention. The term "alphavirus" has its conventional meaning in the art, and includes the various species of alphaviruses which are members of the Togaviridae family. This includes alphaviruses such as Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, South African Arbovirus No. 86, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus, and Buggy Creek virus. The viral genome is a single-stranded, messenger-sense RNA, modified at the 5'-end with a methylated cap, and at the 3'-end with a variable-length poly (A) tract. Structural subunits containing a single viral protein, C, associate with the RNA genome in an icosahedral nucleocapsid. In the virion, the capsid is surrounded by a lipid envelope covered with a regular array of transmembranal protein spikes, each of which consists of a heterodimeric complex of two glycoproteins, E1 and E2. See Pedersen et al., J. Virol. 14:40 (1974). The Sindbis and Semliki Forest viruses are considered the prototypical alphaviruses, and have been studied extensively. See Schlesinger The Togaviridae and Flaviviridae, Plenum Publishing Corp., New York (1986). The VEE virus has also been studied. See U.S. Pat. No. 5,185,440 to Davis et al.

As the above patents illustrate, preparation of replicon subunits by using alphavirus replicon vectors to obtain polypeptides and using alphavirus replicon particles to produce protective molecules are processes known to one skilled in the art. There are many modification to the process available, and any process using a replicon subunit or replicon particle methodology can be used with the invention. In a certain embodiment an alphavirus replicon RNA vector that expresses the gene of interest in a host cell and the expressed product is harvested. In another embodiment a replicon RNA comprising the gene of interest is introduced into a cell along with two helper RNAs coding for the alphavirus capsid protein and for the glycoproteins. The replicon RNA is packaged into a Replicon Particle. This Replicon Particle can be the protective molecule.

Thus the system in one embodiment provides for infectious, defective, alphavirus particles, wherein each particle comprises an alphavirus replicon RNA, and wherein the replicon RNA comprises an alphavirus packaging signal, one or more heterologous RNA sequence(s), and a sequence encoding at least one alphavirus structural protein, and wherein the replicon RNA furthermore lacks a sequence encoding at least one alphavirus structural protein; wherein the population contains no detectable replication-competent alphavirus particles as determined by passage on permissive cells in culture. For example, in U.S. Pat. No. 6,531,135, incorporated herein by reference in its entirety is shown in an embodiment an RP system which uses a helper cell for expressing an infectious, replication defective, alphavirus particle in an alphavirus-permissive cell. The helper cell includes (a) a first helper RNA encoding (i) at least one alphavirus structural protein, and (ii) not encoding at least one alphavirus structural protein; and (b) a second helper RNA separate from the first helper RNA, the second helper RNA (i) not encoding at least one alphavirus structural protein encoded by the first helper RNA, and (ii) encoding at least one alphavirus structural protein not encoded by the first helper RNA, such that all of the alphavirus structural proteins assemble together into alphavirus particles in the cell. Preferably, the alphavirus packaging segment is deleted from at least the first helper RNA.

There are many variations that are available to one skilled in the art when preparing such replicons. For example, in another embodiment described in the patent, the helper cell also includes a replicon RNA, which encodes the alphavirus packaging segment and an inserted heterologous RNA. In the embodiment wherein the helper cell also includes a replicon RNA, the alphavirus packaging segment may be, and preferably is, deleted from both the first helper RNA and the second helper RNA. For example, in the embodiment wherein the helper cell includes a replicon RNA encoding the alphavirus packaging segment and an inserted heterologous RNA, the first helper RNA includes the alphavirus E1 glycoprotein and the alphavirus E2 glycoprotein, and the second helper RNA includes the alphavirus capsid protein. The replicon RNA, first helper RNA, and second helper RNA in an embodiment are all on separate molecules and are cotransfected into the host cell.

In an alternative embodiment, the helper cell includes a replicon RNA encoding the alphavirus packaging segment, an inserted heterologous RNA, and the alphavirus capsid protein encoded by the second helper RNA, and the first helper RNA includes the alphavirus E1 glycoprotein and the alphavirus E2 glycoprotein. Thus, the replicon RNA and the first helper RNA are on separate molecules, and the replicon RNA and the second helper RNA are on a single molecule. The heterologous RNA comprises a foreign RNA.

The RNA encoding the structural proteins, i.e., the first helper RNA and the second helper RNA, may advantageously include one or more attenuating mutations. In an embodiment, at least one of the first helper RNA and the second helper RNA includes at least one attenuating mutation. The attenuating mutations provide the advantage that in the event of RNA recombination within the cell, the coming together of the structural and non-structural genes will produce a virus of decreased virulence.

As another aspect a method of making infectious, replication defective, alphavirus particles is provided. The method includes transfecting a helper cell as given above with a replication defective replicon RNA, producing the alphavirus particles in the transfected cell, and then collecting the alphavirus particles from the cell. The replicon RNA encodes the alphavirus packaging segment and a heterologous RNA. The transfected cell further includes the first helper RNA and second helper RNA as described above.

As another aspect, a set of RNAs is provided for expressing an infectious, replication defective alphavirus. The set of RNAs comprises, in combination, (a) a replicon RNA encoding a promoter sequence, an inserted heterologous RNA, wherein RNA encoding at least one structural protein of the alphavirus is deleted from the replicon RNA so that the replicon RNA is replication defective, and (b) a first helper RNA separate from the replicon RNA, wherein the first helper RNA encodes in trans, the structural protein which is deleted from the replicon RNA and which may or may not include a promoter sequence. In this embodiment, it is preferred that an RNA segment encoding at least one of the structural proteins is located on an RNA other than the first helper RNA. Thus, for example, the set of RNAs may include a replicon RNA including RNA which encodes the alphavirus packaging sequence, the inserted heterologous RNA, and the alphavirus capsid protein, but both the alphavirus E1 glycoprotein and alphavirus E2 glycoprotein are deleted therefrom; and a first helper RNA includes RNA encoding both the alphavirus E1 glycoprotein and the alphavirus E2 glycoprotein.

In another embodiment, the set of RNAs also includes a second helper RNA separate from the replicon RNA and the first helper RNA. In this embodiment, the second helper RNA encodes, in trans, at least one structural protein, which is different from the structural protein encoded by the replicon RNA and by the first helper RNA. Thus, for example, the set of RNAs may include a replicon RNA including RNA which encodes the alphavirus packaging sequence, and the inserted heterologous RNA; a first helper RNA including RNA which may encode a promoter sequence and an RNA encoding both the alphavirus E1 glycoprotein and the alphavirus E2 glycoprotein; and a second helper RNA including RNA which encodes the alphavirus capsid protein, with the replicon RNA, the first helper RNA, and the second helper RNA being in trans from each other, on separate molecules.

As another aspect, is provided a pharmaceutical formulation comprising infectious alphavirus particles as described above, in an effective immunogenic amount in a pharmaceutically acceptable carrier. See, for example, the '135 patent at column 2, line 10-column 11 line 52 which includes examples 1-5.

The phrases "structural protein" or "alphavirus structural protein" as used herein refer to the encoded proteins which are required for production of particles that contain the replicon RNA, and include the capsid protein, E1 glycoprotein, and E2 glycoprotein. As described hereinabove, the structural proteins of the alphavirus are distributed among one or more helper RNAs (i.e., a first helper RNA and a second helper RNA). In addition, one or more structural proteins may be located on the same RNA molecule as the replicon RNA, provided that at least one structural protein is deleted from the replicon RNA such that the replicon and resulting alphavirus particle are replication defective. As used herein, the terms "deleted" or "deletion" mean either total deletion of the specified segment or the deletion of a sufficient portion of the specified segment to render the segment inoperative or non-functional, in accordance with standard usage. See, e.g., U.S. Pat. No. 4,650,764 to Temin et al. The term "replication defective" as used herein, means that the replicon RNA cannot produce particles in the host cell in the absence of the helper RNA. That is, no additional particles can be produced in the host cell. The replicon RNA is replication defective inasmuch as the replicon RNA does not include all of the alphavirus structural proteins required for production of particles because at least one of the required structural proteins has been deleted therefrom.

The helper cell for production of the infectious, replication defective, alphavirus particle comprises a set of RNAs, as described above. The set of RNAs principally include a first helper RNA and a second helper RNA. The first helper RNA includes RNA encoding at least one alphavirus structural protein but does not encode all alphavirus structural proteins. In other words, the first helper RNA does not encode at least one alphavirus structural protein; that is, at least one alphavirus structural protein gene has been deleted from the first helper RNA. In one embodiment, the first helper RNA includes RNA encoding the alphavirus E1 glycoprotein, with the alphavirus capsid protein and the alphavirus E2 glycoprotein being deleted from the first helper RNA. In another embodiment, the first helper RNA includes RNA encoding the alphavirus E2 glycoprotein, with the alphavirus capsid protein and the alphavirus E1 glycoprotein being deleted from the first helper RNA. In a third, preferred embodiment, the first helper RNA includes RNA encoding the alphavirus E1 glycoprotein and the alphavirus E2 glycoprotein, with the alphavirus capsid protein being deleted from the first helper RNA. The second helper RNA includes RNA encoding the capsid protein which is different from the structural proteins encoded by the first helper RNA. In the embodiment wherein the first helper RNA includes RNA encoding only the alphavirus E1 glycoprotein, the second helper RNA may include RNA encoding one or both of the alphavirus capsid protein and the alphavirus E2 glycoprotein which are deleted from the first helper RNA. In the embodiment wherein, the first helper RNA includes RNA encoding only the alphavirus E2 glycoprotein, the second helper RNA may include RNA encoding one or both of the alphavirus capsid protein and the alphavirus E1 glycoprotein which are deleted from the first helper RNA. In the embodiment wherein the first helper RNA includes RNA encoding both the alphavirus E1 glycoprotein and the alphavirus E2 glycoprotein, the second helper RNA may include RNA encoding the alphavirus capsid protein which is deleted from the first helper RNA.

In one embodiment, the packaging segment or "encapsidation sequence" is deleted from at least the first helper RNA. In a preferred embodiment, the packaging segment is deleted from both the first helper RNA and the second helper RNA.

In an embodiment wherein the packaging segment is deleted from both the first helper RNA and the second helper RNA, preferably the helper cell contains a replicon RNA in addition to the first helper RNA and the second helper RNA. The replicon RNA encodes the packaging segment and an inserted heterologous RNA. The inserted heterologous RNA may be RNA encoding a protein or a peptide. The inserted heterologous RNA may encode a protein or a peptide which is desirously expressed by the host, alphavirus-permissive cell, and includes the promoter and regulatory segments necessary for the expression of that protein or peptide in that cell.

For example, in one preferred embodiment of the present invention, the helper cell includes a set of RNAs which include (a) a replicon RNA including RNA encoding an alphavirus packaging sequence and an inserted heterologous RNA, (b) a first helper RNA including RNA encoding the alphavirus E1 glycoprotein and the alphavirus E2 glycoprotein, and (c) a second helper RNA including RNA encoding the alphavirus capsid protein so that the alphavirus E1 glycoprotein, the alphavirus E2 glycoprotein and the capsid protein assemble together into alphavirus particles in the host cell.

In an alternate embodiment, the replicon RNA and the first helper RNA are on separate molecules, and the replicon RNA and the second helper RNA are on a single molecule together, such that a first molecule, i.e., the first helper RNA, including RNA encoding at least one but not all of the required alphavirus structural proteins, and a second molecule, i.e., the replicon RNA and second helper RNA, including RNA encoding the packaging segment, the inserted heterologous DNA and the capsid protein. Thus, the capsid protein is encoded by the second helper RNA, but the second helper RNA is located on the second-molecule together with the replicon RNA. For example, in one preferred embodiment of the present invention, the helper cell includes a set of RNAs including (a) a replicon RNA including RNA encoding an alphavirus packaging sequence, an inserted heterologous RNA, and an alphavirus capsid protein, and (b) a first helper RNA including RNA encoding the alphavirus E1 glycoprotein and the alphavirus E2 glycoprotein so that the alphavirus E1 glycoprotein, the alphavirus E2 glycoprotein and the capsid protein assemble together into alphavirus particles in the host cell.

In one embodiment of the present invention, the RNA encoding the alphavirus structural proteins, i.e., the capsid, E1 glycoprotein and E2 glycoprotein, contains at least one attenuating mutation. The phrases "attenuating mutation" and "attenuating amino acid," as used herein, mean a nucleotide mutation or an amino acid coded for in view of such a mutation which result in a decreased probability of causing disease in its host (i.e., a loss of virulence), in accordance with standard terminology in the art, See, e.g., B. Davis, et al., Microbiology 132 (3d ed. 1980), whether the mutation be a substitution mutation or an in-frame deletion mutation. The phrase "attenuating mutation" excludes mutations which would be lethal to the virus. Thus, according to this embodiment, at least one of the first helper RNA and the second helper RNA includes at least one attenuating mutation. In a more preferred embodiment, at least one of the first helper RNA and the second helper RNA includes at least two, or multiple, attenuating mutations. The multiple attenuating mutations may be positioned in either the first helper RNA or in the second helper RNA, or they may be distributed randomly with one or more attenuating mutations being positioned in the first helper RNA and one or more attenuating mutations positioned in the second helper RNA. Appropriate attenuating mutations will be dependent upon the alphavirus used. For example, when the alphavirus is VEE, suitable attenuating mutations may be selected from the group consisting of codons at E2 amino acid position 76 which specify an attenuating amino acid, preferably lysine, arginine, or histidine as E2 amino acid 76; codons at E2 amino acid position 120 which specify an attenuating amino acid, preferably lysine as E2 amino acid 120; codons at E2 amino acid position 209 which specify an attenuating amino acid, preferably lysine, arginine, or histidine as E2 amino acid 209; codons at E1 amino acid 272 which specify an attenuating mutation, preferably threonine or serine as E1 amino acid 272; codons at E1 amino acid 81 which specify an attenuating mutation, preferably isoleucine or leucine as E1 amino acid 81; and codons at E1 amino acid 253 which specify an attenuating mutation, preferably serine or threoinine as E1 amino acid 253.

In an alternate embodiment, wherein the alphavirus is the South African Arbovirus No. 86 (S.A.AR86), suitable attenuating mutations may be selected from the group consisting of codons at nsP1 amino acid position 538 which specify an attenuating amino acid, preferably isoleucine as nsP1 amino acid 538; codons at E2 amino acid position 304 which specify an attenuating amino acid, preferably threonine as E2 amino acid 304; codons at E2 amino acid position 314 which specify an attenuating amino acid, preferably lysine as E2 amino acid 314; codons at E2 amino acid position 376 which specify an attenuating amino acid, preferably alanine as E2 amino acid 376; codons at E2 amino acid position 372 which specify an attenuating amino acid, preferably leucine as E2 amino acid 372; codons at nsP2 amino acid position 96 which specify an attenuating amino acid, preferably glycine as nsP2 amino acid 96; and codons at nsP2 amino acid position 372 which specify an attenuating amino acid, preferably valine as nsP2 amino acid 372. Suitable attenuating mutations useful in embodiments wherein other alphaviruses are employed are known to those skilled in the art. Attenuating mutations may be introduced into the RNA by performing site-directed mutagenesis on the cDNA which encodes the RNA, in accordance with known procedures. See, Kunkel, Proc. Natl. Acad. Sci. USA 82:488 (1985). Alternatively, mutations may be introduced into the RNA by replacement of homologous restriction fragments in the cDNA which encodes for the RNA, in accordance with known procedures.

A protective molecule in one embodiment may be a nucleic acid molecule of interest also referred to as a gene of interest and refers to a nucleic acid molecule which may or may not represent an entire gene of the microorganism. As used herein, the terms nucleic acid or polynucleotide refer to deoxyribonucleotides or ribonucleotides and polymers thereof in either single- or double-stranded form. The nucleic acid molecule used to make the vaccine may be the same sequence obtained from the sample, or can refer to a sequence synthetically produced based upon the sequence obtained from the sample. As such, the terms include RNA and DNA, which can be a gene or a portion thereof, a cDNA, a synthetic polydeoxyribonucleic acid sequence, or the like, and can be single-stranded or double-stranded, as well as a DNA/RNA hybrid. Furthermore, the terms are used herein to include naturally-occurring nucleic acid molecules, which can be isolated from a cell, as well as synthetic molecules, which can be prepared, for example, by methods of chemical synthesis or by enzymatic methods such as by the polymerase chain reaction (PCR). Unless specifically limited, the terms encompass nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260:2605-2608; Cassol et al. (1992); Rossolini et al. (1994) Mol. Cell. Probes 8:91-98). The term nucleic acid is used interchangeably with gene, cDNA, and mRNA encoded by a gene.

The protective molecule may also be an RNA interfering molecule or one from which an RNA interfering molecule is produced, or which encodes a polypeptide or fragment thereof that produces a protective and/or immune response in the animal when administered to the animal. A noted above, it is at times also referred to as a protective molecule or protective antigen determinant. In certain embodiments where a polypeptide is provided, the polypeptide may be at least two, three, four, five, six, seven, eight, nine or ten or more amino acids or more. A peptide is generally considered to be more than fifty amino acids. The terms "fragment," "derivative" and "homologue" when referring to the polypeptides according to the present invention, means a polypeptide which retains essentially the same biological function or activity as said polypeptide, that is, act as an antigen and/or provide treatment for and/or protection against disease. Such fragments, derivatives and homologues can be chosen based on the ability to retain one or more of the biological activities of the polypeptide, that is, act as a protective agent and/or provide treatment for and/or protection against the pathogen. Thus, a homologue includes a polypeptide from a different strain or genus that retains essentially the same biological function or activity as the polypeptide. The polypeptide vaccines of the present invention may be recombinant polypeptides, natural polypeptides or synthetic polypeptides, preferably recombinant polypeptides.

A protective molecule, then may be the nucleic acid molecule of interest obtained from the biological sample, whether obtained directly or produced (as synthetically) from the nucleic acid molecule of interest; the polypeptide it produces; interfering RNA such as antisense or dsRNA; DNA producing the antisense or dsRNA; the replicon particles comprising the nucleic acid molecule, antisense or dsRNA or a combination which comprises the vaccine. The animal may or may not produce antibodies in response, but the animal will have decreased morbidity or mortality resulting from administration of the vaccine, and as described further herein.

The invention can be applied to any microorganism/pathogen that causes adverse impact in a aquatic invertebrate and is not limited to any particular such microorganism. In particular, the present invention provides for methods to immunize against, or to prevent or to reduce the symptoms caused by, infection of such an animal with a pathogenic organism. Thus when referring to a microorganism it is meant to include any such disease-causing agent, for example, a virus, bacteria, fungus, or protozoan parasite. Protection from disease is provided by the vaccine of the invention, that is, protection from all or some of the adverse impact on the animal's health.

Without intending to be limiting, examples of disease causing agents in aquatic invertebrates include Picornavirales viruses such as Marnavirdae, and Dicistronvirdae, Calciviridae such as San Miguel sea lion viruses (SMSV) which can infect invertebrates, Nodaviridae such as *Penaeus vannamei* Nodaviridae (PvNV) affecting shrimp, Iridovirus affecting shrimp and prawns, Ronivirdae such as Yellow Head Virus (YHV) affecting shrimp, prawns and krill, Bunyaviridae viruses, such as Mourilyan virus (MoV) impacting shrimp, Birnaviridae (such as Infectious Pancreatic Necrosis Virus (IPNV) which can impact oysters), icosahedral virus causing Oyster velar virus disease (OVVD), *Nocardia* sp. bacterium infecting oysters and causing nocardiosis, *Vibrio angudarum, V. alginolyticus* and *V. tubiashii* infecting bivalves, *Aeromonas hydrophila* infecting snails, Rickettsiae, Chlamydiae and Mycoplasmis infecting bivalve molluscs, *Leucothrix mucor* infecting clams, *Haliphthoros milfordensis* infecting oyster drill, *Leptolegnia* or *Leptoleginella marina* infecting clams, *Perkinsus marinus meront* and *Perkinsus atlanticus* infecting molluscs, *Haplosporidium* sp., *Bonamia* sp. and *Minchinia* sp. infecting molluscs, Thraustochytrid infecting squid, nudibranch and octopus, and *Perkinsus quqwadi* affecting scallop.

Without intending to be limiting, examples of such disease causing agents in shrimp include White Spot Syndrome Virus (WSSV) Taura Syndrome Virus (TSV), Infectious Myonecrosis Virus (IMNV), Infectious hypodermal and hematopoietic necrosis virus (IHHNV), or *Penaeus stylirostris* densovirus (PstDV), Baculovirus of penaeid shrimp (BP), Rhabdovirus of penaeid shrimp (RPS), Gill-associated virus (GAV), Yellow head virus (YHV), Lymphoid organ-associated virus (LOVV), Lymphoidal parvolike viral disease (LPV), hepatopan-creatic parvo-like virus (HPV), or *Penaeus monodon* densovirus (PMDV) Baculoviral midgut gland necrosis virus (BMN), Monodon baculovirus (MBV) Reo like virus diseases (REO), Rhabdovirus (RPS), *Macrobrachium rosenbergii* nodavirus (MrNV), Laem-Singh virus (LSNV), Mourlyan virus (MoV), *Vibrio vulnificus Vibro parahaemolyticus, Vibrio anguillarinum, Vibrio penaeicida,* Necrotizing Hepatopancreatitis Bacterium (NHPB), *Vibrio harveyi,* Spiroplasma, *Mycobacterium, Streptococcus* spp., Ciliates, Gregarines, Parasitic Helminths, *Fusarium* spp., Microsporidia, and Haplosporidia.

Also of importance in protecting aquatic animals, and in particular shrimp and other farmed aquatic invertebrate animals from disease is rapid production of a vaccine for the disease. The use of the Replicon Particle technology described here in the invention allows for such a rapid response by introducing into the Replicon Particle the gene of interest to efficiently and quickly produce a vaccine. (Vander Veen et al. Rapid development of an efficacious swine vaccine for novel H1N1. PLoS Curr. 2009 Oct. 29; 1:RRN1123.)

The invention is particularly useful in protecting shrimp from disease, as there is a need for vaccines for shrimp, in particular farmed shrimp. One such disease, for example, is White Spot Syndrome Virus (WSSV). Current production practices focus on pathogen exclusion by stocking specific pathogen free (SPF) larvae, decontamination and filtration of water to prevent pathogen introduction, and strict biosecurity at the hatchery pond sites. These can be effective as long as virus remains excluded, but this is extremely challenging due to the prevalence of WSSV in estuarine waters in shrimp producing areas. It also continues to cause devastating financial losses due to such acute mortality in naive susceptible SPF populations.

Several control strategies have been utilized experimentally that show some degree of promise. *Fenneropenaeus indicus* (Indian Prawn) was shown to be protected by the oral administration of formalin inactivated WSSV virions. (Singh, I. S. B., Manjusha, M., Pai, S. S., Philip, R., 2005. *Fenneropenaeus indicus* is protected from WSSV-induced disease by oral administration of inactivated WSSV. Disease of Aquatic Organisms 66, 265-270.) However, this effect seems to be variable and no protection was conferred to *Litopenaus vannamei* (Pacific White Shrimp), the primary aquaculture species, when orally administered (Loy and Harris unpublished). No significant differences in mortality or quantitative Real Time PCR viral genome copy number were observed between vaccinates and controls in a homologous challenge study (Loy and Harris unpublished).

Protein subunit vaccines to WSSV envelope proteins have been shown to be effective at conferring protection to WSSV infection in both shrimp and crayfish. WSSV contains 4 major envelope proteins with no known homology to other virus proteins; these include VP28, VP26, VP24, and VP19. VP28 is present on the outer membrane and is involved in cellular entry. (McClennen, C. White Spot Syndrome Virus, The Economic, Environmental and Technical Implications on the Development of Latin American Shrimp Farming. Master of Arts in Law and Diplomacy Thesis. 2004, In Press.) VP28 antisera has been shown to neutralize virus in vivo (McClennen, supra.) Recent studies have demonstrated that these four major envelope proteins bind to form a complex via several pairwise protein interactions and one self-association (VP28). (Zhou, Q., Xu, L., Li, H., Qi, Y.-P., Yang, F., 2009. Four Major Envelope Proteins of White Spot Syndrome Virus Bind To Form A Complex. Journal of Virology 83, 4709-4712.)

Subunit vaccines consisting of both VP28 and VP19 conferred protection to WSSV infection, however protection was short-lived such that 25 days following administration no protection was conferred. (Witteveldt, J., Vlak, J. M., Van Hulten, M. C. W., 2004. Protection of Penaeus monodon against white spot syndrome virus using a WSSV subunit vaccine. Fish & Shellfish Immunology 16, 571-579.) DNA vaccines to various WSSV envelope proteins have also demonstrated some utility in preventing infection. Naked DNA vaccines for VP28 and VP281 were injected into Penaeus monodon demonstrable-protection was observed for up to 7 weeks. (Rout, N., Kumar, S., Jaganmohan, S., Murugan, V., 2007. DNA vaccines encoding viral envelope proteins confer protective immunity against WSSV in black tiger shrimp. Vaccine 25, 2778-2786.) However, injection of naked DNA to individuals is not ideal in a commercial setting due to cost of production and feasibility of individual animal injection in the field. Ning et al. demonstrated that *Salmonella typhimurium* expressing VP28 conferred protection against infection for up to 25 days following oral administration. However, the bacteria remained in the crayfish for only seven days. Ning et al. (2009) "*Oral delivery of DNA vaccine encoding VP28 against white spot syndrome virus in crayfish by attenuated*

*Salmonella typhimurium" Vaccine* 27:1127-1135. Fu et al. showed that *Bacillus subtilis* spores and vegetative cells expressing VP28 protected *Procambarus clarkii* (Freshwater crayfish) against WSSV infection 14 days after administration, and that crayfish treated with spores had a higher survivability than those given vegetative cells. Fu et al. *"Oral vaccination with envelope protein VP28 against white spot syndrome virus in Procambarus clarkii using Bacillus subtilis as delivery vehicles" The Society for Applied Microbiology, Letters in Appl. Micro.* 146:581-586 (2008). However, problems with using attenuated bacteria expression systems exist. They still require the introduction of live organisms that have the ability to revert to virulence and may be pathogenic to humans. Due to current problems with all the existing techniques in vaccinating for white spot virus, we propose a different platform for vaccination.

This body of previously published work focused on either dsRNA or using protein delivery as a vaccine or receptor "blocker" for these viral disease. Here, in one embodiment, a vector is used to deliver single stranded RNA that is the sequence complement of specific viral sequences, and upon infection creates a RNA/RNA complementary structure. An embodiment involves delivering this RNA or using a nucleic acid molecule of the pathogen using an alphavirus derived replicon particle vector. Another embodiment uses dsRNA alone or in a replicon particle vector.

Infectious myonecrosis virus (IMNV) is another problematic disease in shrimp and is a non-enveloped, small (40 nm) icosohedral, monosegmented, dsRNA virus, and is a member of the Totiviridae. (Poulos, B. T., Tang, K. F. J., Pantoja, C. R., Bonami, J. R., Lightner, D. V., 2006. Purification and characterization of infectious myonecrosis virus of penaeid shrimp. Journal of General Virology 87, 987-996.) This disease was subsequently reproduced in specific pathogen free (SPF) animals by injection of sucrose density gradient purified virions fulfilling Rivers' postulates. (Poulos et al., 2006, supra.) IMNV disease is characterized by skeletal muscle necrosis in the distal abdominal segments followed by mortality, especially following periods of acute stress. Histopathologically, animals demonstrate a characteristic coagulative necrosis of skeletal muscle with fluid accumulation in between muscle fibers, along with pronounced hypertrophy of the lymphoid organ due to accumulation of spheroids. (Poulos et al., 2006, supra.) IMNV was first discovered in 2003 after a severe outbreak in NE Brazil in 2002 of high mortalities and animals exhibiting necrosis in the tail muscle. It is estimated that in 2003 alone IMNV cost Brazil millions of dollars in losses. (Lightner, D. V., 1999. The Penaeid Shrimp Viruses TSV, IHHNV, WSSV, and YHV: Current Status in the Americas, Available Diagnostic Methods, and Management Strategies. Journal of Applied Aquaculture 9, 27-52.) IMNV was recently confirmed in Indonesia in 2006, and presents a very real risk for spread throughout the world. As there are no current therapies or vaccines, and little is known about the epidemiology of this virus, this would cause significant impact on the commercial shrimp farming industry. (Senapin, S., Phewsaiya, K., Briggs, M., Flegel, T. W., 2006. Outbreaks of infectious myonecrosis virus (IMNV) in Indonesia were confirmed by genome sequencing and use of an alternative RT-PCR detection method. Aquaculture 266, 32-38.) In previous outbreaks, mortalities ranged from 40% to 70% with large impacts in production even following large reductions in stocking densities. Feed conversion ratio (FCR) varied from a normal 1.5 to upwards of 4.4. (Andrade, T. P. D., Srisuvan Thinnarat, Tang, K. F. J., Lightner, D. V., 2007. Real-time reverse transcription polymerase chain reaction assay using TaqMan probe for detection and quantification of Infectious myonecrosis virus (IMNV). Aquaculture 264, 9-15.) This has been associated with seasonal fluctuations during the dry season, and the most significant factors associated with IMNV outbreaks were long rearing periods and high stocking densities. (Arms da Silva, V., dos Santos, F. L., Bezarro, S. S., Pedrosa, V. F., Mendes, P., Mendes E. S., 2010, A multi-season survey for infectious myonecrosis in farmed shrimp, *Litopenaeus vannamei*, in Pernambuco, Brazil. Journal of Invertebrate Pathology 104, 161-165.) Due to the current and tremendous future potential impact this disease has on the shrimp industry, development of a vaccine or mitigation strategy is prudent. The aim of this work was to discover RNAi trigger sequences that would elucidate a protective response when inoculated into animals at a low dose and for extended periods of time following inoculation.

The IMNV genome contains two open reading frames (ORFs). The IMNV genome is disclosed in Nibert et al, (2007) *Journal of General Virology* 88:1315-1318. and at GenBank accession Number AY570982 by Poulos et al. (2006) and also at Genbank accession Number EF061744 by Senapin et al. (2007). The two GenBank sequences differ by one nucleotide, where the Poulos et al. sequence is 7560 by and the Senapin et al. sequence has an additional nucleotide insertion of adenine and is 7561 by in length. The sequence of Poulos et al. is shown in SEQ ID NO: 66 and of Senapin at SEQ ID NO: 67. The sequence of Senapin contains a single nucleotide insertion of adenine at by 7431 of the genomic sequence. The polypeptide encoded by the ORF1 sequence of Poulous et al. sequence is shown at SEQ ID NO: 68, and the polypeptide encoded by the ORF1 sequence of Senapin is shown at SEQ ID NO: 69. The polypeptide encoded by encoded by the Poulous et al. ORF2 sequence is shown at SEQ ID NO: 70 (GenBank No. AAT67231.1) and that encoded by the Senapin et al. sequence is shown at SEQ ID NO: 71 (GenBank ABN05325.1). This area of difference was not targeted in the work here. The ORF1 encodes the major capsid protein (nucleotides 136-4953 of SEQ ID NO: 66 or 67 and identified as SEQ ID NO: 72) and ORF2 (nucleotides 5241-7451, SEQ ID NO: 73) encodes a 736 amino acid RNA dependent RNA polymerase (RdRp) (Poulos et al., 2006, supra; see also Nibert, 2007, supra.) ORF1 encodes a 179 kDa protein (1605 amino acids) including the N-terminal sequence of the major capsid protein. The capsid is isometric with a diameter of approximately 400 angstroms. Recent studies of the IMNV genome have revealed a "2A-like" cleavage and "shifty heptamer" that may contribute to a capsid protein-RdRp fusion protein as well as three cleavage proteins of ORF 1. These have been described as "Peptide 1," "Peptide 2," and "Peptide 3." There remains some speculation as to the role of these proteins. "Peptide 1" spanning bases 136-415 (SEQ ID NO: 74, is a 10 kDa, 93 amino acid region at the N-terminus of ORF 1, shares sequence similarities with known dsRNA binding proteins, and may be involved in host immune suppression. (Tang et al., 2008 Infectious myonecrosis virus has a totivirus-like 120-subunit capsid, but with fiber complexes at the fivefold axes. PNAS 105:17526-17531.) "Pep2" a 32 kDa, 284 aa product, spanning bases 415-1266 (SEQ ID NO: 75) and "Pep3" a 38 kDa, 327 aa product, spanning 1267-2247 (SEQ ID NO: 76), together represent the first 704 amino acids of ORF1, have been speculated to be candidate minor proteins visualized on denaturing gels, however this remains speculative in nature (Tang, et al., 2008, supra).

Figure 2:
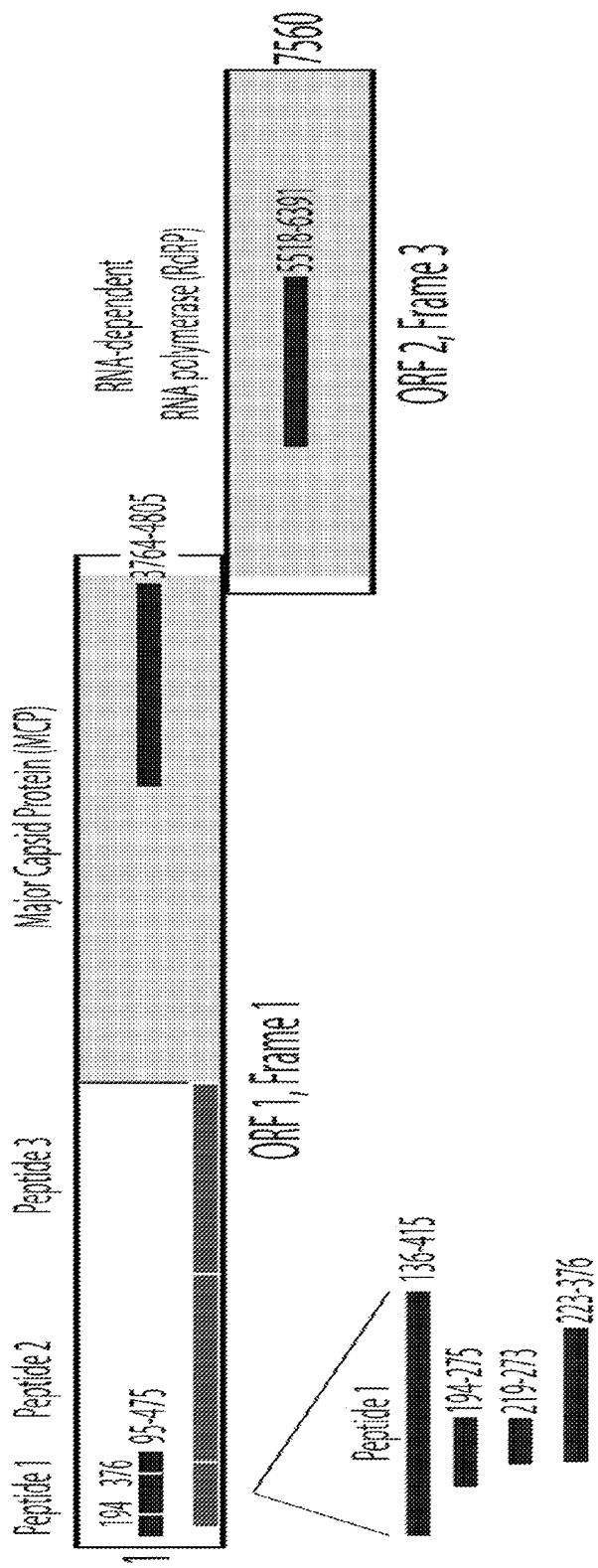
FIG. 2 is a diagram of the IMNV genome transcription and translation products showing regions targeted for RNAi, predicted protein products are indicated by dark gray lines or gray shading, with target regions for dsRNA production indicated as thick black lines.

Three target regions, spanning the length of the viral genome, were selected as initial targets for dsRNA generation (see FIG. 2). The first were sequences corresponding to the N-terminal region of ORF1 frame 1, predicted to contain two co-translationally cleaved products, spanning Peptide 1 and 2 (dsRNA95-475, SEQ ID NO: 1; see also SEQ ID NO: 80 which excludes the non-essential adenine as last base pair). In addition portions of the major capsid protein (MCP) (dsRNA3764-4805, here SEQ ID NO: 4) and RNA dependent RNA polymerase (RdRp) dsRNA5518-6391 (see SEQ ID NO: 5; see also SEQ ID NO: 85 which excludes the non-essential 3' three nucleotides (CTT) and provides the sequence in orientation as used in the experiments) were selected for dsRNA generation. Peptide 1 (93 aa) and 2 (284 aa) are encoded by nucleotides 136-415 (SEQ ID NO: 74) and 415-1266 (SEQ ID NO: 75) of the IMNV genome within ORF 1 frame 1, respectively, and their functions remain uncharacterized. Peptide 1 shares sequence homology with previously described dsRNA binding proteins, The major capsid protein (909 amino acids) of IMNV is encoded by nucleotides 2227-4953 (SEQ ID NO: 77) within ORF 1, frame 1. The RNA dependent RNA polymerase (736 amino acids) is encoded by nucleotides 5241-7451 (SEQ ID NO: 78) within ORF2, frame 3. A non-specific control dsRNA was designed to an exogenous sequence corresponding to enhanced green fluorescent protein (eGFP). Shorter dsRNAs were designed within the area of the IMNV genome that encodes Peptide 1 (FIG. 2). Two dsRNAs were generated as 100 by truncations from the 5' (bp193-475, SEQ ID NO: 2; see also SEQ ID NO: 81, which is 194-474 and excludes a non-essential adenine as the first and last base pair) or 3' (bp95-376, SEQ ID NO: 3) end of the original dsRNA95-475 (SEQ ID NO: 1).

The means and methods of producing such a vaccine are known to one skilled in the art and many variations and approaches to such production are known and expected to be further developed. The following sets forth as examples some of the many options available to produce and administer such a vaccine. A discussion of an example of various means for producing and administering vaccines of the invention is described at Harris et al., U.S. Pat. No. 7,622,254, incorporated herein by reference in its entirety.

One means of producing such a vaccine is to produce an autogenous vaccine, that is, to use a a method of producing a vaccine is provided which protects the animal from adverse effects of a biotype of a pathogenic microorganism. Disclosed here and at US patent application "Method of rapidly producing improved vaccines for animals" U.S. Ser. No. 13,277,076, US Publication No. 20120107355 (and which claims priority to U.S. provisional application Ser. No. 61/407,297 filed Oct. 27, 2010, U.S. Ser. No. 61/418,433, filed Dec. 1, 2010; to U.S. Ser. No. 61/449,940 filed Mar. 7, 2011; to U.S. Ser. No. 61/484,255 filed May 10, 2011; to U.S. Ser. No. 61/508,172 filed Jul. 15, 2011; and to U.S. Ser. No. 61/525,332 filed Aug. 19, 2011), is a description of producing a vaccine from an autogenous source. The contents of each are incorporated herein by reference in their entirety. Also described and as shown in the examples below is an autogenous source of a nucleic acid molecule of interest and protective molecule. In the autogenous process, in summary, a biological sample is obtained from an animal which has been exposed to a microorganism, a nucleic acid molecule of interest of fragment thereof of the microorganism is obtained from the sample and a protective molecule produced from the nucleic acid of interest. The protective molecule may be a nucleic acid molecule comprising the sequence or a fragment of the nucleic acid molecule of interest, may be a polypeptide or fragment produced by the nucleic acid molecule of interest, or may be an RNA molecule that is antisense to the nucleic acid molecule of interest or forms a dsRNA that corresponds to all or a portion of the nucleic acid molecule of interest or nucleic acid molecule producing same or replicon particle comprising or producing same. With such a process, an improved vaccine is provided to protect animals against a pathogen which can be prepared very rapidly and which addresses the problem of providing protection to animals against a new or evolving biotypes. The vaccine is an autogenous vaccine, that is, it is prepared from the nucleic acid molecule from an infectious agent present on a specific farm, flock, herd, pond or geographic region. It is not necessary to isolate the infectious agent in the laboratory to obtain the gene. It is prepared from the nucleic acid of microorganism(s) present in an animal or a group of animals which have been exposed to a biotype of a pathogenic microorganism. Such animals from which the nucleic acid molecule is obtained are those living in an environment such that one can expect are likely to have been exposed to the same pathogen biotype. By way of example, without limitation, where such animals are livestock animals, they may be found living in a ranch, feed yard, farm, pond or region and with sufficient contact such that one skilled in the art would expect such animals to have come into contact or are likely to come into contact with the same pathogen. Upon preparation of the autogenous vaccine, these animals would then be vaccinated with the vaccine. As provided for with by the American Veterinary Medical Association (AVMA), adjacent or non-adjacent groups of animals considered to be at risk may also be vaccinated. See www.avma.org/issues/policy/autogenous_biologics.asp "Guidelines for Use of Autogenous Biologics" (Oversight: COBTA; EB approved-1993; reaffirmed 11/97; reaffirmed 4/01; revised 3/06, 11/09). When referring to an autogenous vaccine is meant to include this current definition of the AVMA in which animals considered to be at risk may be vaccinated. Also, an individual animal may be the sole animal for which the autogenous vaccine is prepared. The source of the microorganism nucleic acid molecule of interest is any convenient biological sample such as animal tissue, fluid or cell which are expected to have the nucleic acid of the microorganism present, whether blood, skin, organ tissue, body fluids or the like.

The term biotype refers to distinguishing a pathogenic agent by one or more characteristics over other members of the pathogenic species. The invention is particularly useful in providing a process to quickly produce a vaccine that is useful with different and/or new biotypes of a pathogen, and in an embodiment is especially useful where a biotype is found in a particular group of exposed animals or with potential for exposure to that biotype. Using current methods, a vaccine that is available may not be helpful against a different or newly evolving biotype. This invention provides a process where a vaccine that is useful with the new or different biotype is quickly developed. A biotype variant of a species can be distinguished by a variety of one or more characteristics, such as ribosomal RNA sequence variation, DNA polymorphisms, pathogenic response, response of the exposed animal to a specific vaccine, serological typing of toxin production or many other possible variations depending upon the pathogenic agent (see e.g., Sambrook et al. Molecular Cloning: A Laboratory Manual, 2nd Edit., Cold Spring Harbor Laboratory, cold Spring Harbor, N.Y. 2001; DNA cloning A Practical Approach, Vol. I and II, Glove, D. M. edit. IRL Press Ltd., Oxford, 1985; Harlow and Lane, Antibodies a Laboratory Manual, Cold Spring Harbor Publications, N.Y. 1988). By way of example, without limitation, influenza can be biotyped by distinguishing it by subtype and cluster. The category is determined by differences of their internal proteins, and further by differences of the hemagglutinin and neuraminidase proteins. A hemagglutinin inhibition test can be used, in one example, where a sample of specified dilution is applied to red blood cells and the titer determined by the maximum dilution that produces agglutination. Antibodies to the virus prevent attachment to red blood cells and thus hemagglutination is inhibited when antibodies to influenza virus are present. Results are reported as the reciprocal of maximum dilution that provides visible agglutination. See. e.g., Katz et al. (2009) Morbid. Mortal. Weekly Rep. 58 (19) 521-524.

Another example of biotyping is glycan typing where genotypes are grouped based on their glycosylation patterns. Such a process is described at Harris et al., U.S. Pat. No. 7,622,254, incorporated herein by reference in its entirety (see especially, for example, table 7 columns 48 and 49). For example, the strains of PRRSV (Porcine Reproductive Respiratory Virus) are classified based on whether they are European or North American strains. In another aspect of typing the PRRSV strains, the first letter is either EU (European like) or NA (North American like) to designate the genotype cluster. EU refers to isotypes of PRRSV characterized by conserved glycans at position 46, 53, or both in GP5. As used herein, NA refers to isotypes of PRRSV characterized by conserved glycans at position 44, 51, or both in GP5. Each strain is given a number corresponding to the number of glycosylation sites located in the ectodomain of GP5 amino acid sequence shown in Table 7 of '254, but excludes highly conserved glycans located at aa44 and 51 for NA strains and aa46 and 53 for EU strains. Thus, NA-0 refers to the ectodomain of GP5 of NA strain that has no glycan and EU-0 refers to the ectodomain of GP5 of an EU strain that has no glycan. For example, NA-1 refers to the ectodomain of GP5 of a North American strain that has 1 glycan located on the ectodomain of GP5 excluding highly conserved glycans located at aa44 and 51 for NA strains. Table 1 represents such a glycantyping of PRRSV.

TABLE 1

| PRRSV Glycantype[a] | Number of predicted glycans[b,c] |
|---|---|
| NA-0 | 0[d] |
| NA-1 | 1 |
| NA-2 | 2 |
| NA-3 | 3 |
| NA-4 | 4 |
| NA-n | n |
| EU-0 | 0 |
| EU-1 | 1 |
| EU-2 | 2 |
| EU-3 | 3 |
| EU-4 | 4 |
| EU-n | n |

[a]NA + North American, EU = European
[b]Number of glycans located on the ectodomain of GP5 excluding highly conserved glycans located at aa44 and 51 for NA strains and aa46 and 53 for EU strains. When these glycans are absent they should be noted as follows: if an NA-1 strain lacks a glycan at aa44 it is described as NA-1 (Δ44).
[c]As the number of predicted glycans increases so does the resistance to inducing protective (neutralizing) antibodies and/or susceptibility to such antibodies.
NA-0 and EU-0 are predicted to be the parent strains for all NA and EU strains respectively. Thus these viruses should be included in attempts to generate cross-reacting antibodies. After NA-0 and EU-0, glycantyping may be a predictor of heterology which is currently poorly defined for PRRSV.

Any biotyping method to distinguish a pathogen from another of the species may be used in the invention.

This provides a useful approach to the generation of autogenous vaccines. In current processes used, the whole organism is isolated, then attenuated or killed, and the animal vaccinated with the prepared virus. By way of example, U.S. Pat. No. 4,692,412 to Livingston et al. describes a method for preparing an autogenous vaccine for neoplastic diseases by mixing a sterile blood sample containing Progenitor cryptocides with sterile distilled water, incubating the admixtures, killing or inactivating the Progenitor cryptocides in the admixtures, microfiltering the admixture to remove blood cells and diluting the filature to form the vaccine. Here, rather than use the whole organism (either live or inactivated) as the vaccine, one uses only one or more microorganism individual gene(s) of interest (GOI) also referred to as the nucleic acid molecule of interest (NOI) or fragments thereof, derived from the pathogen and/or the protein such gene(s) encode that makes up the autogenous vaccine. Surprisingly, it is possible to produce a vaccine using such nucleic acid molecules and to provide an effective vaccine which protects the animal. The gene of interest refers to a nucleic acid molecule which may or may not represent an entire gene and may be one from which an RNA interfering molecule is produced, or encodes a polypeptide or fragment thereof that produces a protective and/or immune response in the animal when administered to the animal. As one skilled in the art appreciates, the actual vaccine uses a protective molecule and may contain the gene of interest or fragment thereof, or may contain the polypeptide or fragment thereof producing the protective response, or may contain the interfering RNA or may contain a combination. The process is advantageous for the following reasons:

1) The new vaccines do not contain live virus. Current modified live virus (MLV) vaccines could not be used in an eradication effort due to their ability to spread, revert to virulence, or recombine with field strains.

2) The new vaccines can differentiate infected from vaccinated animals. Current MLV and killed vaccines use the whole virus. Here the entire infective agent is not included.

3) Autogenous vaccines and can be produced quickly. Autogenous vaccines are desirable for animal disease treatment due to strain/biotype variation and lack of cross-protection. ARP vaccines can be produced faster (1 month and even less) than traditional autogenous vaccines (3 months) allowing for a quicker response.

In a yet further embodiment, one can optionally first determine if preparation of a new autogenous vaccine as described is more advisable by determining the antigenic drift of the pathogen. In such an embodiment, one obtains a sample comprising the microorganism as described above, and may optionally determine what biotype it is. Using influenza as an example, the subtype and cluster may be determined. In general, influenza viruses are made up of an internal ribonucleoprotein core containing a segmented single-stranded RNA genome and an outer lipoprotein envelope lined by a matrix protein. The genome of influenza viruses is composed of eight segments of linear (−) strand ribonucleic acid (RNA), encoding the immunogenic hemagglutinin (HA) and neuraminidase (NA) proteins, and six internal core polypeptides: the nucleocapsid nucleoprotein (NP); matrix proteins (M); non-structural proteins (NS); and three RNA polymerase (PA, PB1, PB2) proteins. During replication, the genomic viral RNA is transcribed into (+) strand messenger RNA and (−) strand genomic cRNA in the nucleus of the host cell. Each of the eight genomic segments is packaged into ribonucleoprotein complexes that contain, in addition to the RNA, NP and a polymerase complex (PB1, PB2, and PA). As noted, influenza is grouped into three categories, based on the absence of serologic cross reactivity between their internal proteins: influenza A, B and C. Influenza A viruses are further classified into groups by antigenic differences of hemagglutinin and neuraminidase proteins. Examples of subtypes and further classification into clusters are shown in Table 2 below. The hemagglutinin antigens of influenza viruses change frequently in antigenic specificity as a result of changes in the HA and NA amino acid sequence.

TABLE 2

| Subtype | Representative HA sequence | Cluster |
| --- | --- | --- |
| H3N2 | A/Swine/Indiana/7688/2007 (H3N2) | 4 |
| cH1N1 | A/swine/Iowa/15/1930(H1N1) | α |
| rH1N1 | A/swine/Illinois/4661/2009 (H1N1) | β |
| H1N1 | A/Swine/Illinois/11678/2008 (H1N2) | γ |
| 2009 H1N1 | A/California/04/2009(H1N1) | γ |
| huH1N1 huH1N1 | A/Swine/Illinois/49271/2008 (H1N2) | δ |

In an embodiment of the invention, the antisera is obtained, and determined if it is the same biotype—in the present example if it reacts in the same manner as a standard obtained using existing vaccine. This can be measured in the case of influenza by using an hemagluttinin inhibition test as a standard, as described infra. If it reacts the same, then the existing vaccine can be used, if it does not match, then a new vaccine may be prepared. This is a means of measuring drift, that is change in the antigenic components. This is more effective than measuring shift, that is a major change to a new subtype. By measuring antigenic components, the virus may still fall within the same cluster, yet demonstrate a sufficient drift that a new vaccine would be more effective. While presented by way of example regarding an influenza virus, clearly one could apply such a process to any microorganism.

For many pathogens the protective molecule(s) needed to induce protection are known. The gene of interest of a pathogen is first amplified from a diagnostic sample originating from the farm. While one can isolate and purify the pathogen, it is not necessary with this method. Not only in such an embodiment does this eliminate an unnecessary step and speed the production process, it removes the need to have an isolated pathogen. The gene may be isolated or any protective portion of it isolated by using any available method such as PCR. The gene is then used to prepare the vaccine and ultimately used to vaccinate animals that have been or may be exposed to the pathogen. These vaccines when compared to currently available vaccines would be faster, biotype specific, and compatible with diagnostic tests. Vaccines so produced and a method of protecting an animal using the vaccine is also provided.

In one embodiment of the invention, a method of identifying protective sequences of the virus or nucleic acids that elicit protection is provided. This method also includes fragments, derivatives, or homologs of the protective molecule. In one aspect, the method comprises administering to a test animal such sequences. The test and control animals are subsequently challenged with an infectious amount of a microorganism that causes the disease. Various methods and techniques for determining whether protection is provided are known to those skilled in the art, including but not limited to, observing a difference between the test and control animal in the symptoms of the disease, for example. A decrease in any of the symptoms observed in the test animal compared to the control animal indicates that protective molecule(s) provide a degree of protection against disease. Similar symptoms or an increase in any of the symptoms observed in the test animal compared to those observed in the control animal indicate that the protective molecule(s) do not provide protection.

In another aspect, determining whether the protective molecules provided protection against infection includes determining the presence or absence of challenge disease in the test animal by electron microscopy or antibody or assays such as the fluorescent focusing neutralizing (FFN) test or Western blot assay may be used. PCR methods may be used to determine if the protective molecule is present. Northern blotting can detect the presence of diagnostic sequences. In another aspect, an ELISA or similar assay is among the types of many varied assays that can determine if the protective molecule is effective. The ELISA or enzyme linked immunoassay has been known since 1971. In general, antigens solubilised in a buffer are coated on a plastic surface. When serum is added, antibodies can attach to the antigen on the solid phase. The presence or absence of these antibodies can be demonstrated when conjugated to an enzyme. Adding the appropriate substrate will detect the amount of bound conjugate which can be quantified. A common ELISA assay is one which uses biotinylated anti-(protein) polyclonal antibodies and an alkaline phosphatase conjugate. For example, an ELISA used for quantitative determination of protein levels can be an antibody sandwich assay, which utilizes polyclonal rabbit antibodies obtained commercially. The antibody is conjugated to alkaline phosphatases for detection. In another example, an ELISA assay to detect trypsin or trypsinogen uses biotinylated anti-trypsin or anti-trypsinogen polyclonal antibodies and a streptavidin-alkaline phosphatase conjugate.

Clearly, many such methods are available to one skilled in the art to ascertain if the protective molecule provides protection, and provides protection at the levels administered to the animal.

The present inventors also contemplate that the isolated sequences from the microorganism of the present invention may be delivered using various vectors and viruses. In an optional embodiment it is possible to provide an adjuvant in the vaccine. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses. Immunostimulatory agents or adjuvants have been used for many years to improve the host immune responses to, for example, vaccines. The vaccines of the present invention may be used in conjunction with an adjuvants, for example, lipopolysaccharides, aluminum hydroxide and aluminum phosphate (alum), saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes. Desirable characteristics of ideal adjuvants may include: (1) lack of toxicity; (2) ability to stimulate a long-lasting immune response; (3) simplicity of manufacture and stability in long-term storage; (4) ability to elicit both CMI and HIR to antigens administered by various routes; (5) synergy with other adjuvants; (6) capability of selectively interacting with populations of antigen presenting cells (APC); (7) ability to specifically elicit appropriate T-cell helper 1 (TH 1) or TH 2 cell-specific immune responses; and (8) ability to selectively increase appropriate antibody isotype levels (for example, IgA) against antigens. An adjuvant used with the present invention need not possess all these characteristics to be used with the present invention.

Another adjuvant which may be used is *E. coli* heat labile enterotoxin (LT). LT has been used to assist in preventing *E. coli* induced diarrhea (See for example Limjuco et al., U.S. Pat. Nos. 4,285,931 and 4,220,584). However, since its early isolation it has been found that its use of LT is greatly limited due to toxicity, and is avoided as an adjuvant unless modified in some manner to reduce toxicity. See Zhang et al. (2009) *Vet. Rex. Commun.* DOI 10/1007/s11259-009-9222-7. Thus there has been effort to avoid the toxicity problem by changing the sequence of the enterotoxin or by truncation. See, e.g., Piazza et al., U.S. Pat. No. 7,291,588. However, it is possible to use a non-mutated LT as an adjuvant without toxicity. Such non-mutated LT is that which is not truncated or otherwise mutated. As a result, an adjuvant non-toxic impact is provided, and at reduced cost in its manufacture.

The vaccine composition may be introduced into an animal, with a physiologically acceptable vehicle and/or adjuvant. Useful vehicles are well known in the art, and include, e.g., water, buffered water, saline, glycine, hyaluronic acid and the like. The resulting aqueous solutions may be packaged for use as is, or lyophilized, the lyophilized preparation being rehydrated prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. In one embodiment of the invention, the protective molecule is encapsulated such that the resulting composition is water resistant. In an embodiment, the molecule is combined with a binder that assists in associating the molecule with feed, which is particularly useful for oral administration. Such a water resistant binding substance can be any substance having such properties. Examples include, without limitation, agarose or other sugar compounds, albumin, alginate or any similar composition.

In another embodiment, protective molecules isolated from a particular strain or biotype can be combined with other sequences and components of other strains or biotypes or diseases to achieve protection against multiple microorganisms. These different microorganism sequences or components may be administered sequentially or progressively or alternately administered simultaneously in an admixture. Sequential or progressive administration of the vaccine compositions of the invention may be required to elicit sufficient levels of immunity to multiple microorganism strains. Single or multiple administration of the vaccine compositions of the invention can be carried out. Multiple administration may be required to elicit sufficient levels of immunity. Levels of induced immunity can be monitored by measuring amount of neutralizing secretory and serum antibodies, and dosages adjusted or vaccinations repeated as necessary to maintain desired levels of protection.

The protective molecules may be "administered" in any suitable manner, including but not limited to, by immersion in a composition or substance containing the protective molecule (as with shrimp, by providing the vaccine in liquid surrounding the shrimp, for example) parenterally, by injection subcutaneously or intramuscularly, into an organ or cavity of the animal, reverse gavage (rectally), and oral, whether per os or ingestion of feed, as well as transdermal or by gas exchange. The vaccine can be administered by any means which includes, but is not limited to, syringes, nebulizers, misters, needleless injection devices, or microprojectile bombardment gene guns (Biolistic bombardment), via a liposome delivery system, naked delivery system, electroporation, viruses, vectors, viral vectors, or an ingestible delivery system wherein the protective molecules are consumed, for example, in feed or water or in any other suitable manner. Oral or immersion administration provides advantages in ease of administration and the capacity to administer the protective molecules to a group of animals. Injection of the protective molecules can be useful with brood stock, that is, adult animals that have reached or are nearing reproductive maturity. The immunogenic preparations and vaccines are administered in a manner compatible with the dosage formulation, and in such amount as will be therapeutically effective, immunogenic and protective.

The quantity to be administered depends on the subject to be treated, including, for example, the capacity of the immune system of the individual to mount a protective response. Suitable regimes for initial administration and booster doses are also variable, but may include an initial administration followed by subsequent administrations. The need to provide an effective amount of the protective molecule will also need to be balanced with cost of providing higher amounts of the protective molecule. A cost effective vaccine is one in which the cost of producing it is less than the value one can obtain from using it.

Measurement and determination of efficacy of any of the compositions and vaccines of the invention may be accomplished by any of the many methods available to one skilled in the art. By way of example, without limitation, where the process involves interference with a target molecule, target molecule suppression can be measured by quantitative RT-PCR or RT-PCR or nucleic acid hybridization or Northern blotting of whole body or specific tissues RNA extracts, using primer sets that extend beyond or are completely removed from the region encompassed by the dsRNA generating primer set.

Where the vaccine involves production of a protein, a straightforward and quick method can be to perform a Western blot analysis of a sample candidate vaccine composition to quantitate the amount of polypeptide or fragment thereof in the sample. There are various options available to the skilled person. In one embodiment, one compares the amount of polypeptide to a standard known to be effective with like polypeptides from other biotypes, and either prepares a vaccine where the level of polypeptide produced is at least at this standard or higher, or may test the vaccine with a test animal.

There is uncertainty whether an aquatic invertebrate, such as shrimp, produce antibodies. While an immune defense response has been observed, it is believed that such animals do not produce antibodies as defined by current immunology dogma. (See, Kurtz, Trends in Immunology, Vol. 25 No. 5, April 2005.) In the event that measurement of antibody production or levels of induced immunity can be monitored by measuring antibody production, or in the interest of measuring production of protective molecules or the disease agent itself, in order to optimize dosages or vaccinations repeated as necessary to maintain desired levels of protection, simple immunoblotting techniques can be used by those skilled in the art. For example, an ELISA can be performed. An ELISA can be performed on a sample collected from an individual vaccinated to determine whether antibodies to a vaccine comprising the sequence, a derivative, a homologue or a variant or fragment thereof generated anti-polypeptide antibodies or to determine whether the vaccine molecule was successfully expressed, using an antibody. The individual's sample is measured against a reference anti-polypeptide antibody.

The effectiveness of the present vaccine may also be evaluated quantitatively (for example, a decrease in a measurement of disease as compared to an appropriate control group) or qualitatively (e.g., isolation of pathogen or virus from tissue or fluids, and where possible to detect, detection of antigen in a tissue sample by an immunoperoxidase assay method, etc.). Analysis of symptoms and measurement of animal weight gain also demonstated lessening of impact of the disease in the presence of a particular dose. In still another example, ranges of doses may be prepared and protective response measured. A candidate vaccine can be formulated at two or three or more different doses to determine the minimum protective dose. For example, when using RP, in addition to measuring IFA titration, qPCR assays can be used to determine the number of genome equivalents present in the vaccine and compared to IFA titer to obtain a GE:RP ratio. Such an assay helps assure uniformity as well. In still another example, such testing indicated that a swine influenza efficacious dose was about $1 \times 10^8$ RP. By way of another example, without limitation, two or three or more dose ranges may be prepared, as in the example below with shrimp and morbidity and mortality measured upon challenge. The dose selected in a preferred embodiment is that which provides protection to the animal which is also cost effective.

Clearly one skilled in the art has many different options available for measuring effectiveness of the vaccine.

With the present invention, it is possible to achieve protection against disease in an aquatic invertebrate, and which protection is provided for longer periods than have been achieved in such animals. Protection periods of more than seven days after at least one challenge or exposure to the pathogenic microorganism have been achieved, and protection of at least two weeks, at least 20 days, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 days or more, have been achieved using the invention. The protective response is also shown here in an embodiment to be specific to the disease as opposed to another disease, and thus demonstrates specific memory.

The following examples are presented by way of illustration and are not intended to be limiting to the scope of the invention.

Example 1

Here described is one method of producing autogenous replicon particle (ARP also referred to by some practitioners as RNA particle or Replicon Particle) In a first experiment, it was confirmed that RP vaccines were capable of producing a foreign antigen in vivo that resulted in an induced immune response in pigs.

Pigs were obtained at 2 weeks of age, weighed, tagged, and randomized into 2 groups of 8 pigs each (Table 3). Prior to vaccination, serum was collected to assure pigs were free of influenza antibodies.

TABLE 3

Design of replicon particle (RP) proof of concept study in pigs.

| Group (n) | Treatment (route) | Dose | Vaccination Schedule |
| --- | --- | --- | --- |
| 1 (8) | RP (IM) (Neg control) | $10^8$ | Day 0 prime, Day 14 boost |
| 2 (8) | HA RP (IM) | $10^8$ | Day 0 prime, Day 14 boost |

Pigs received either an empty RP or an RP expressing the influenza hemagglutinin (HA) protein.

Serum was collected throughout the study for hemagglutination inhibition (HI) assay using the A/Wyoming/03/2003 virus. All pigs were HI negative prior to starting the study and Group 1 pigs remained negative during the study (individual pig data not shown). However a robust and long lasting antibody response to HA protein was induced in Group 2 (Table 4). This response started to appear following the priming dose and elevated quickly after the second dose. By Day 21 all pigs had titers between 1280 and 5120 and maintained this level through termination of the study at 62 days. Although the pigs in this experiment were not challenged with virulent virus, based on previous studies and generally accepted protective level (>40) this level of HI antibody would have been protective.

TABLE 4

HI results (inverse titers) of pigs immunized with RP expressing the influenza HA protein (>40 considered positive). Pigs were immunized on Day 0 and 14. The trial ended on Day 62.

| Pig # | Day −9 | Day 13 | Day 21 | Day 28 | Day 41 | Day 51 | Day 62 |
| --- | --- | --- | --- | --- | --- | --- | --- |
| 4 | 10 | 320 | 2560 | 2560 | 2560 | 2560 | 1280 |
| 8 | 10 | 80 | 2560 | 5120 | 2560 | 2560 | 2560 |
| 11 | 10 | 40 | 2560 | 2560 | 2560 | 2560 | 1280 |
| 18 | 10 | 40 | 2560 | 2560 | 2560 | 2560 | 2560 |
| 20 | 40 | 20 | 5120 | 2560 | 5120 | 5120 | 5120 |
| 25 | 20 | 80 | 2560 | 2560 | 5120 | 5120 | 5120 |
| 26 | 10 | 80 | 2560 | 5120 | 2560 | 2560 | 2560 |
| 30 | 10 | 40 | 5120 | 2560 | 2560 | 2560 | 2560 |

We have successfully shown that RP vaccines can be made that co-express both PRRSV GP5 and M proteins and that a heterodimer is formed. Erdman M M, Harris D L, Kamrud K I. Replicon particle co-expression of PRRSV GP5 and M proteins. *Proc CRWAD* 2006. Following successful expression in vitro, a pig trial was conducted to determine if the GP5-M RP vaccine would induce an immune response in pigs. Pigs 2-3 weeks of age were obtained from a PRRSV negative source. Pigs were tagged, weighed, and randomized into 2 groups of 8 (Table 5). Serum was collected prior to vaccination to assure pigs had no antibodies to PRRSV.

TABLE 5

Previous PRRSV RP proof of concept study.

| Group (n) | Treatment (route) | Dose | Vaccination Schedule |
| --- | --- | --- | --- |
| 1 (8) | RP Control (IM) | $10^8$ | Day 0 prime, Day 14 boost |
| 2 (8) | GP5-M RP (IM) | $10^8$ | Day 0 prime, Day 14 boost |

Pigs were vaccinated with either an empty RP or an RP co-expressing PRRSV GP5 and M proteins.

All pigs were challenged on Day 48 with a homologous PRRSV strain (HLV013) intramuscular with 2 ml of $10^6$ $TCID_{50}$. Neither group had virus neutralizing antibodies on Marc 145 cells prior to challenge although Western blotting indicated antibodies were present to the PRRSV proteins. Following challenge, 3 of 8 pigs in the vaccinate group and 0 of 8 pigs in the control group had neutralizing titers within 7 days. All pigs were necropsied 14 days after challenge. At necropsy 5 of 8 in the vaccinate group and 4 of 8 in the control group had neutralizing titers. However the geometric mean titers (GMT) was higher in the vaccinate group (GMT=27.8) compared to the control group (GMT=9.5). Virus titration of lung lavage indicated that 7 of 8 control pigs were virus positive and only 4 of 8 vaccinate pigs were virus positive. Lung lesion scoring showed less gross pathology in the vaccinate group (mean score of 16.3) compared to the control group (mean score of 22.3).

Results and Accomplishments
ARP Vaccine Construction

The entire vaccine development process took three weeks from PRRSV positive serum sample to formulated GP5 and M single promoter ARP vaccines and an additional week to produce the GP5/M double promoter ARP vaccine. Due to the fact that speed of development was important to us in this experiment we opted to conduct the trial by co-injecting the GP5 and M single promoter ARP since they took less time to produce and posed less technical challenges. However both the single promoter and double promoter approaches are viable options and that both are more rapid than the time it generally takes to develop a new conventional autogenous vaccine requiring isolation and growth of the virus.

PCR can be performed on a sample to both provide a positive diagnosis of PRRS and also generate cDNA of the genes needed to make the ARP vaccine. It is also anticipated that this entire process can be performed in less time than it generally takes for a pig producer to get a traditional autogenous vaccine made.

To develop the new ARP vaccine, a large swine producer that had pigs suffering from clinical PRRSV was identified. Serum samples from diseased animals were sent to Iowa State University. RT-PCR was used both to confirm diagnosis and produce cDNA of genes targeted for vaccine production. Specific primers were used to amplify both the PRRSV GP5 and M genes, ORF 5 and 6 respectively. Although not needed to make the vaccine, the live virus was isolated in order to prepare a traditional killed autogenous vaccine and used for challenging the pigs. The isolate was referred to as PRRSV strain Pennway.

Figure 3:
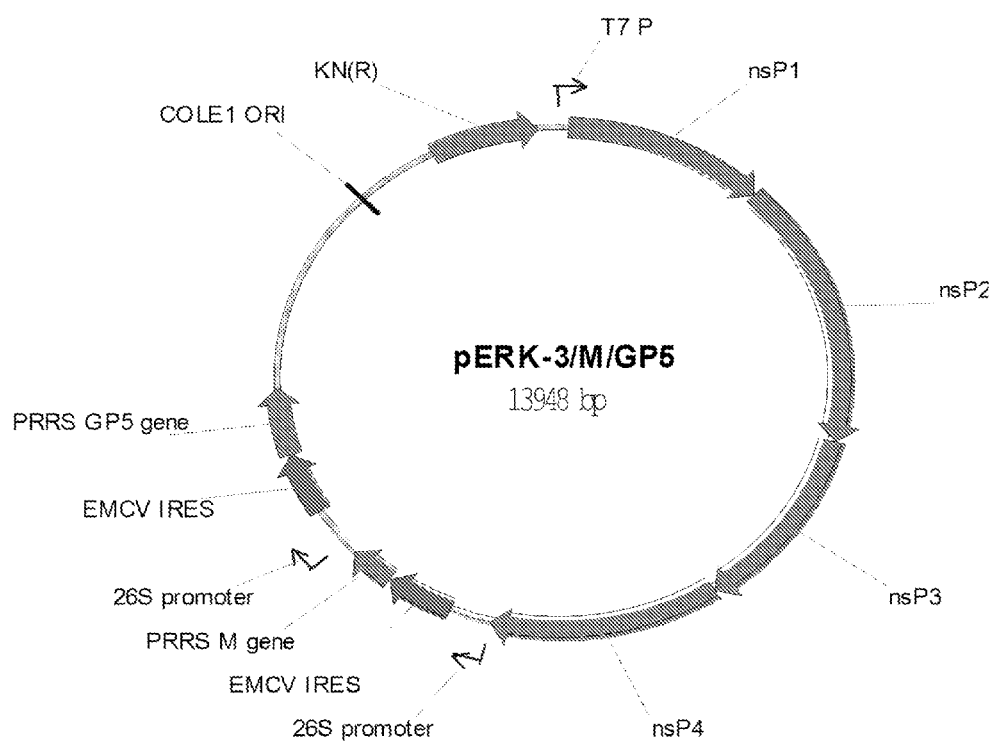
FIG. 3 is a map of the vector pERK-3/M/GP5.

The PRRSV GP5 and M genes were cloned into replicon vectors that are based on the live attenuated vaccine strain of VEE known as TC-83 (FIG. 3). The GP5 and M replicon vectors were analyzed by both IFA and Western blot to confirm expression of desired proteins. The replicons were then packaged into particles via co-electroporation with helper RNAs to produce ARP. ARP were harvested from culture fluids and the infectious titer of the ARP preparation was measured by antigen-specific IFA and tested in a CPE assay to assure the absence of replication competent virus.

Vaccine Formulations

The placebo vaccine consisted of 2 ml of sterile PBS (Hy-Clone Laboratories).

The ARPs had initial titers of 2.11e9/ml for the GP5 ARP and 3.56e9 for the M ARP. Each ARP was diluted to a titer of 1e8/ml using PBS. Each dose consisted of 1 ml of GP5 ARP and 1 ml of M ARP co-injected in the same syringe.

The inactivated PRRSV vaccine was derived from the same strain used to produce the ARP vaccine. The virus was grown to 85% CPE on Marc-145 cells and harvested from the supernatant. The virus titer was determined to be 2.7e5 $TCID_{50}$/ml. The virus was heat inactivated at 65 degrees C. for 90 minutes. A sample of the prep was inoculated onto Marc-145 cells to confirm the lack of viable virus. The lysate was formulated with Emulsigen-D adjuvant (MVP laboratories, Ralston, Nebr.) by adding 1.6 ml of the lysate with 0.4 ml of adjuvant per dose.

The PRRSV MLV vaccine was Inglevac PRRS ATP (Boehringer Ingelheim Vetmedica, Inc). The vaccine was used as directed by the manufacturer which indicated giving a single 2 ml dose of vaccine.

Pig Trial

Three week old pigs were obtained from a farm in Iowa with no history of PRRSV infection based on clinical signs and serology. Pigs were ear tagged, weighed, and randomized into five groups of ten pigs each in BSL-2 animal facilities at Iowa State University. A description of groups is given in Table 5 and a timeline for the vaccination-challenge study is shown in Table 6. Group 1 contained strict negative control pigs that were neither vaccinated nor challenged. All pigs in Groups 2, 3, and 4 were vaccinated intramuscular (IM) on Day 0 and again on Day 28. Group 2 received the placebo vaccine, Group 3 the ARP vaccine, and Group 4 the inactivated PRRSV vaccine. Group 5 received one dose of the MLV vaccine on Day 0.

TABLE 6

Groups in PRRSV vaccination-challenge study

| Group | Pigs (n) | Treatment | Route | PRRSV challenge |
|---|---|---|---|---|
| 1 | 10 | Strict negatives | NA | NA |
| 2 | 10 | Placebo | IM | IN |
| 3 | 10 | ARP PRRSV GP5-M | IM | IN |
| 4 | 10 | Inactivated PRRSV | IM | IN |
| 5 | 10 | MLV PRRSV | IM | IN |

PRRSV = porcine reproductive and respiratory syndrome virus, M = matrix protein, GP5 = glycoprotein 5, ARP = autogenous replicon particles, MLV = modified live virus NA = not applicable, IM = intramuscular, IN = intranasal Pigs were challenged IN on Day 56 with 2 ml of $1 \times 10^5$ $TCID_{50}$/ml of virulent PRRSV strain Pennway. Pigs were monitored for clinical signs including respiratory distress, lethargy, and recumbancy following challenge but none were noted. Pigs were euthanized 21 days after challenge, a necropsy performed, and tissues collected for laboratory testing including quantitative gross lung lesion scoring, histopathology, IDEXX ELISA, virus titration, and virus neutralization.

TABLE 7

Time course for vaccination-challenge trial

| | |
|---|---|
| Day −28 | Creation of ARP vaccines begins |
| Day −21 | Pigs are born on the source farm |
| Day −7 | Pigs arrive at ISU (3 weeks old), collect blood |
| Day 0 | First vaccination |
| Day 14 | Collect blood |
| Day 28 | Collect blood, Second vaccination |
| Day 42 | Collect blood |
| Day 49 | Collect blood, challenge with virulent virus |
| Day 49-70 | Monitor for clinical signs daily |
| Day 56 | Collect blood |
| Day 63 | Collect blood |
| Day 70 | Euthanize and necropsy pigs. Evaluate lesions, collect tissues for diagnostic testing and histopathology. |

Pathology

At necropsy, gross pathology lung lesions were determined by a treatment blinded, board certified veterinary pathologist as previously described by Halbur et al. Halbur P G, Paul P S, Meng X J, Lum M A, Andrews J J, Rathje J A. Comparative pathogenicity of nine US porcine reproductive and respiratory syndrome virus (PRRSV) isolates in a five-week-old cesarean-derived, colostrum-deprived pig model. *J Vet Diagn Invest* 1996; 8:11-20.

Figure 4:
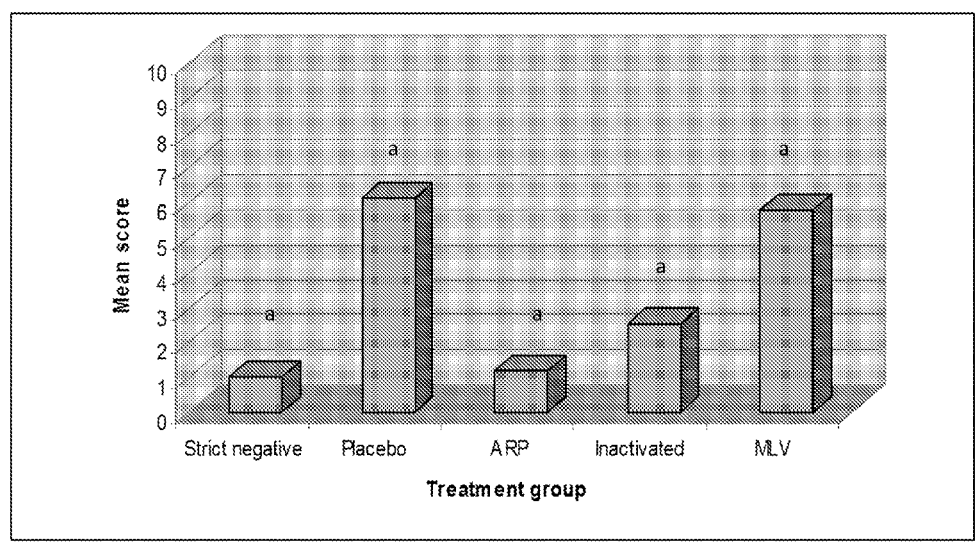
FIG. 4 is a graph showing total gross lung score in different treatment groups. Treatment groups with different letters are significantly different (ANOVA, $p<0.05$).
Figure 5:
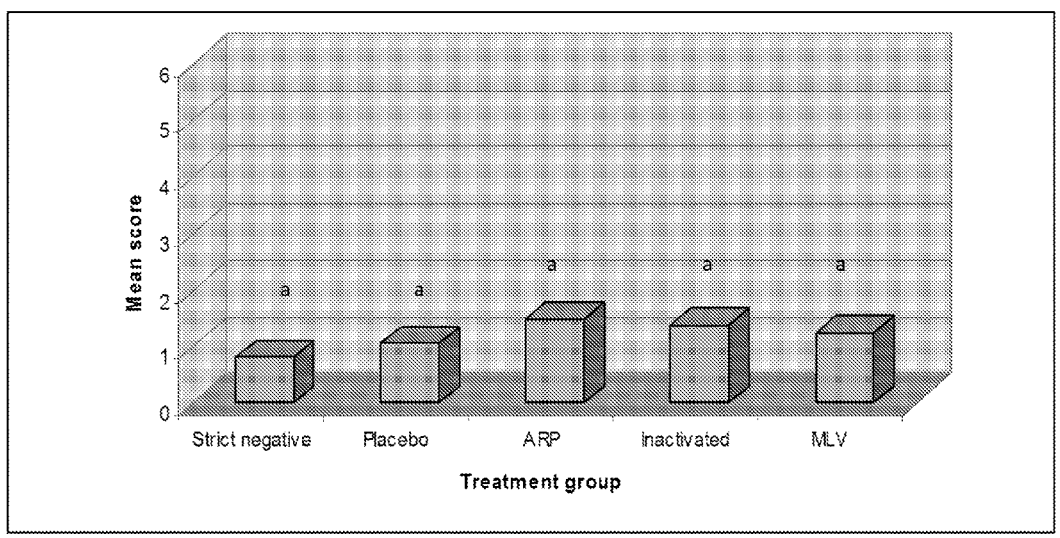
FIG. 5 is a graph showing interstitial pneumonia scores in different treatment groups. Treatment groups with different letters are significantly different (ANOVA, $p<0.05$).
Figure 7:
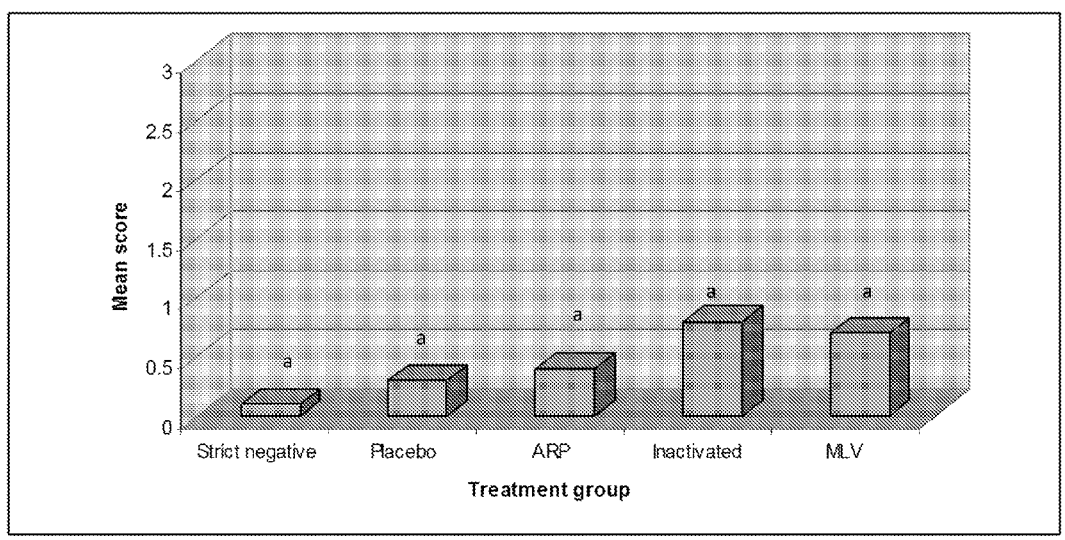
FIG. 7 is a graph showing a summary of heart pathology scores. Treatment groups with different letters are significantly different (ANOVA, $p<0.05$).
Figure 8:
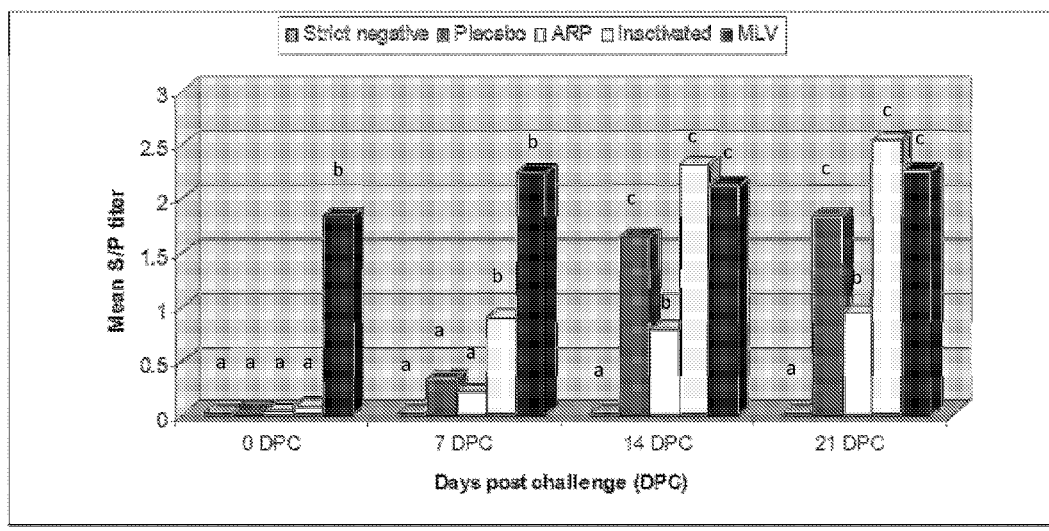
FIG. 8 is a graph showing mean IDEXX ELISA S/P titer per group. Groups with different letters are significantly different (ANOVA, $p<0.01$) within day post challenge. The bars of each group are in the order listed: strict negative, placebo, ARP, inacivated and MLV.
Figure 9:
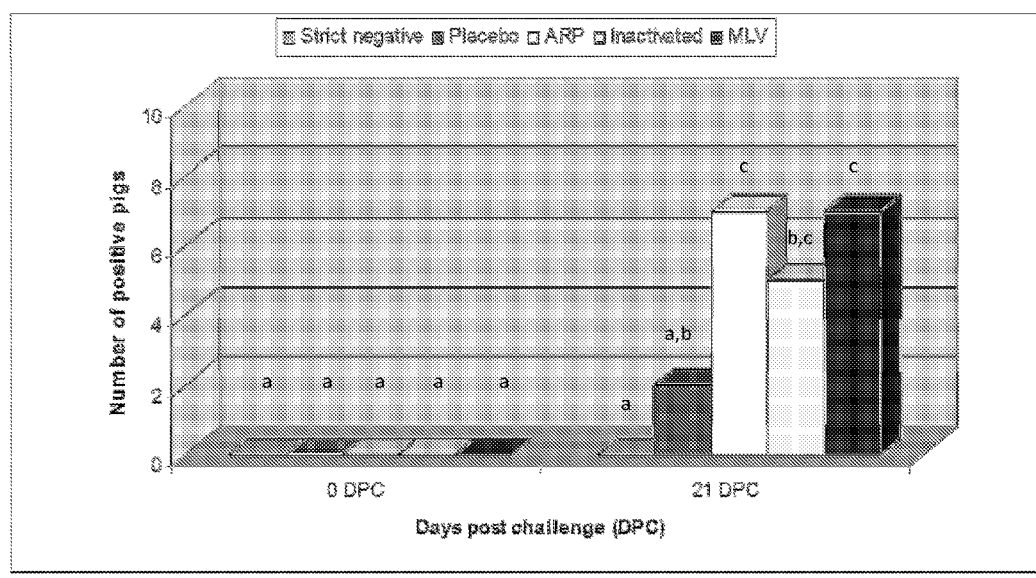
FIG. 9 is a graph showing the number of pigs out of ten per group with a FFN titer $\geq 4$. Groups with different letters are significantly different (Chi-square, $p<0.05$) within day post challenge. The bars of each group are in the order listed: strict negative, placebo, ARP, inacivated and MLV.
Figure 10:
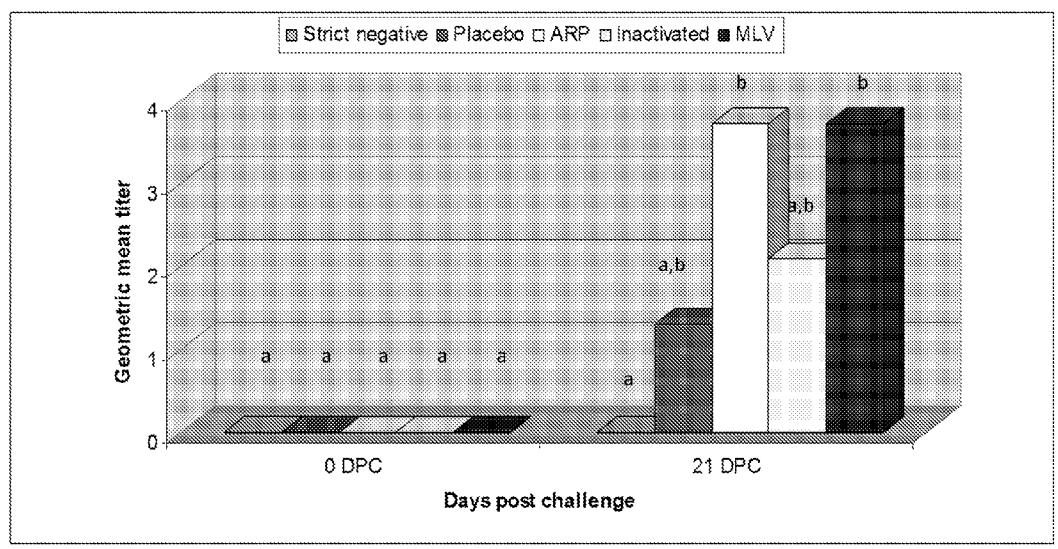
FIG. 10 is a graph showing geometric mean FFN titer by group. Groups with different letters are significantly different (ANOVA, $p<0.01$) within day post challenge. The bars of each group are in the order listed: strict negative, placebo, ARP, inacivated and MLV.
Figure 11:
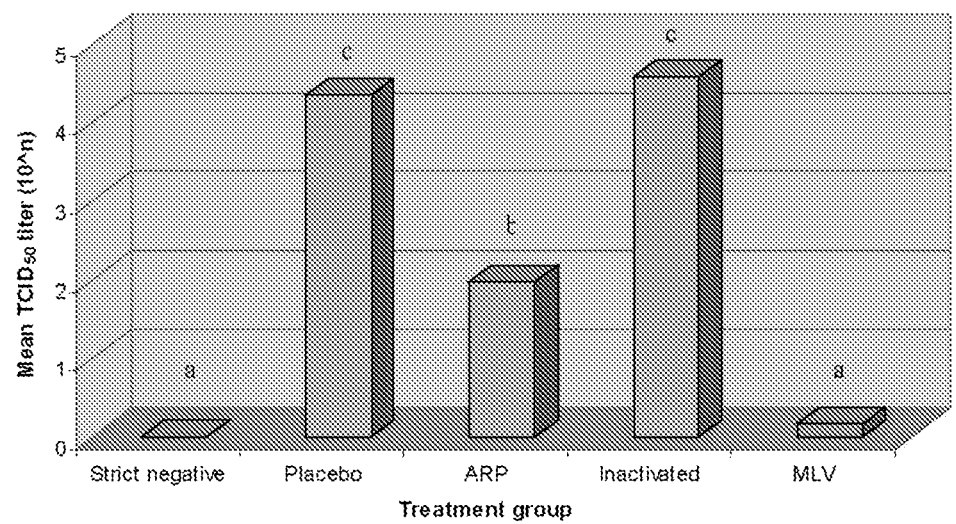
FIG. 11 is a graph showing live virus titration at 7 DPC. Groups with different letters are significantly different (ANOVA, $p<0.01$).
Figure 12:
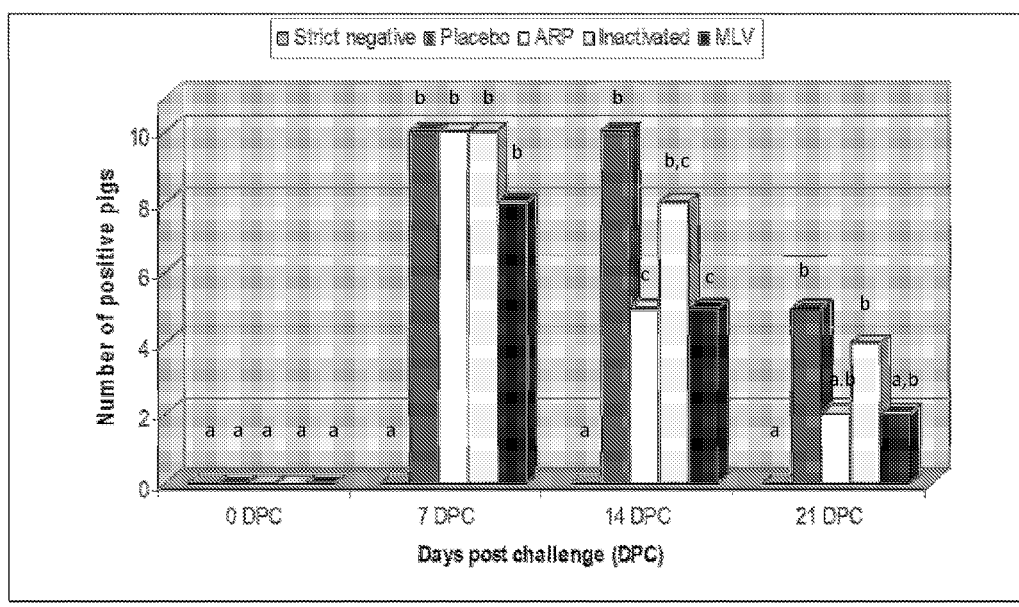
FIG. 12 is a graph showing the number of pigs out of ten per group PRRSV positive serum via RT-PCR. Groups with different letters are significantly different (Chi-square, $p<0.05$) within day post challenge. The bars of each group are in the order listed: strict negative, placebo, ARP, inacivated and MLV.
Figure 13:
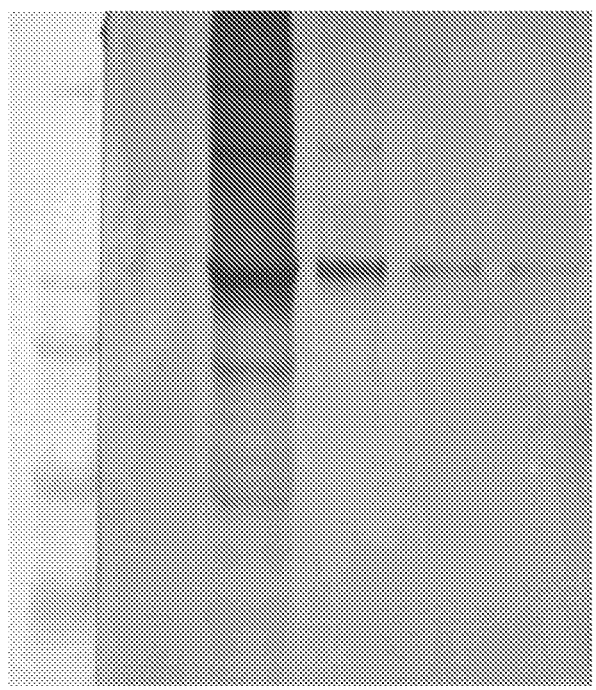
FIG. 13 is a Western blot confirming recombinant HA expression. Lane 1 is the ladder; lane 2 the Vero lysate (negative control); lane 3, recombinant HA (28.5 µg/ml); Lane 4: Recombinant HA (1.14 µg/ml); Lane 5: Recombinant HA (0.57 µg/ml); Lane 6: Recombinant HA (0.38 µg/ml).

Briefly, each section of the lung was assigned a number and the lung score represents the percentage of that lobe with evidence of pneumonia. The scores for each lobe are then added together to get the overall lung score for that pig. The lung pathology in this experiment was rather mild and is summarized in FIG. 4 as the total lung score by group. Histopathology was also conducted on lung and heart sections as described by Halbur et al., supra These results are summarized in FIGS. 5-7. The interstitial pneumonia is the average of four different sections per pig using a scale of 0 (normal) to 6 (severe and diffuse). Results indicated no statistical differences between groups. Lung lymphoid hyperplasia was examined on the same sections with a scale of 0 (normal) to 6 (severe hyperplasia). Results indicated that both the placebo and inactivated vaccine groups had statistically (p<0.05) greater hyperplasia when compared to the strict negative group. No other statistical differences were noted. The heart section was examined for signs of infection on a scale of 0 (normal) to 3 (severe myocarditis). Results indicated no statistical differences between groups.

The pathology results indicate few statistical differences despite the fact that other assays we conducted indicate a successful challenge. Lesions and clinical signs induced in PRRSV studies can vary greatly, or be nearly absent as seen here, due to a variety of reasons including strain differences. This contributes to the fact that other measures such as virema and antibody assays discussed below are considered the gold standard for evaluating PRRSV vaccines.

IDEXX HerdChek PRRS 2XR ELISA

The IDEXX ELISA detects antibodies to the nucleopcapsid (N) protein of PRRSV. These antibodies dominate the early response to PRRSV although they do not provide protection from disease. Previous work has also correlated the S/P (sample to positive, the ratio of sample signal to background that is commonly used with IDEXX ELISA) titers to level of viremia and in this way the titers can be used to compare level of infection between groups. Johnson W, Roof M, Vaugh E, Christopher-Hennings J, Johnson C R, Murtaugh M. Pathogenic and humoral immune response to porcine reproductive and respiratory syndrome virus (PRRSV) are related to viral load in acute infection. *Veterinary Immunology and Immunopathology* 2004; 102:233-47.

Serum samples were collected from all pigs on 0, 7, 14, and 21 days post challenge. Samples were sent to South Dakota State University for testing. An S/P ratio of ≥0.40 is considered positive. The results are shown in FIG. 8 as mean S/P ratio per group. The results indicate that on the day of challenge all pigs in Groups 1-4 remained negative. This assured us that we did not have lateral introduction of live virus during the study. All pigs in Group 5 were IDEXX positive on the day of challenge which is to be expected since the N protein is a major part of the MLV vaccine. All pigs in the ARP group remained negative prior to challenge reinforcing the idea that this vaccine can be used in conjunction with the IDEXX ELISA to differentiate infected from vaccinated animals (DIVA). Groups 2-4 seroconverted by 14 days post challenge. However the ARP group remained signicantly lower than the other treatment groups through necropsy indicating a lower level of infection in this group. This comparison was not possible in the MLV group since it was positive prior to challenge. The strict negatives remained negative throughout the study.

Fluorescent Focused Neutralization Assay

The fluorescent focused neutralization (FFN) assay detects serum neutralizing antibodies against PRRSV. Serum samples were collected from all pigs on 0, 7, 14, and 21 days post challenge. Samples were sent to South Dakota State University for testing as previously described. The test virus used was PRRSV strain Pennway and an inverse titer ≥4 was considered positive. The number of positive pigs in each group is summarized in FIG. 9. There no positives in any group on day of challenge. However after challenge the ARP and MLV groups showed more pigs positive by necropsy when compared to to the inactivated and placebo groups. All pigs in the strict negative group remained negative throughout the study. With more positive pigs it is not surprising that the mean neutralizing titers of the ARP and MLV groups were higher than the other treatments as shown in FIG. 10.

Although our previous work has indicated that expressed PRRSV GP5 and M can induce neutralizing antibody prior to challenge we did not see that in this study. However it is possible that this is due to glycosylation of the GP5 used for this study. This was a new vaccine created from a field strain that tend to be highly glycosylated. Although there were not neutralizing antibodies prior to challenge, we did note a priming effect in the ARP group similar to the MLV group as evidenced by the differences between groups post challenge.

Live Virus Titration

Serum samples collect at 0, 7, 14, and 21 DPC as well as bronchial alveolar lavage (BAL) fluid collected at necropsy were tested for the presence of live PRRSV as previously described. Briefly, samples were diluted 10-fold on 96 well plates containing confluent Marc-145 cells. Each clinical sample was plated in quadruplicate. Plates were incubated at 37° C. and 5% $CO_2$ for 7 days, or until no new CPE was observed. $TCID_{50}$/ml titers were calculated using the Reed-Muench equation. The detection limit was 5.6e1 $TCID_{50}$/ml.

All groups were negative for live virus on 0 DPC and the strict negative group remained negative throughout the study. By 7 DPC virus was detected in the four challenged groups and significant differences in viremia were noted (FIG. 11). There was no detectable live virus in the serum at 14 and 21 DPC. Testing of the BAL fluid indicated only one positive sample in Groups 2 and 5 and two positive samples in Groups 3 and 4 (Data not shown).

RT-PCR

RT-PCR was conducted on serum samples collected at 0, 7, 14, and 21 DPC as previously described. Briefly, viral RNA was extracted using the Qiagen Virus Spin Kit. The extract was then tested in duplicate using primers specific for the ORF7 gene of PRRSV which codes for the N protein. The results are summarized as the number of positive pigs in each group (FIG. 12).

While PCR is another assay to detect viremia, it is not surprising that the PCR and live virus titration results do not match. One method detects live virus while the other only detects nucleic acid which could possibly be present in the absence of live virus. The PCR results indicate that by 14 DPC the ARP and MLV groups had significantly fewer viremic pigs compared to the placebo group.

Example 2

In this study, the alphavirus replicon is derived from the TC-83 strain of the alphavirus Venezuelan Equine Encephalitis Virus (VEEV). In a previous study, a VEEV replicon vaccine expressing the HA gene from a human H5N1 isolate protected chickens from lethal challenge. Schultz-Chemy S, Dybing J K, Davis N L, Williamson C, Suarez D L, Johnston R, Perdue M L. Influenza virus (A/HK/156/97) hemagglutinin expressed by an alphavirus replicon system protects chickens against lethal infection with Hong Kong-origin H5N1 viruses. *Virology*. 2000 Dec. 5; 278(1):55-9. PubMed PMID: 11112481. Recently, our group became the first to evaluate VEEV replicon particle vaccines in swine. Erdman M M, Kamrud K I, Harris D L, and Smith J, 2010, "Alphavirus Replicon Particle Vaccines Developed for Use in Humans Induce High Levels of Antibodies to Influenza Virus Hemagglutinin in Swine: Proof of concept", *Vaccine* 28:594-596. The objective of this study was to evaluate replicon-expressed recombinant novel H1N1 HA protein as a swine vaccine in a vaccination-challenge model.

Materials and Methods

Novel H1N1 HA Replicon Subunit Vaccine Production

The hemagglutinin (HA) nucleotide sequence was retrieved from the Global Initiative on Sharing Avian Influenza Data (GISAID) database. The gene was synthesized by a commercial company (DNA2.0, Menlo Park, Calif., USA) with unique AscI and PacI restriction sites engineered at the 5' and 3' ends, respectively. The HA gene was cloned into the AscI/PacI sites of the pVEK (TC-83) replicon vector (Hooper J W, Ferro A M, Golden J W, Silvera P, Dudek J, Alterson K, Custer M, Rivers B, Morris J, Owens G, Smith J F, and Kamrud K I, 2009, "Molecular Smallpox Vaccine Delivered by Alphavirus Replicons Elicits Protective Immunity in Mice and Non-Human Primates", Vaccine 13(13)). and an optimized construct was selected as previously described. (Kamrud K I, Custer M, Dudek J M, Owens G, Alterson K D, Lee J S, Groebner J L, Smith J F. Alphavirus replicon approach to promoterless analysis of IRES elements. *Virology.* 2007 Apr. 10; 360(2):376-87. Epub 2006 Dec. 6. PubMed PMID: 17156813; PubMed Central PMCID: PMC1885372). The HA gene was then sequenced to ensure the proper sequence was maintained through the cloning process. RNA transcripts were produced in vitro as previously described (Kamrud et al. (2007), supra. Replicon RNA was mixed with Vero cells in electroporation cuvettes and pulsed. Cells were incubated overnight and then lysed using RIPA buffer (Pierce, Rockford, Ill., USA). Resulting lysate was tested for protein expression by Western blot and HA protein concentration was determined by a novel H1N1 HA-specific ELISA. Lysate was diluted to the specified HA concentration and vaccine was adjuvanted with Emulsigen-D (MVP Technologies, Omaha, Nebr., USA).

Western Blot Analysis

Vero cell lysate containing recombinant HA protein was separated by running on a 12% SDS-PAGE gel (Invitrogen, Carlsbad, Calif., USA) and was then transferred to a PVDF membrane (Invitrogen, Carlsbad, Calif.). The ladder used was the SeeBlue Plus2 Pre-Stained Standard (Invitrogen, Carlsbad, Calif., USA). After transfer, membrane was blocked with 5% non-fat dry milk at room temperature. Membrane was incubated with swine polyclonal anti-HA for two hours, washed three times, followed by incubation with goat anti-swine IgG horseradish peroxidase conjugate (Immuno-Jackson Research Laboratories, Inc, West Grove, Pa., USA) for one hour, and washed three times. Detection was performed using TMB substrate (KPL, Gaithersburg, Md., USA).

Animal Studies

Pigs free of swine influenza virus (SIV) and porcine reproductive and respiratory syndrome virus (PRRSV) were obtained at three weeks of age. Pigs were randomized and separated into 4 groups of 5 pigs each. Prior to vaccination, serum was collected and tested by the homologous hemagglutination inhibition (HI) assay against the novel H1N1 A/California/04/2009 strain to confirm negative antibody status. Sera were collected throughout the study and tested by this same HI assay to monitor seroconversion post-vaccination. A prime/boost vaccination schedule was followed. The first dose of vaccine was given to pigs at approximately 4 weeks of age on day 0. On day 21 pigs received booster vaccination, with challenge on day 47 and necropsy on day 52. Pigs received either phosphate buffered saline (PBS) (Group 1) or different concentrations of novel H1 HA recombinant protein (Groups 2-4,). Pigs were challenged intratracheally with virulent A/California/04/2009 (CDC #2009712047) at a dose of $2 \times 10^5$ $TCID_{50}$/ml. Nasal swabs were collected daily for live virus isolation beginning on day of challenge and continuing until study completion 5 days post-challenge. Pigs were weighed immediately before challenge and again at necropsy for determination of average daily gain. At necropsy, gross lung lesion consolidation was determined by a board-certified pathologist. Lung tissue was fixed in formalin for SIV immunohistochemistry (IHC) and histopathological analysis. Bronchoalveolar lavage fluid (BALF) was collected from lungs for live virus isolation. This animal study was approved by the Iowa State University Institutional Animal Care and Use Committee.

Gross Lung Lesion Scoring, Histopathology, and SIV Immunohistochemistry

A single board-certified veterinary pathologist who was blinded to group treatments, performed gross lung scoring, histopathological analysis, and SIV Immunohistochemistry (IHC) analysis. At necropsy, each lung lobe affected by pneumonia was visually estimated, and a total percentage for the entire lung was calculated based on weighted proportions of each lobe to the total lung volume (Halbur P G, Paul P S, Frey M L, Landgraf J, Eernisse K, Meng X J, Lum M A, Andrews J J, Rathje J A. Comparison of the pathogenicity of two US porcine reproductive and respiratory syndrome virus isolates with that of the Lelystad virus. *Vet Pathol.* 1995 November; 32(6):648-60. PubMed PMID: 8592800). Tissue samples from the trachea and all lung lobes were collected and fixed in 10% formalin. Tissues were routinely processed and stained with hematoxylin and eosin. Lung samples were scored according to the method used by Vincent et al. (Vincent A L, Ma W, Lager K M, Janke B H, Webby R J, Garcí a-Sastre A, Richt J A. Efficacy of intranasal administration of a truncated NS1 modified live influenza virus vaccine in swine. *Vaccine.* 2007 Nov. 19; 25(47):7999-8009. Epub 2007 Sep. 29. PubMed PMID: 17933442; PubMed Central PMCID: PMC2099695). Swine influenza virus IHC was done according to the method described by Vincent et al. (Vincent L L, Janke B H, Paul P S, Halbur P G. Demonstration of swine influenza virus in formalin-fixed, paraffin-embedded tissues by use of an immunohistochemical test. Proceedings of the 14th IPVS Congress. 1996; 97). All tissue preparation and staining was done by the Iowa State University Veterinary Diagnostic Laboratory.

Live Virus Isolation

Live virus titers were determined from nasal swabs and live virus isolation performed on bronchoalveolar lavage fluid (BALF) samples. Briefly, nasal swabs and BALF samples were thawed and centrifuged to remove cellular debris. The resulting supernatant was diluted 10-fold in 96 well plates in Dulbecco's Modified Eagle Medium (DMEM) (Gibco, Carlsbad, Calif., USA) containing 1% antibiotic-antimycotic (Gibco, Carlsbad, Calif., USA) and 1% L-glutamine (Mediatech, Manassas, Va., USA). After dilutions were made, 1000 was transferred from each well into respective wells of a 96 well plate which contained a monolayer of swine testicle (ST) cells. Plates were incubated at 37° C. until no further CPE was observed, typically 3-5 days. Wells displaying CPE were considered positive, and titers were calculated using the $TCID_{50}$/ml method of Reed-Meunch. (Reed L T and Muench H. A simple method of estimation of 50% end points. American journal of Hygiene. 27; 493-497. 1938)

Hemagluttination Inhibition Assay

Antibodies to influenza virus were measured by hemagglutination inhibition (HI) assay run by the University of Minnesota Veterinary Diagnostic Laboratory following standard laboratory protocol. Briefly, sera were treated with receptor-destroying enzyme, heat inactivated, adsorbed with 20% turkey erythrocytes, and centrifuged. Supernatants were then serially diluted in V-shaped well microtiter plates with an equal volume containing 4-8 agglutinating units of A/California/04/2009 and plates were incubated at room temperature before addition of 0.5% turkey erythrocytes. Titer was defined as the reciprocal of the maximal dilution at which hemagglutination was inhibited.

Direct Antigen Capture ELISA

Unknown samples, negative controls, and purified novel H1 protein (Protein Sciences, Meriden, Conn., USA) were directly captured to NUNC Maxisorp (Rochester, N.Y., USA) 96-well microplates by diluting with capture buffer (50 mM Carbonate/Bicarbonate, pH 9.6) and incubated overnight at 4° C. (100 μl/well). The microplates were washed four times with wash buffer (20 mM Phosphate Buffered Saline, 0.05% Tween-20, pH 7.2). The plates were blocked with 1.25% non-fat dry milk in capture buffer for 1 hour at 37° C. (200 μl/well). After four washes, pig polyclonal anti-HA was added to wells (100 μl) and incubated for 1 hour at 37° C. (diluted 1/500 in wash buffer containing 1.25% NFDM). Following four washes, goat ant-pig IgG-HRP labeled (Jackson ImmunoResearch, West Grove, Pa., USA) was added to the wells (100 μl) and incubated for 1 hour at 37° C. (diluted 1/2000 in was buffer containing 1.25% NFDM). Four final washes were performed prior to the addition of 100 μl of TMB substrate (KPL, Gaithersburg, Md., USA) and incubation at 37° C. for 20 minutes. Absorbance values were measured at 620 nm and a standard curve was plotted with the purified novel H1 protein. Linear regression analysis of the standard curve was used to calculate the novel H1 concentrations in the unknowns.

Statistical Analysis

Single factor analysis of variance (ANOVA) was used to analyze homologous HI titers, macroscopic and histopathological lung scores, IHC and BALF results, log 10 transformed nasal swab viral titers, and ADG (JMP 8.0.1, SAS Institute Inc., Cary, N.C., USA). Statistical significance was set at p<0.05.

Results

Vaccine Preparation

The novel H1N1 HA gene was inserted into the alphavirus replicon platform according to the methods listed previously. Nucleotide sequencing after insertion confirmed the correct HA gene sequence had been maintained throughout the cloning process. Western blotting performed on protein lysate confirmed expression of the novel HA protein at all the varying HA doses used in vaccine preparation for the animal study. The HA concentration was determined by novel HA ELISA and diluted to the specified HA concentration (Table 8). See FIG. 13.

TABLE 8

Design of novel H1N1 recombinant HA vaccine study.

| Group | Vaccine | HA concentration/dose |
|---|---|---|
| 1 | Sham | NA |
| 2 | Recombinant HA | 1.14 μg |
| 3 | Recombinant HA | 0.57 μg |
| 4 | Recombinant HA | 0.38 μg |

Pigs received either sham vaccine (PBS, Group 1) or varying doses of HA antigen (Groups 2-4). All vaccines were given intramuscularly as 2 ml doses on days 0 and 21.

Antibody Titers

Post-vaccination sera were tested for specific antibody response by the homologous HI assay. Hemagglutination inhibition titers were not seen in vaccinated pigs after one dose, but were all positive (≥1:40), except for a single pig in Group 2, at 7 and 14 days post-boost vaccination (data not shown). On the day of challenge, homologous HI titers were significantly higher in Groups 2-4 than Group 1 (Table 9).

TABLE 9

Summary of serum antibody titers, average macroscopic and microscopic lung involvement, immunohistochemistry (IHC), and average daily gain (ADG).

| Group | HI Titers[a] | % Pneumonia[b] | Histopathologic Score[c] | Lung IHC[d] | ADG[e] |
|---|---|---|---|---|---|
| 1 | <10 | 15.6 ± 5.4 | 1.8 ± 0.1 | 5/5 | 1.76 ± 0.2 |
| 2 | 121* | 1.4 ± 0.9* | 0.8 ± 0.2* | 1/5* | 2.56 ± 0.68 |
| 3 | 184* | 0.2 ± 0.2* | 0.6 ± 0.2* | 0/5* | 2.64 ± 0.22* |
| 4 | 106* | 1.8 ± 1.1* | 0.8 ± 0.2* | 1/5* | 2.45 ± 0.34* |

[a]Geometric mean homologous HI titers
[b]Group mean ± standard error
[c]0-3, group mean ± standard error
[d]Number of positive samples per group
[e]ADG post-challenge in pounds, group mean ± standard error
*Values are significantly different from non-vaccinates (Group 1) within a column at $p < 0.05$ Pathological Evaluation At necropsy, lungs exhibited macroscopic dark purplish-red consolidated lesions located mainly in the cranioventral lobes. Lungs taken from Groups 2-4 exhibited significantly lower lesion scores and consolidation than pigs in Group 1 (Table 3). There was also a significant reduction in pathological scores in all vaccinated groups compared to the non-vaccinated group (Table 3). The lung sections taken from non-vaccinated Group 1 pigs had approximately 50% of the airways affected by bronchiolar epithelial disruption and peribronchiolar lymphocytic cuffing. The vaccinated Groups 2-4 demonstrated only occasional affected airways with light cuffing. Swine influenza virus IHC was also performed on lung sections. All 5 lungs taken from non-vaccinated Group 1 pigs were positive for influenza antigen, while only 2 pigs in total from the vaccinated Groups 2-4 were positive. Additionally, SIV IHC was done on trachea samples taken from each pig at necropsy (data not shown). Although there were positive trachea IHC samples in all groups, there was no significant differences between vaccinated and non-vaccinated groups. Positive trachea IHC results correlate with what was previously reported on pathogenesis of novel H1N1 in ferrets. (Munster V J, de Wit E, van den Brand J M, Herfst S, Schrauwen E J, Bestebroer T M, van de Vijver D, Boucher C A, Koopmans M, Rimmelzwaan G F, Kuiken T, Osterhaus A D, Fouchier R A. Pathogenesis and transmission of swine-origin 2009 A(H1N1) influenza virus in ferrets. *Science.* 2009 Jul. 24; 325(5939):481-3. Epub 2009 Jul. 2. PubMed PMID: 19574348)

Virus Isolation

No live influenza virus was detected one day post-challenge from nasal swabs (Table 4). On day 2 post challenge live influenza virus was detected in Groups 1, 3, and 4, although there were no significant differences between mean group viral titers. On day 3 post-challenge Groups 2 and 4 had significantly lower titers than did Group 1. On both days 4 and 5 Groups 2-4 all exhibited lower titers than Group 1. No live virus was detected in nasal swabs from any pigs in Group 2 for the duration of the challenge period. Similarly, there was a significant reduction in the number of positive BAL samples between groups (Table 3). By 5 days post-challenge, only a total of 3 vaccinated pigs had detectable live virus in BAL samples, while all 5 pigs in the non-vaccinated group were virus isolation positive.

Average Daily Gain

All pigs were weighed on the day of challenge and again at necropsy. Groups 3 and 4 had significantly higher average daily gain (ADG) over the 5 day period following challenge than did Group 1. Group 2 did exhibit higher ADG but was not significantly higher than Group 1 (p=0.08).

TABLE 10

Summary of live virus isolation from nasal swabs and bronchoalveolar lavage (BAL).

| | Nasal Swab[a] | | | | | BAL[b] |
|---|---|---|---|---|---|---|
| Group | 1 DPC[c] | 2 DPC | 3 DPC | 4 DPC | 5 DPC | 5 DPC |
| 1 | 0 | 0.85 ± 0.53 | 2.55 ± 0.66 | 3.05 ± 0.18 | 3.05 ± 0.24 | 5/5 |
| 2 | 0 | 0 | 0* | 0* | 0* | 2/5 |
| 3 | 0 | 1.05 ± 0.07 | 0.65 ± 0.65 | 0.9 ± 0.57* | 1.0 ± 0.62* | 0/5 |
| 4 | 0 | 0.45 ± 0.45 | 0.5 ± 0.5* | 0.65 ± 0.65* | 0.65 ± 0.65* | 1/5 |

[a]$Log_{10}$ mean virus titers ± standard error in nasal swabs post-challenge
[b]Number of positive BAL samples per group
[c]Days post-challenge (DPC)
*Values are significantly different from non-vaccinates (Group 1) within a column at $p < 0.05$ A similar study was designed that did not involve an influenza virus challenge or associated analysis; only immunogenicity of recombinant HA vaccines produced in this manner was measured in vaccinated animals. For this study the HA genes for three other influenza viruses (H1-beta, H1-delta, H1-gamma and H3) were inserted into the alphavirus replicon platform using methods as described above. Nucleotide sequencing after insertion confirmed the correct HA gene sequences had been maintained throughout the cloning process. Western blots were performed on protein lysates generated with each of the HA constructs to confirm expression of the HA protein (data not shown). In this experiment varying dilutions of the resultant HA vaccines were used to vaccinate groups of pigs (vaccines used and schedule described in the Tables 11 and 12 below); the dilutions used to vaccinate pigs are shown in Table 11. The immune responses induced by the different recombinant HA vaccines were analysed by homologous HI titers, using the method described above where endpoint titer is shown as the reciprocal of the last dilution of serum capable of inhibiting hemagglutination of the virus in the assay. A summary of the HI titers determined in this study can be found in Table 12.

TABLE 11

| Day | Task |
|---|---|
| −7 | Collect blood, treat w/antibiotics, tag, randomize |
| 0 | Vaccinate pigs |
| 21 | Collect blood, treat with booster vaccine dose |
| 28 | Collect blood for serology |
| 35 | Collect blood for serology |
| 42 | Collect blood, treat with 2$^{nd}$ booster vaccine dose |
| 57 | Euthanize animals, collect large volume blood samples |

TABLE 12

Vaccine schedule

| Antigen | Dilution (1 mL dose) | # of doses | # of animals | HI titer (µg./ml) 7 dpb |
|---|---|---|---|---|
| FLUVENT-beta | 1:60 | 3 | 2 | |
| FLUVENT-beta | 1:75 | 3 | 3 | |
| FLUVENT-delta | 1:60 | 3 | 2 | |
| FLUVENT-delta | 1:75 | 3 | 3 | |
| FLUVENT-gamma | 1:60 | 3 | 2 | |
| FLUVENT-gamma | 1:75 | 3 | 3 | |
| FLUVENT-H3 | 1:60 | 3 | 2 | |
| FLUVENT-H3 | 1:75 | 3 | 3 | |
| Noglyc + PwayM + ORF7 | 1:10 | 3 | 2 | |
| Noglyc + PwayM | 1:10 | 3 | 2 | |

TABLE 13

Hi titer 21 days post boost

| Vaccine:dilution | reciprocal HI titer |
|---|---|
| H1-beta 1:60 | 160 |
| H1-beta 1:60 | 10 |
| H1-beta 1:75 | 160 |
| H1-beta 1:75 | 160 |
| H1-beta 1:75 | 320 |
| H1-delta 1:60 | 160 |
| H1-delta 1:60 | 80 |
| H1-delta 1:75 | 80 |
| H1-delta 1:75 | 160 |
| H1-delta 1:75 | 320 |
| H1-gamma 1:60 | 320 |
| H1-gamma 1:60 | 40 |
| H1-gamma 1:75 | 160 |
| H1-gamma 1:75 | 80 |
| H1-gamma 1:75 | 10 |
| H3 1:60 | 320 |
| H3 1:60 | 40 |
| H3 1:75 | 320 |
| H3 1:75 | 160 |
| H3 1:75 | 320 |

Discussion

The outbreak of novel H1N1 in the human population has highlighted the zoonotic potential that influenza viruses possess. Even before the pandemic of this decade, there were many reported cases of swine to human transmission of influenza. As such, part of controlling this zoonotic threat is vaccination of swine against swine influenza viruses. In this study, we demonstrate how rapidly an efficacious swine influenza vaccine based on the alphavirus replicon expression system can be produced in response to an outbreak of a novel zoonotic strain. This reports on immunization of swine with a recombinant protein produced via an alphavirus replicon expression system. Replicon particle (RP) vaccines produced with this system have recently been utilized to induce protection against swine influenza virus (SIV) and porcine reproductive and respiratory syndrome virus (PRRSV) in swine. (Erdman M M, Kamrud K I, Harris D L, Smith J. 2010, Alphavirus Vector Vaccines Developed for Use in Humans Induce High Levels of Antibodies to Influenza Virus Hemagglutinin in Swine: Proof of Concept. Vaccine 28:594-596; Bosworth B, Erdman M, Stine D, Harris I, Irwin C, Jens M, Loynachan A, Owens G, Kamrud K, Harris D L. 2010, Virus-like replicon particle vaccine protects pigs against influenza Comparative Immunology, Microbiology and Infectious Diseases 33 (2010) e99-e103. The first proof of concept study demonstrated that a replicon particle vaccine administered to swine was able to induce high antibody HI titers against a human influenza strain. A subsequent study using an RP vaccine expressing the HA gene of a Glade IV H3N2 SIV isolate confirmed that influenza HA RP vaccines given to swine are not only able to induce an antibody response, but also provide significant protection against a homologous viral challenge. In contrast to these earlier studies, this study used an alphavirus replicon expression system to produce recombinant HA protein in vitro; however, similar antibody response and protection from viral challenge was demonstrated.

The results demonstrate that influenza infection in swine with A/California/04/2009 is able to induce clinical symptoms and gross lesions comparable to other strains of SIV. (Vincent A L, Ma W, Lager K M, Janke B H, Webby R J, García-Sastre A, Richt J A. Efficacy of intranasal administration of a truncated NS1 modified live influenza virus vaccine in swine. Vaccine. 2007 Nov. 19; 25(47):7999-8009. Epub 2007 Sep. 29. PubMed PMID: 17933442; PubMed Central PMCID: PMC2099695; Vincent A L, Lager K M, Ma W, Lekcharoensuk P, Gramer M R, Loiacono C, Richt J A. Evaluation of hemagglutinin subtype 1 swine influenza viruses from the United States. Vet Microbiol. 2006 Dec. 20; 118(3-4):212-22. Epub 2006 Aug. 1. PubMed PMID: 16962262; Sreta D, Kedkovid R, Tuamsang S, Kitikoon P, Thanawongnuwech R. Pathogenesis of swine influenza virus (That isolates) in weanling pigs: an experimental trial. Virol J. 2009 Mar. 25; 6:34. PubMed PMID: 19317918; PubMed Central PMCID: PMC2678088.) In contrast with a previous study, several pigs (primarily in the non-vaccinated group) in this study exhibited clinical signs, mainly coughing and sneezing. This discrepancy may be due to the miniature pig model used in the previous study (Itoh Y et al. In vitro and in vivo characterization of new swine-origin H1N1 influenza viruses. Nature. 2009 Aug. 20; 460(7258):1021-5. PubMed PMID: 19672242; PubMed Central PMCID: PMC2748827). In this study, vaccine administration induced specific antibody titers, reduced macroscopic and histopathologic lung lesions, and reduced viral load in both the nose and lung. Vaccinated pigs also demonstrated a higher average daily gain than non-vaccinates. These results demonstrate that this recombinant novel HA protein is efficacious when used as a vaccine against novel H1N1 swine influenza.

This study also demonstrated the quickness and flexibility with which a vaccine can be produced using the alphavirus replicon expression system. It took less than two months from the time the novel HA sequence was retrieved from GISAID database until pigs were administered the first vaccine dose. Traditional methods for producing influenza vaccines take much longer and are dependent on viral replication in embryonated eggs or on tissue culture cells with subsequent inactivation. In the face of an influenza epidemic, a quick turnaround is important in preventing further transmission and decreasing the zoonotic potential. The alphavirus replicon platform allows for rapid insertion of any influenza HA (or other) gene, making it an attractive influenza vaccine technology due to the constant antigenic shift and drift among influenza viruses.

Novel H1N1 has not been identified in pigs in the United States. However, it has been confirmed to exist in swine herds in several countries, including neighboring Canada. (ProMED-mail. Influenza Pandemic (H1N1) 2009, Animal health (08): Singapore, Swine. ProMED-mail; 4 September: 20090904.3114. www.promedmail.org. 2009; OIE World Animal Health Information Database. Vol 22 Nos. 18-40. Apr. 30-Oct. 1, 2009. http://www.oie.int/wahis/public.php?page=weekly_report_index&admin=0. 2009.) Several recent studies have already reported the successful transmission of novel H1N1 virus from infected to naïve contact pigs. (Brookes S M, Irvine R M, Nunez A, Clifford D, Essen S, Brown I H, Van Reeth K, Kuntz-Simon G, Loeffen W, Foni E, Larsen L, Matrosovich M, Bublot M, Maldonado J, Beer M, Cattoli G. Influenza A (H1N1) infection in pigs. Vet Rec. 2009 Jun. 13; 164(24):760-1. PubMed PMID: 19525527; Lange E, Kalthoff D, Blohm U, Teifke J P, Breithaupt A, Maresch C, Starick E, Fereidouni S, Hoffmann B, Mettenleiter T C, Beer M, Vahlenkamp T W. Pathogenesis and transmission of the novel swine-origin influenza virus A/H1N1 after experimental infection of pigs. J Gen Virol. 2009 September; 90(Pt 9):2119-23. Epub 2009 Jul. 10. PubMed PMID: 19592456.) Therefore, vaccination of pigs against novel H1N1 may prevent or delay the virus' introduction into the United States swine population or decrease its' occurrence in both swine and human populations, and may also increase consumer confidence in pork products.

Tissue or fluids from animals at a location where pigs have been exposed to influenza virus is obtained. Using the RT-PCR approach as described in Example 1, HA of the virus is isolated. The sequence encoding HA is introduced into a vector and lysis of vero cells infected with the replicon for production of HA antigen (and mixed with an appropriate adjuvant) or, in another experiment, an RP vaccine produced using the procedures described in Example 1. Pigs are administered a vaccine and morbidity and mortality results measured.

Example 3

Foot-and-mouth disease (FMD) is a highly infectious disease of cloven-hoofed animals that rapidly spreads by contact and aerosol. (Bachrach HL. Foot-and-mouth disease: worldwide impact and control measures. In: Kurstak E, Maramorosch K, editors. Viruses and environment. New York: Academic Press; 1978. p. 299-310.) Outbreaks of FMD in Taiwan, Japan, South Korea, the United Kingdom, and the Netherlands, countries that had been FMD-free for many decades, resulted in significant adverse economic consequences including slaughter of large numbers of animals and loss of export markets. Even the very limited FMD outbreak in the United Kingdom in the summer of 2007, which resulted from the escape of FMDV from the Pirbright facility that houses both the government Institute of Animal Health and the Merial vaccine manufacturing laboratory, resulted in significant economic losses (~$100 million US). These outbreaks demonstrate the vulnerability of FMD-free countries, such as the US, to this disease. Disease control procedures include restriction of animal movement, slaughter of infected and exposed animals, and vaccination in certain situations. However, current vaccines, which are chemically inactivated preparations of live virus, have a number of shortcomings including the inability to induce rapid protection.

Figure 14:
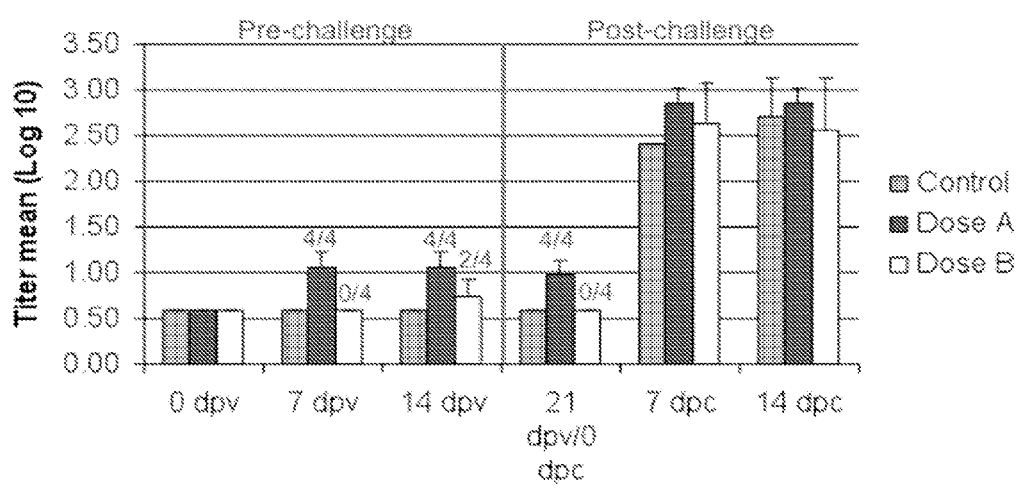
FIG. 14 is a graph showing a study measuring neutralizing antibodies against FMDV A24 at defined days post vaccination or challenge. The control is the first bar in each grouping, Dose A is the second bar and Dose B the third bar.

An RP vaccine that co-expresses the FMDV capsid and 3C proteinase coding regions was produced by engineering the capsid-3C proteinase cassette into a replicon vector and generating RP that could be used to immunize cattle. See GenBank Accession No. AY593768 (2005). The capsid-3C proteinase cassette was obtained from officials at the USDA, ARS, ARS, NAA Plum Island Animal Disease Center Foreign Animal Disease Research Unit. Data from these vaccinations is shown in the FIG. 14 and Table 14.

TABLE 14

Lesion scoring 5 Days post-FMDV challenge

| | | | Foot inspected | | | |
|---|---|---|---|---|---|---|
| Animal ID | Treatment group | Tongue | Left front | Right front | Right rear | Left rear |
| D10-27 | T02 | Pos | Neg | Neg | Neg | Neg |
| D10-32 | T02 | Pos | Neg | Neg | Neg | Neg |
| D10-33 | T02 | Pos | Neg | Neg | Pos | Neg |
| D10-35 | T02 | Pos | Neg | Neg | Neg | Neg |
| D10-26 | T03 | Neg | Neg | Neg | Neg | Neg |
| D10-28 | T03 | Pos | Pos | Pos | Pos | Pos |
| D10-30 | T03 | Pos | Neg | Neg | Neg | Neg |
| D10-31 | T03 | Pos | Pos | Pos | Pos | Pos |
| D10-29 | T01 Sham | Pos | Pos | Pos | Pos | Pos |
| D10-34 | T01 Sham | Pos | Pos | Pos | Pos | Pos |

Cattle vaccinated one time with $1\times10^9$ IU A24 RP showed nearly complete protection from systemic disease after FMDV challenge (one animal showed lesions on one hoof while all others remained symptom free). Half of the animals that received $5\times10^8$ IU of A24 RP were protected from significant systemic disease. Dose A: $1\times10^9$ IU. Dose B: $5\times10^8$ IU. Numbers shown over the columns pre-challenge represent the # positive animals/total # animals. Virus neutralization assays were run on serum collected at 0, 7, 14 and 21 days post vaccination. Results are shown below. All of the animals in the highest dose group demonstrated FMDV neutralizing antibodies by day 7 that were maintained through the day of challenge (day 21).

Two candidate rapid response vaccine approaches against foot and mouth disease virus (FMDV) are described here. The first consists of replicon RNAs that express FMDV genes packaged into particles (RP). A similar RP as described above is prepared using an autogenous source and animals vaccinated as outlined below. The purified RP represent the vaccine. The second consists of a protein lysate generated by introducing replicon RNAs that express FMDV genes into cells; a recombinant subunit (RS) lysates vaccine is then harvested by lysing the transfected cells after vaccine antigen has been produced. Both replicon-based approaches provide the ability to differentiate between vaccinated and infected animals.

Replicon vectors co-expressing the FMDV capsid and 3C proteinase coding regions of FMDV are prepared. Expression of these FMDV proteins produces virus-like particles (VLP) because the 3C proteinase processes the coat proteins allowing them to self-assemble into antigenic VLP. The P1-2A capsid coding region, the 2B coding region and the complete 3C protease coding region will be expressed. (Moraes M P, Mayr G A, Mason P W, Grubman M J. Early protection against homologous challenge after a single dose of replication-defective human adenovirus type 5 expressing capsid proteins of foot-and-mouth disease virus (FMDV) strain A24. Vaccine 2002; 20:1631-9.) Because most of the FMDV non-structural proteins are not included in the genes engineered into the replicon vector animals vaccinated with this can be unequivocally differentiated from infected animals.

Replicon clones expressing at the highest relative level and which product the highest titer RP are selected. Monoclonal antibodies are used that are cross reactive with all seven serotypes of FMCV in yield and expression analysis.

The first approach is to generate an RNA subunit (RS) vaccine by introducing the replicon RNA that expresses the FMDV capsid and 3C proteinase coding regions into cells in culture. Once the replicon carrying the FMDV genes has been introduced into cells each of the individual cells express the FMDV proteins. The FMDV proteins expressed in the cells are harvested by lysing the cells creating an FMDV protein lysate that constitutes the RS vaccine. In brief, RNA transcripts will be produced in vitro (Promega RiboMAX transcription system) from the replicon plasmid and purified by either spin-column (gel binding and elution) or size exclusion chromatography, followed by agarose gel analysis to assess integrity, and quantification by ultraviolet (UV) absorbance. Specified mass amounts of the replicon RNA will be mixed with certified Vero cells in electroporation chambers and pulsed using optimal conditions for transfection efficiency and protein expression. Electroporated cell suspensions will be seeded into individual roller bottles with media containing serum and incubated at 37° C. in 5% CO2 for 18-24 hr. Following incubation, cells are trypsinized and pelleted by centrifugation. Cells are then lysed by resuspending the cell pellet with a mammalian cell lysis buffer (RIPA Lysis and Extraction buffer, Thermo Scientific). The resultant lysate is tested for potency via Western blot analysis to confirm protein expression.

In RS potency assays, densitometry analysis of Western blots specific for FMDV VP2 capsid protein will be used to determine a relative concentration of FMDV antigen. The relative antigen concentration will be associated with a total cellular protein concentration determined using the BCA Protein Assay Reagent (bicinchoninic acid, Pierce, Rockford, Ill.) method and a bovine serum albumin protein standard curve. The maximum concentration of FMDV antigen will be based on the minimum formulation dilution possible and volume restrictions linked with practical vaccination of the test animals. In addition to the most concentrated FMDV antigen dose, two additional dilutions of FMDV antigen lysates will be formulated. The two additional dilutions will represent a 1:5 and a 1:10 dilution of the highest dose.

The second approach is to generate an FMDV RP vaccine. FMDV RP vaccines are produced by introducing into Vero cells by electroporation a replicon RNA that expresses the FMDV genes and two helper RNAs. FMDV RP are then harvested from the cells approximately 18 hours post electroporation; the RP express the FMDV capsid and 3C proteinase coding regions when introduced into animals by vaccination. In brief, RNA transcripts will be produced in vitro as described above from the replicon and helper plasmids and purified by either spin-column (gel binding and elution) or size exclusion chromatography, followed by agarose gel analysis to assess integrity, and quantification by UV absorbance. Specified mass amounts of the replicon and helper RNAs will be mixed with certified Vero cells in electroporation chambers and pulsed using various electroporation parameters to identify the optimal conditions for transfection efficiency and RP yield. Electroporated cell suspensions will be seeded into individual roller bottles containing serum-free medium and incubated at 37° C. in 5% $CO_2$ for 18-24 hr. Following incubation, media and cells from the roller bottles will be combined and pumped through a charged depth filter. RP will be eluted from the cells and filter using a high NaCl concentration buffer and stored at −80° C. until ready for use. The infectious titer of the RP preparation will be measured by antigen-specific IFA and tested at defined MOI in a CPE assay to assure the absence of detectable replication-competent virus. After a negative result is obtained from the CPE assay, the RP preparation is considered devoid of detectable RCV and can subsequently be handled under BL 1 laboratory conditions.

Potency assays are used to determine RP titer based on an IFA assay and qRT-PCR analysis to determine the number of RNAs associated with each RP. Determining the total number of RNA copies helps to assure vaccine consistency from serial to serial. The method for calculating the potency is based upon an IFA specific for the vaccine H3 antigen. The H3 positive cells are observed and quantified. Individual wells of the IFA tissue culture plate are visualized under 10× magnification and wells containing 20 to 50 H3 positive cells per grid field are used. A total of five fields per well are counted. A duplicate well is counted in the same manner. An average of the ten readings is used to calculate the potency, or RP/ml. The total number of H3 positive cells is determined by inserting the average of the ten counts into the following equation: potency=(average)×(dilution)×(100)/(0.12) where average represents the average of ten positive H3 cell counts for the sample, dilution represents the well in which the average H3 positive cells were counted, 100 is a constant representing the surface area of the wells in the tissue culture plate and 0.12 is a constant representing the volume of RNA particle vaccine tested (ml).

Densitometry analysis of Western blots specific for FMDV VP2 capsid protein will be used to determine a relative concentration of FMDV antigen. The relative antigen concentration will be associated with a total cellular protein concentration determined using the BCA Protein Assay Reagent (bicinchoninic acid, Pierce, Rockford, Ill.) method and a bovine serum albumin protein standard curve. The maximum concentration of FMDV antigen will be based on the minimum formulation dilution possible and volume restrictions linked with practical vaccination of the test animals. In addition to the most concentrated FMDV antigen dose, two additional dilutions of FMDV antigen lysates will be formulated. The two additional dilutions will represent a 1:5 and a 1:10 dilution of the highest dose.

Animals

Species/Breed/Strain: Bovine, no restriction on breed or strain

Sex: No restrictions

Approximate Initial Age: 3-6 months at time of vaccination. No weight restriction and/or weight (Day 0).

Approximate Number: 10 enrolled

Source of Supply/Origin: Animals sourced from commercial farm or production system Identification: Each animal will be identified by a uniquely numbered ear tag Conditioning/Acclimation: Acclimated ≥5 days prior to administration of investigational veterinary product (IVP)

Management/Housing: Animals will be fed and watered in accordance with the standard procedures of the study site. Animals will be handled in compliance with site Institutional Animal Care and Use Committee (IACUC) approvals and site facility regulations.

Exclusion: Only clinically healthy, animals will be enrolled in the study. Unsuitable animals will be excluded from the study at the discretion of the Investigator and/or the attending veterinarian prior to the administration of the IVP. Reasons for any animal being removed from the study will be included in the final report.

Allotment: The identification number of each enrolled animal will be recorded on the allocation plan prior to the administration of the IVP.

TABLE 15

Investigational Veterinary Product

| | |
|---|---|
| Generic Product Name | Replication-defective RP vectored Foot-and-Mouth Disease Virus subunit vaccine pERK-A24 RP (as in FIG. 3 with the PRRSV gene replaced with the FMDV sequences) |
| Formulation | RP are formulated in 1.0% fetal bovine serum, 5% sucrose, 200 mM sodium chloride in 10 mM sodium phosphate, pH 7.3. |
| In Vitro Assay Results | Sterility and titer; RCV |
| Test Article Retention | Unused material will be retained for potential use in additional studies depending on study outcome |
| Applied Dose | 1 dose containing $5 \times 10^8$ - or $1 \times 10^9$ IU/mL 2 mL per dose |
| Vaccination Route | Intramuscular (IM) |

TABLE 16

Challenge

| | |
|---|---|
| Strain | Foot-and-Mouth Disease Virus (FMDV) serotype A24 Cruzerio, SGD strain |
| Source | DHS/PIADC experimentally passaged once in bovine |
| Storage | ≤−70° C. |
| IDL Challenge Dose | Approximately $1\text{-}2 \times 10^4$ bovine infectious dose 50 ($BID_{50}$) per animal |
| IDL Challenge Route/Volume | Intradermal inoculation at multiple sites in the tongue/0.5 1.0 total mL. This route of challenge in cattle is one recommended by the OIE. |

TABLE 17

Study Groups

| Treatment | Vaccine | # of Animals | Route of Vaccine Administration | Dose Volume | Dose IU | # of Doses/Animal |
|---|---|---|---|---|---|---|
| T01 | Control (sham immunized) | 2 | IM | 2 mL | N.A. | 1 |
| T02 | pERK-A24 RP | 4 | IM | 2 mL | $1 \times 10^9$ | 1 |
| T03 | pERK-A24 RP | 4 | IM | 2 mL | $5 \times 10^8$ | 1 |

Vaccination and Challenge

On Day 0, blood from all cattle will be collected (baseline). Cattle will be vaccinated once with test article (T02, T03) or sham-immunized (T01) at Day 0. On Day 7 and 14 blood from all cattle (T01-T03) will be collected and tested for the presence of serum virus neutralizing (SVN) antibodies to FMDV A24. Cattle will be challenged with FMDV serotype A24 Cruzerio SGD strain according to OIE guidelines. For challenge administration, each animal will be sedated and then receive intradermal inoculations at multiple sites (0.5-1.0 total mL) in the upper surface of the tongue.

An RP or RS vaccine is especially useful as there currently is no approved FMDV vaccine in the US. Rather, the US would have to rely upon sources in other countries, and those vaccines would be unlikely to be effective in US strains and biotypes. With the present invention, a US based FMDV could be biotypes, and vaccine prepared quickly. Tissue or fluids from animals at a location where animals have been exposed to FMDV virus is obtained. Using the RT-PCR approach as described in Example 1, FMDV capsid and 3C proteinase coding regions of the virus are isolated. The sequences are introduced into a vector and lysis of vero cells infected with the vector or, in another experiment, an RP vaccine produced using the procedures described in Example 1. Animals are administered a vaccine and morbidity and mortality results measured.

Example 4

The following demonstrates use of interfering RNA and autogenously sourced as a vaccine for animals. Those experiments below in which IMNV vaccines and WSSV VP28 vaccines were prepared used a shrimp farm as the source of the nucleic acid of interest, first amplified in disease free animals before sequencing.

Determination of RNAi Sequences

In order to evaluate candidate sequences that would induce RNAi in response to IMNV, in vitro dsRNA was synthesized corresponding to regions of viral genome. Template DNA for in vitro transcription was created by extracting viral RNA using a commercial nucleic acid purification kit (Qiagen RNeasy Mini). cDNAs to IMNV genome were created using specific oligonucleotide primers designed from sequences available (GenBank accession no. EF061744). (Senapin, S., Phewsaiya, K., Briggs, M., Flegel, T. W., 2006. Outbreaks of infectious myonecrosis virus (IMNV) in Indonesia confirmed by genome sequencing and use of an alternative RT-PCR detection method. Aquaculture 266, 32-38.) Reverse transcription (Thermoscript RT Invitrogen) was performed by adding 5 uL of RNA extract to the reaction mix and incubated at 50 degrees for 60 minutes per manufacturer's instructions. Following reverse transcription, template cDNA (~50 ng) was added to a PCR master mix (PuReTaq Ready-To-Go PCR Beads) and thermocycling was performed using oligonucleotideprimers to specific regions of the IMNV genome (Table 18). Cycling conditions were 95° C. for 4:00 followed by 35 cycles at 94° C. for: 30, 55° C. for: 30, 72° C.1:00 and a final extension of 10:00 at 72° C.

dsRNA sequences used in experiments 1-3 (see list of sequences at end):
dsRNA #3 (SEQ ID NO: 80)
dsRNA #3 5' Truncate (SEQ ID NO: 81)
dsRNA #3 3'Truncate (SEQ ID NO: 3)
dsRNA #2 (SEQ ID NO: 4)
dsRNA #1 (SEQ ID NO: 85)
GFP dsRNA (SEQ ID NO: 6)

TABLE 18

Oligonucleotide Primer Sequences

| Primer | Sequence 5'-3' |
|---|---|
| eGFPT7F (SEQ ID NO: 7) | TAATACGACTCACTATAGGGAGAATGGTGAGCAAGGGCGAGGAGCTGT |
| eGFPT7R (SEQ ID NO: 8) | TAATACGACTCACTATAGGGAGATTACTTGTACAGCTCGTCCATGCCG |
| Pep195F (SEQ ID NO: 9) | AGAAAGTTTGTTTCGTAGAGCGAGA |
| Pep1474R (SEQ ID NO: 10) | AAAGGTGGCAGGTGTCCATACTGA |
| Pep1 95 T7F (SEQ ID NO: 11) | TAATACGACTCACTATAGGGAGAAGAAAGTTTGTTTCGTAGAGC |
| Pep1474 T7R (SEQ ID NO: 12) | TAATACGACTCACTATAGGGAGAAAAGGTGGCAGGTGTCCATAC |

TABLE 18-continued

Oligonucleotide Primer Sequences

| Primer | Sequence 5'-3' |
|---|---|
| Capsid4 F (SEQ ID NO: 13) | AATTTGGGTGGTTGGGACACATGG |
| Capsid 4 R (SEQ ID NO: 14) | CCCGACTTTCGTGCACACAACTTT |
| Capsid4T7 F (SEQ ID NO: 15) | TAATACGACTCACTATAGGGAGAAATTTGGGTGGTTGGGACACA |
| Capsid4 T7R (SEQ ID NO: 16) | TAATACGACTCACTATAGGGAGACCCGACTTTCGTGCACAC |
| RdRP1 F (SEQ ID NO: 17) | TCAACTCACTCGCAGCTGAAGGTA |
| RdRP1 R (SEQ ID NO: 18) | AATATAGCAACGTCGTCTCCGCGT |
| RdRP1 T7 F (SEQ ID NO: 19) | TAATACGACTCACTATAGGGTCAACTCACTCGCAGCTGAAG |
| RdRP1 T7 R (SEQ ID NO: 20) | TAATACGACTCACTATAGGGAATATAGCAACGTCGTCTCCG |
| VP19 T7 F (SEQ ID NO: 21) | TAATACGACTCACTATAGGGAGACGAAGCTTGGCCACCACGACT |
| VP19 T7 R (SEQ ID NO: 22) | TAATACGACTCACTATAGGGAGACGGAGCTCCTGCCTCCTCTTGGGGTAA |
| VP28F (SEQ ID NO: 23) | CGGGATCCATTGAAGGCCGCGCCATGGATCTTTCTTTCACTCT |
| VP28R (SEQ ID NO: 24) | CGGAGCTCTTACTCGGTCTCAGTGCCAGA |
| VP28 AscI F (SEQ ID NO: 25) | GAGAGGCGCGCCATGGATCTTTCTTT |
| VP28 PacI R (SEQ ID NO: 26) | TCTCTTAATTAACTACTCGGTCTCAGT |
| AscPep 1 anti F (SEQ ID NO: 27) | CTAAGGCGCGCCTAAAGGTGGCAGG |
| -ssdsRNA#3 (SEQ ID NO: 28) | CGCGTTAATTAAAGAAAGTTTGTTTCG |

Products were then cloned into pCR4.0 vectors (Zero Blunt TOPO PCR cloning kit, Invitrogen) and transformed into E. coli (TOP10, Invitrogen). Plasmids preparations from these transformants were used as the template source for in vitro dsRNA synthesis. dsRNA was prepared using Ambion MEGAscript® RNAi Kit following manufacturer's directions. Briefly, opposing T7 RNA polymerase can be used at 5' ends of one DNA template or a single T7 promoter at opposite ends of a region to be transcribed is used with two templates, or two templates transcribed to make complementary RNA molecules that are annealed. DNA templates for transcription were PCR products with addition of T7 promoter sequences amplified using the primer sequences described. (See, e.g. Ujvari, A and Martin, Conn. Identification of a Minimal Binding Element within the T7 RNA Polymerase Promoter. J. Mol. Biol. (1997) 273, 775-781; Sousa et al. (2003) "T7RNA polymerase" Prog Nucleic Acid Res Mol Biol 73:1-41.). PCR cycling conditions were 95° C. for 4:00 followed by 35 cycles at 94° C. for: 30, 61° C. for: 30, 72° C. 1:00 and a final extension of 10:00 at 72° C. These clones were then incubated overnight (16 hours) at 37° C. forming dsRNA. dsRNA products were then incubated with DNase I and RNase for 1 hour and purified using the provided columns. dsRNA synthesis was confirmed by gel electrophoresis in comparison with a molecular weight ladder (pGEM ladder, Promega) and product was quantified spectrophotometrically (BioRad Smart-Spec).

Animal Rearing

Specific pathogen free (SPF) postlarvae were received from Shrimp Improvement Systems (Plantation Key, Fla.) and reared in a biosecure animal holding facility. Animals were placed into 1000 L Poly tanks containing artificial seawater (Crystal Sea Marine Mix), an oystershell airlift biofilter, and an activated carbon filter. Animals were fed a commercial growout diet (Rangen 35/10, Buhl, Id.) until 5 grams in weight.

Preparation of Viral Inoculum

A modification of the methods from Hasson et al (Hasson, K. W., Lightner, D. V., Poulos, B. T., Redman, R. M., White, B. L., Brock, J. A., Bonami, J. R., 1995. Taura syndrome in *Penaeus vannamei*: demonstration of a viral etiology. Disease of Aquatic Organisms 23, 115-126) was used to make a clarification for viral inoculation. Briefly, whole frozen animals that tested positive for infection with IMNV by PCR were received from Shrimp Improvement Systems. Tail muscle was removed from these animals, diluted 1:3 in TN buffer (0.02 M Tris-HCl, 0.4 M NaCl, pH 7.4) and homogenized in a sterilized Waring blender for 5 minutes. The macerate was placed into centrifuge tubes and centrifuged at 4000×g. The supernatant was then removed and centrifuged again at 15,000×g for 30 minutes. A final centrifugation step was performed at 25,000×g for 60 minutes. This supernatant was diluted 1:10 in sterile 2% saline and filtered through 0.2 micron syringe filters (Whatman). This clarification was then aliquoted into cryotubes and frozen at −80° C. for challenge studies.

Determination of Challenge Dose

Figure 15:
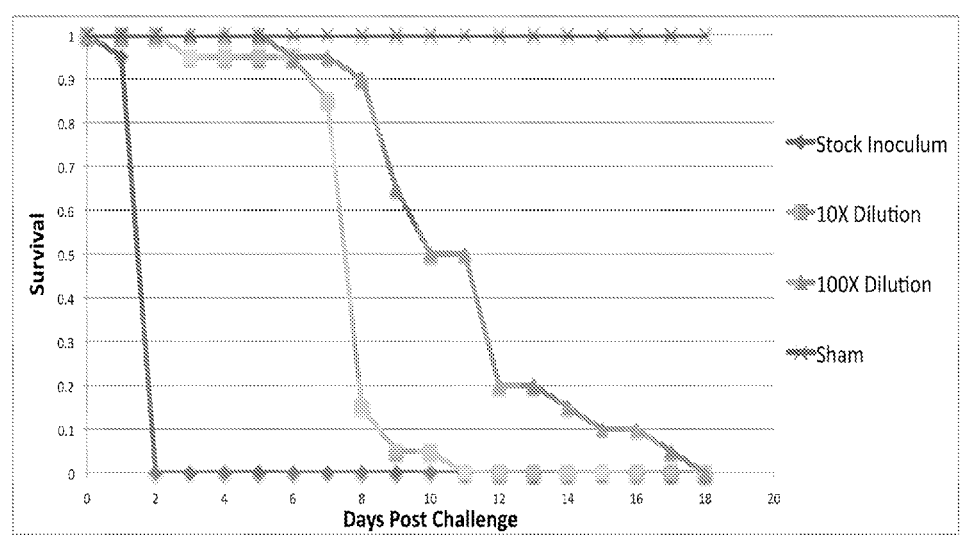
FIG. 15 is a graph showing serial dilution of clarified inoculum diluted in 2% saline. Shaminoculation received an equivalent dose of 2% saline. N=20 shrimp per treatment.

A dilution series of inoculum was prepared by diluting the prepared stock virus 10 fold and 100 fold into sterile 2% saline. Stock virus, a ten fold dilution, and a 100 fold dilution were injected into the third abdominal segment into groups of 20 naive SPF animals weighing 5-8 grams each. Animals were observed twice daily for mortality. All doses resulted in 100% mortality at varying time points. 100% mortality took 2 days for stock concentration, 7 days for ten fold dilution, and 12 days for 100 fold dilution (FIG. 15). The 100 fold dilution of the stock virus was used as the viral challenge dose for the described challenge experiments.

Histopathology

Moribund animals that were found prior to death were fixed in Davidson's fixative for 24 hours before being transferred to 70% EtOH. Tissues were embedded in paraffin, cut into slides and stained with Hematoxylin and Eosin and evaluated for the presence of IMNV lesions.

Inoculation of Animals

Double stranded RNA (dsRNA) was prepared by diluting dsRNA into RNase free water to the specified concentration. 50 µL, was injected into the muscle of the third abdominal segment of animals using a tuberculin syringe.

Study Design #1

Two hundred liter tanks containing synthetic seawater and an oystershell airlift biofilter were stocked with 20 SPF juveniles weighing 5-7 grams and allowed to acclimate for 72 hours. Following acclimation, four separate dsRNA constructs corresponding to three different segments of the IMNV genome were evaluated by comparison to a hetereologous dsRNA control. A total of 2 µg of in vitro synthesized dsRNA was inoculated into animals into randomized tanks. Following vaccination animals were challenged 48 hours later with IMNV. Animals were counted daily for mortality. Moribund animals were fixed for histopathology. Following this treatment, surviving animals from vaccination and challenge with dsRNA #3 were reared (n=16) for an additional 60 days and then rechallenged with undiluted viral stock.

Study Design #2

Two hundred liter tanks containing synthetic seawater were stocked with 10 animals weighing 5-7 grams that were allowed to acclimate for 72 hours. Following acclimation, 6 experimental groups received a dose (2, 0.2 or 0.02 µg) of a dsRNA construct (dsRNA #2 or dsRNA #3), control groups received 2 ug of a heterologous eGFP dsRNA control. These groups were then split with one being challenged 2 days following vaccination, and another being challenged 10 days following vaccination. Mortality was assessed daily and moribund animals were fixed for histopathology.

Results

Experiment #1

Figure 16:
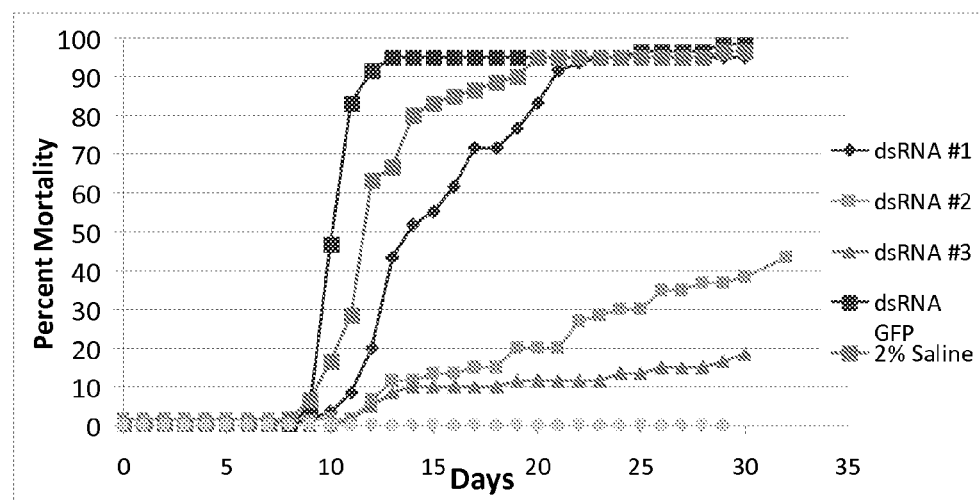
FIG. 16 is a graph showing results of Example 4, Experiment 1. Shrimp were injected with 2 ug of dsRNA construct and challenged with IMNV 48 hours following administration. N=3 groups of 20 shrimp per treatment.

Two of the dsRNA constructs demonstrated protection against IMNV challenge. dsRNA #2 (SEQ ID NO: 4) had 62% survival (38% mortality) in comparison to only 3% (97% mortality) for the non-vaccinated controls at 30 days post vaccination. The effect of dsRNA #3 (SEQ ID NO: 80) was even more robust with over 80% survival (FIG. 16). Significant differences ($P<0.05$) were calculated between dsRNA #2 and #3-injected animals as compared to controls according to Oneway ANOVA followed by Tukey's multiple comparison test using SPSS software. No significant differences were evident between animals injected with dsRNA #1, dsRNA GFP or the 2% saline control. Non-challenge controls remained at 100% survival throughout the duration of the study. Animals receiving non-sequence specific dsRNA had similar mortalities to the non-vaccinate group.

The surviving animals from dsRNA #3 (SEQ ID NO: 80) group had 100% (16/16) survival following the second challenge (60 days after the primary virus challenge) with one hundred fold higher virus concentration. This indicates that protection from challenge is robust even after an extended period of time has passed between the first and second viral challenge.

Experiment #2

Figure 17:
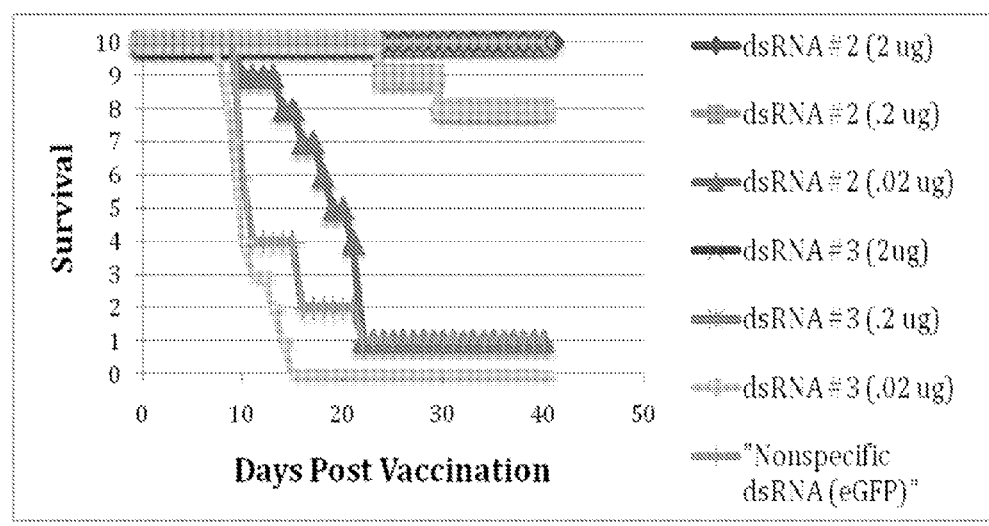
FIG. 17 is a graph showing results of Example 4, Experiment 2. Shrimp were inoculated with a serial dilution of dsRNA and challenged 48 hours following administration. N=10 shrimp per treatment.
Figure 18:
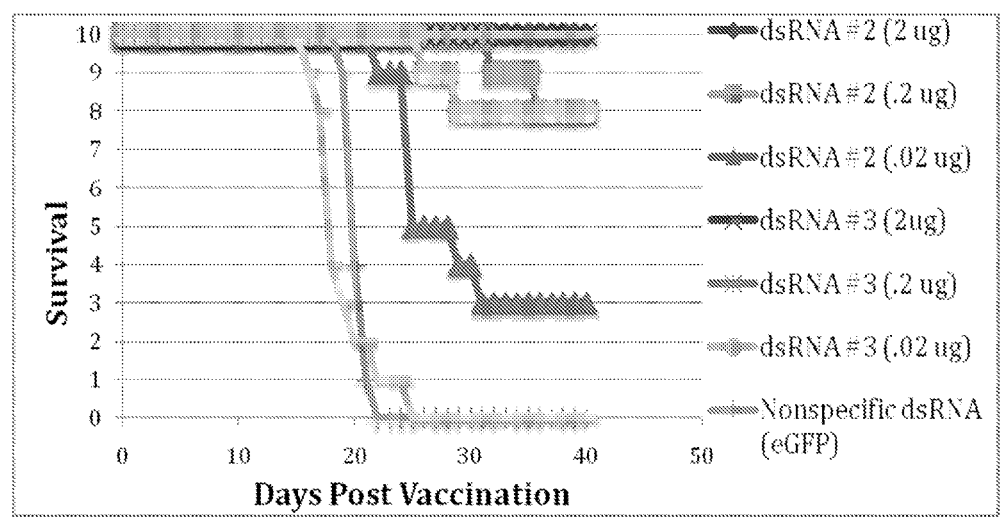
FIG. 18 is a graph showing results of Example 4, Experiment 2. Shrimp were injected with a serial dilution of dsRNA and challenged 10 days following administration. N=10 shrimp per treatment.

The construct dsRNA #3 (SEQ ID NO: 1) showed excellent protection even at the lowest dose and longest interval between vaccination and challenge at 80% survival. (FIG. 18) In comparison, low doses of dsRNA #2 (SEQ ID NO: 4) appeared to have little impact on survival with survival rates of 10% and 30% following challenge. However, non-vaccinated groups had no survival in either group and non-sequence specific administered group had 10% survival when challenged at 48 hours (FIG. 17). Non-challenged controls had survivals of 100%. After 30 days, significant differences ($P<0.05$) were noted with dsRNA #2 and #3-injected animals as compared to controls according to Oneway ANOVA followed by Tukey's multiple comparison test using SPSS software. No significant differences were evident between animals injected with dsRNA #1, dsRNA GFP or the 2% saline control.

Experiment #3

To determine whether the entire dsRNA #3 sequence was required to provide the protection noted above two additional dsRNAs that are simple truncations of the full length dsRNA #3 were tested (dsRNA #3 5' truncate and dsRNA #3 3' truncate). Animals weighing 5-7 grams were used as described above to test the new dsRNA #3 sequences (2 µg of each dsRNA were used). The construct dsRNA #3 3' truncate (SEQ ID NO: 3) was shown to be 100% protective when delivered 10 days post vaccination at a dose of 0.02 µg (FIG.

19). dsRNA 5' truncate (SEQ ID NO: 281) and the original dsRNA3 (SEQ ID NO: 80) were shown to be 90% protective at 25 days (15 days post challenge) when challenged 10 days following vaccination.

These experiments show preferred sequences having a very strong effect on dose and duration of RNAi trigger components that will be delivered through the described following vector systems.

Figure 19A:
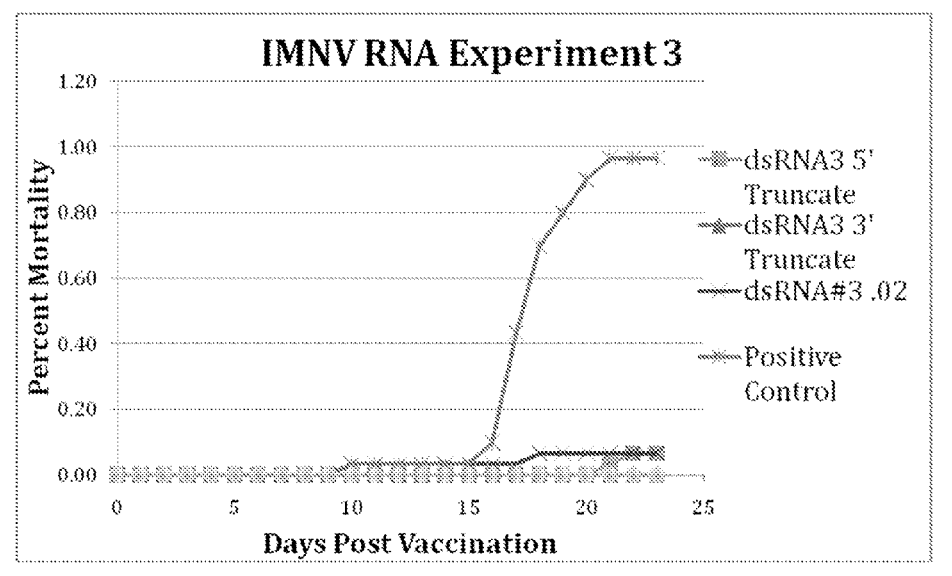
Figure 19B:
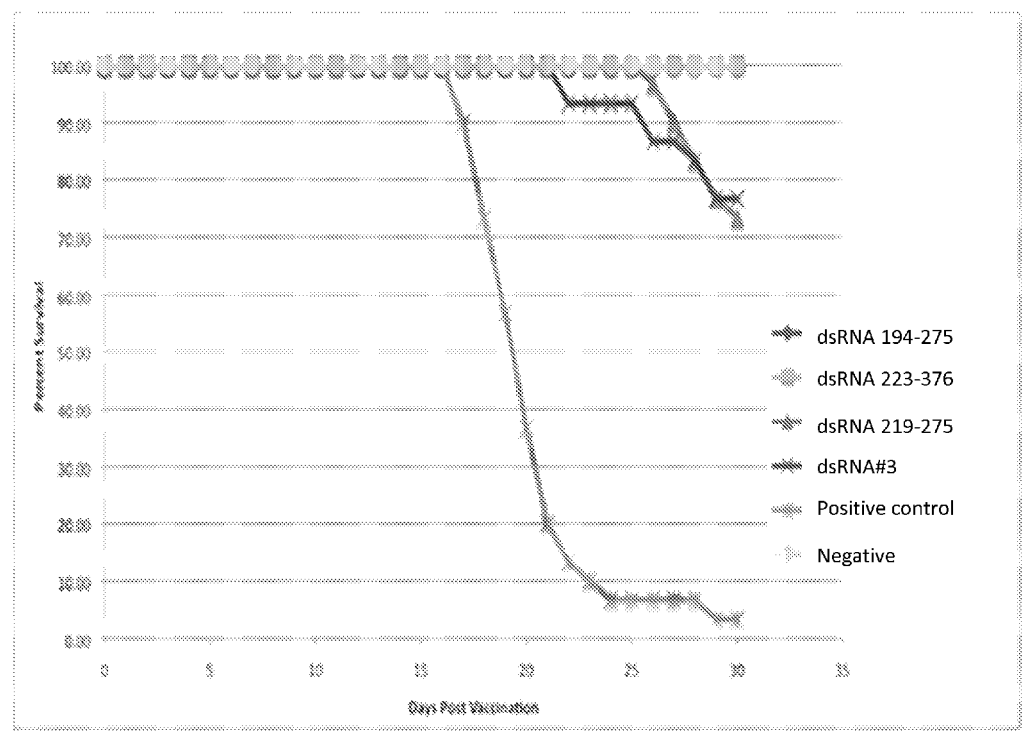
FIG. 19B is a graph showing results of Example 4, Experiment 3, where shrimp were injected as in FIG. 19A, but with further truncates of dsRNA #3.

Further truncations also showed protection, using the same procedures described above. A 15 bp sequence of SEQ ID NO: 84 (see dsRNA #3 223-376, SEQ ID NO: 61, based on the Senapin ORF1; see also SEQ ID NO: 84, which is regions 223-376 of dsRNA #3, shown at SEQ ID NO: 1 and 80) showed 100% protection, a 2 bp sequence of SEQ ID NO: 83 (see dsRNA #3 194-275, SEQ ID NO: 56, based on the Senapin ORF1; see also SEQ ID NO: 84, which is regions 194-275 of dsRNA #3, shown at SEQ ID NO: 1 and 80) showed 100% protection and a 57 bp sequence of SEQ ID NO: 82 (see dsRNA #3 219-27, SEQ ID NO: 51 based on the Senapin ORF1; see also SEQ ID NO: 82 based on regions 219-275 of SEQ ID NO: 1 and 80 and which includes a thymine of the virus at the end which the primers as shown would include) 73% protection. See FIG. 19B.

Replicon Particles

Replicon particles were produced as described, supra.

Alphavirus Replicon Proof of Concept

Alphavirus replicon particles expressing structural proteins and antisense sequences of WSSV and IMNV virus were created by cloning genes from a commercially synthesized gene sequence (GeneArt) into an existing alphavirus backbone vector. The WSSV genes of interest, in this case VP19, VP28, and the complementary sequence to VP19 (VP19 antisense) were created using a sequence derived from a virulent WSSV isolate from Thailand (AF369029.2 GI:58866698). In the case of IMNV sequences were derived from available sequence from an Indonesian isolate downloaded from GenBank (EF061744.1 GI:124303516), and reverse complement of the region spanning from 95-474 bases of the published sequence. Gene constructs were designed to include appropriate restriction sites on both the 5' and 3' ends to facilitate cloning onto the replicon plasmid. Following insertion of the protective molecule into the replicon vector, the insert was sequenced to confirm the identity of the construct (Iowa State University DNA Sequencing Facility). The replicon plasmid DNA was linearized and used to generate RNA transcripts by run-off transcription using a commercially available in vitro transcription kit (RiboMAX T7 Express, Promega). Replicon RNA containing the target gene (VP28, VP19, VP19 antisense, IMNV-ssRNA of dsRNA #3), and the two helper RNAs that code for the VEE capsid or glycoprotein genes were prepared using the same run-off transcription method. Specified (previously optimized) mass amounts of the replicon and helper RNAs were mixed with Vero cells in electroporation chambers and pulsed using previously optimized square wave electroporation parameters. Electroporated cell suspensions were seeded into roller bottles containing serum-free medium and incubated at 37° C. in 5% CO2 for 16-18 hours. Replicon particles (RP) were harvested from culture fluids and the infectious titer of the RP preparation was measured by antigen-specific IFA and tested in a cytopathic effect (CPE) assay to assure the absence of detectable replication-competent virus. RP was purified by size exclusion/ionic exchange filtration. The potency (infectious titer) of the purified bulk RP will be determined by IFA and the preparation will be formulated and frozen at −80° C. Sequences insertions used in replicon plasmids (see list of sequences at end):

VP28 (SEQ ID NO: 29)
VP19 (SEQ ID NO: 30) encoding the protein, and also transcribed to produce dsRNA
VP19-antisense (SEQ ID NO: 31)
VP19-IR (inverted repeat DNA producing dsRNA) (SEQ ID NO: 32)
DNA transcribed to produce antisense strand of dsRNA #3) (SEQ ID NO: 33)
Red Florescent Protein (RFP) (SEQ ID NO: 34)

The titer (IU/ml) of the RP preparations generated was measured. A representative example of the IU/ml titer of the RP preparations generated is: VP-19 RP=1.4E8 IU/mL, VP-28 RP=1.2E8 IU/mL, and VP19-Anti RP=5.86E7 IU/mL, IMNV RNA3 antisense=3.49E8/ml IU/mL The RP preparations all passed the CPE assay by demonstrating the absence of detectable replication competent virus. Following release assays the RP were considered appropriate for use in the studies described below. For experiment #5 an additional group of antisense VP19 replicons were created that allowed for an increase titer of 1.26E8 IU/mL.

Preparation of WSSV for use as a challenge stock virus were amplified utilizing SPF stocks of *L. vannamei* with a virulent strain of WSSV (Don Lightner, University of Arizona). Fifty (50) SPF juvenile shrimp weighing approximately 12 grams were exposed per os with infected tissue from moribund shrimp that were PCR positive for WSSV (infected tissues used were stored at −80° C. prior to use). Infected tissues were diluted 1:3 in TN buffer (0.02 M Tris-HCl, 0.4 M NaCl, pH 7.4) and homogenized in a sterilized Waring blender for 5 minutes. The macerate was placed into centrifuge tubes and centrifuged at 4000×g. The supernatant was then removed and centrifuged again at 15,000×g for 30 minutes. A final centrifugation step was performed at 25,000×g for 60 minutes. This supernatant was diluted 1:10 in sterile 2% saline and filtered through 0.2 micron syringe filters (Whatman). This clarification was then aliquoted into cryotubes and frozen at −80° C. for challenge studies. Challenge dose was then optimized by injecting SPF animals with serial dilutions of viral inoculum in 2% saline. A challenge dose of 1 part inoculum and 10,000 parts 2% saline resulted in 10-20% survival 14 days after challenge and was used for the viral challenge dose for the described studies.

Viral Challenge: Experimental animals were challenged by injection 3 days after the initial injection with RP. Experimental and control groups will be observed for mortality over a 21 day period. At the termination of the experiment the remaining individuals were sedated and euthanized in an ice slurry, fixed whole in Davidson's fixative, and submitted for histological analysis. A gill tissue sample was taken and frozen at −20° C. for PCR testing if needed.

Experiment #4 Experimental Design

SPF juvenile *L. vannamei* weighing approximately 5 grams were placed into 16 tanks containing 10 animals and synthetic seawater (Crystal Sea Marine Mix) at 30 ppt salinity and maintained at 25° C. Three replicate tanks were provided for each experimental group. Experimental animals were injected with 50 uL of RP expressing VP28 (SEQ ID NO: 29) or VP19 (SEQ ID NO: 30) at a concentration of 10E8 IU/mL or VP19 antisense RP (SEQ ID NO: 31) at a concentration of 10E7 IU/mL into the ventral sinus. A sham injection control group was injected with 50 μL of cell culture media used as a control. VP19 naked double stranded RNA (SEQ ID NOs: 49 and 50) was used as a positive vaccine control as it had provided 100% protection in previous experiments.

Experiment #5 Experimental Design

SPF juvenile *L. vannamei* weighing approximately 5 grams were placed into 15 tanks containing 10 animals and synthetic seawater (Crystal Sea Marine Mix) at 30 ppt salinity and maintained at 25° C. Experimental animals were injected with 50 uL of RP expressing VP19 at a concentration of 10E8 IU/mL or VP19 antisense RP at a concentration of 10E7 IU/mL into the ventral sinus. A sham injection control group was injected with 50 uL of cell culture media used as a control. VP19 naked double stranded RNA was used as a positive vaccine control of 10 days post vaccination as it had provided 100% protection in previous experiments Experiment #6 Experimental Design SPF larvae and postlarvae were be placed into petri dishes containing 25 mL seawater and 10E7 IU/mL of RP expressing the RFP reporter protein. Immersion exposure was done at room temperature for 2 hours. Animals were then transferred to 500 mL flasks containing seawater and an airstone. Whole larvae were sacrificed at 24, 48, and 72 hours post-exposure and evaluated for fluorescence using epifluorescence microscopy. Control animals were immersed into tanks containing cell culture media, and evaluated using the same method. This study was used to determine if a) RP infectivity remains intact through the digestive tract and b) RP are able to infect and express a foreign protein in larval and post larval animals.

Experiment #7

SPF juvenile *L. vannamei* weighing approximately 5 grams were placed into tanks containing 10 animals and synthetic seawater (Crystal Sea Marine Mix) at 30 ppt salinity and maintained at 25° C. To evaluate the duration of immune response for extended periods of time in animals administered specific dsRNA or non-specific dsRNA animals were given specific dsRNA (VP19 or VP28) or non-specific (eGFP) by IM injection (5 µg) and challenged 3 days following administration. Following the primary challenge in which only slight mortality was observed, a second challenge was performed 21 days later.

Experiment #8

In order to compare methods of delivery, and determine if an orally delivered sequence was protective, SPF juvenile *L. vannamei* weighing approximately 5 grams were placed into tanks containing 10 animals and synthetic seawater (Crystal Sea Marine Mix) at 30 ppt salinity and maintained at 25° C. Experimental animals were fasted for 24 hours, injected with 5 µg of dsRNA VP19 or reverse gavaged (enema) with 5 ug VP19 dsRNA diluted in sterile water. Animals were challenged 14 days after vaccine administration.

Results

Experiment #4

Figure 20:
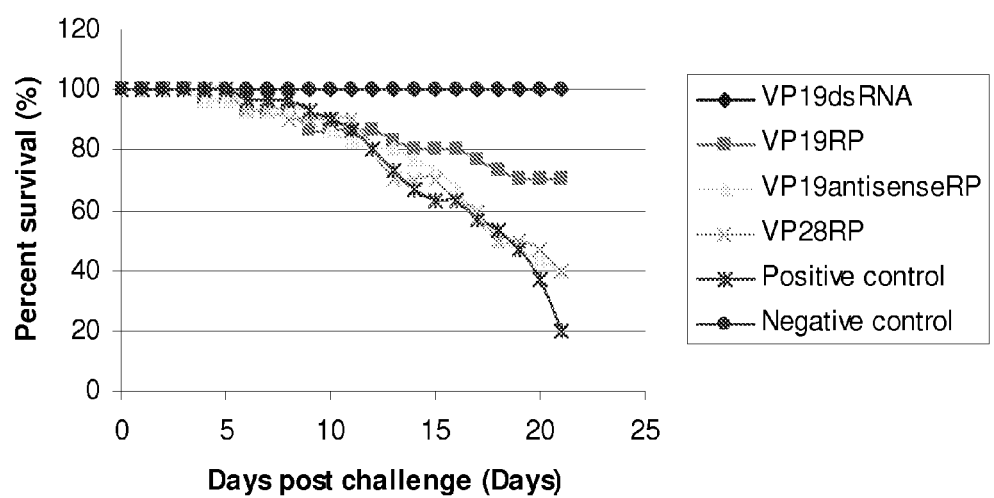
FIG. 20 is a graph showing results of Example 4, Experiment 4 Shrimp were inoculated with replicons or dsRNA a16nd challenged 3 days following administration. N=3 groups of 10 shrimp per treatment.

At 21 days post challenge, VP19 dsRNA (Control), VP19 RP, VP19 antisense RNA-RP or VP28 RP showed 100%, 70%, 40% and 40% survival respectively. The positive control group showed 20% survival (FIG. 20). This study demonstrates that VP19 dsRNA and VP19 expressed by RP provide protection against mortality due to WSSV. As seen in Experiment 1 and 7, protection up to at least 24 days was observed. Referring to FIGS. 16, 17, 18 and 19B. protection up to at least 30 and at least 40 days is provided. This study will be repeated and duration of this protection following inoculation will be assessed.

Experiment #5

Figure 21:
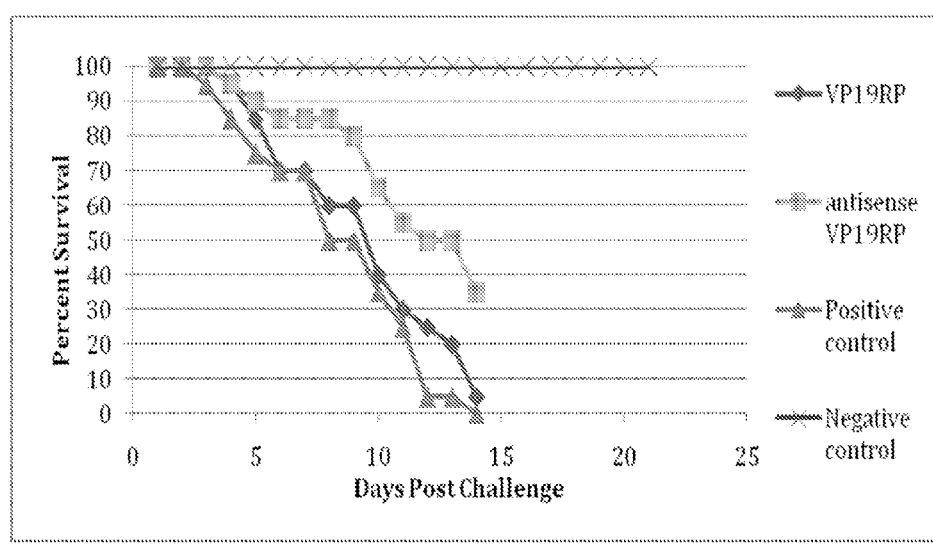
FIG. 21 is a graph showing results of Example 4, Experiment 5 Shrimp were inoculated with replicon and challenged 3 days following administration. N=3 groups of 10 shrimp per treatment.
Figure 22:
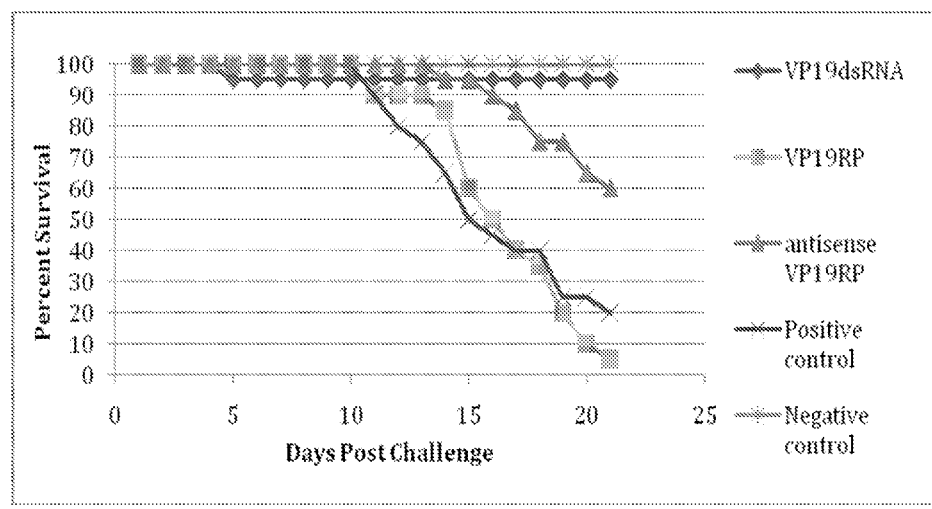
FIG. 22 is a graph showing results of Example 4, Experiment 5 Shrimp were inoculated with replicon and challenged 10 days following administration. N=3 groups of 10 shrimp per treatment.

For the group that was challenged 3 days post vaccination, VP19 RP, VP19 antisense-RP and positive control group showed 5%, 35% and 0% survival, respectively 14 days post challenge. For the group that was challenged 10 days post vaccination VP19 dsRNA (Control), VP19 RP and VP19 antisense RNA-RP showed 95%, 5% and 60% survival 21 days post challenge, respectively. The positive control group for the 10 day post vaccination group showed 20% overall survival. See FIGS. 21 and 22.

Experiment #6

Fluorescence was difficult to evaluate in the post larval stages due to autofluorescence present in the gut tissue in both controls and experimental groups. In contrast, the larval stages evaluated (Mysis and Zoea) demonstrated strong specific RFP fluorescence in both gut and gills when compared with controls at 48 and 72 hours post inoculation with RFP RP. This shows that protein can be delivered to the aquatic invertebrate digestive tract and that immersion vaccination of larval animals provides a feasible delivery system for replicon particles.

Experiment #7

Figure 23:
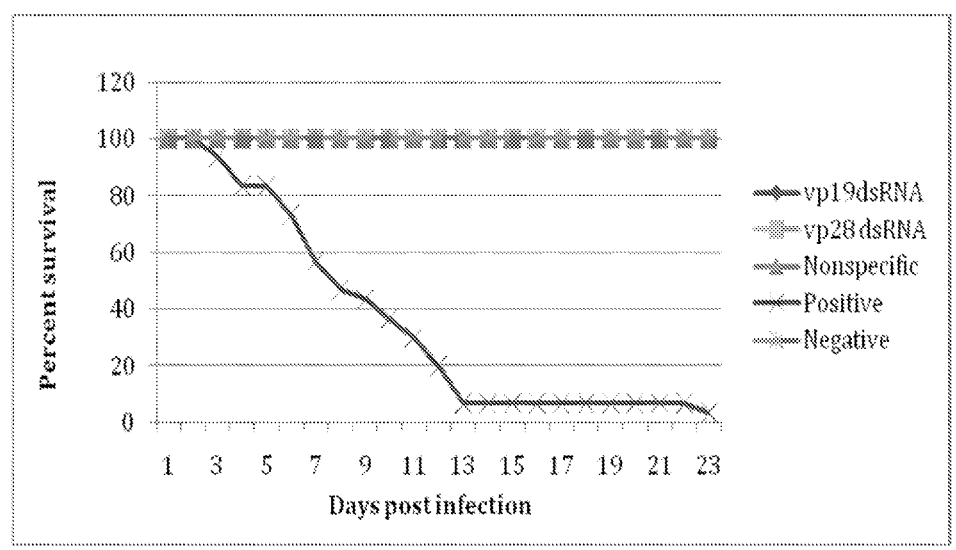
FIG. 23 is a graph showing results of Example 4, Experiment 7 WSSV survival following primary challenge.
Figure 24:
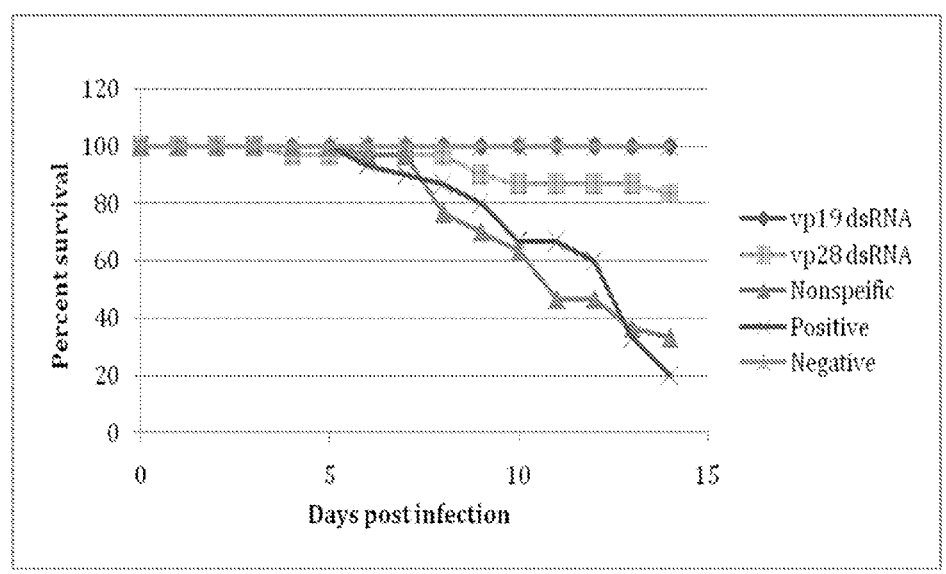
FIG. 24: Survival following secondary WSSV challenge 21 days following primary challenge.

Differences in survival were observed between VP19 (100% survival), VP28 (83%), Non-specific dsRNA (33.3%) and unvaccinated control (20%) (FIGS. 23, 24) following challenge at 21 days. This demonstrates the differences between specific and non-specific dsRNA in the duration of the protective response.

Experiment #8

Figure 25:
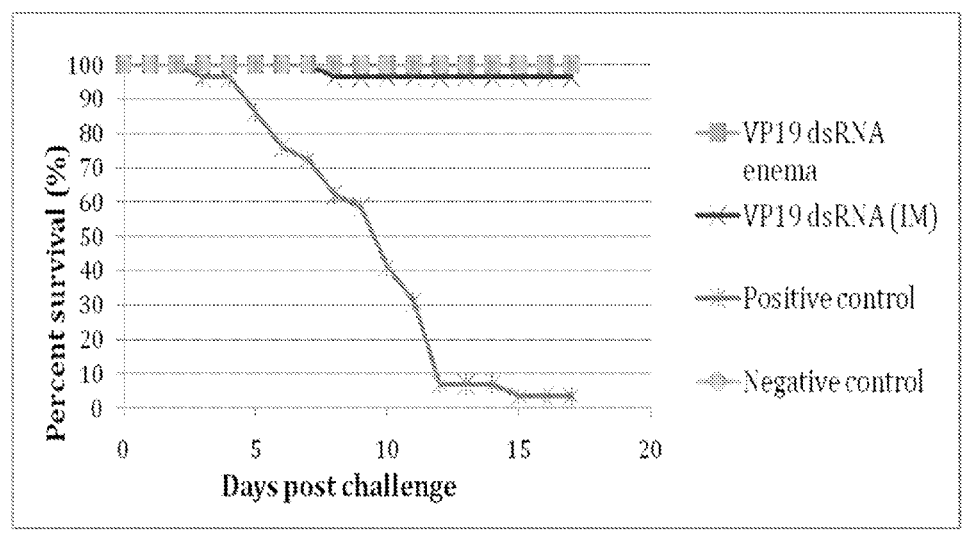
FIG. 25 is a graph showing survival following vaccination via injection or reverse gavage. Animals were challenged 14 days post vaccination.

Animals administered VP19 dsRNA via IM and reverse gavage demonstrated protection (95% and 100% survival respectively) versus controls. (FIG. 25)

Experiment #9

Study Design:

200 L tanks were stocked with 3-5 gram SPF growth line animals and allowed to acclimate for 24 hours. Tanks were equipped with an oystershell airlift biofilter that has been allowed to mature in an LT tank with ammonia. Animals were divided into three groups, one receiving dsRNA3 82 bp dsRNA fragment, one receiving eGFP (green fluorescent protein (GFP) gene (Sheen et al., Plant J. (1995) 8(5):777-84) as a heterologous dsRNA control treatment, and one receiving sterile water as a no dsRNA treatment. The dsRNA treatment groups received a 100 uL injection containing 5 µg of in vitro synthesized dsRNA 2 days following challenge with IMNV. Animals were challenged 2 days prior to dsRNA vaccination with a 1:100 dilution of IMNV clarification. Groups were counted daily for 30 days and evaluated for mortality. Moribund animals were fixed in Davidson's solution for histopathology and muscle tissues taken for qPCR analysis. Animals were frozen at −80 degrees at termination of study.

Primers used for producing the dsRNA #3 were SEQ ID NO: 59, SEQ ID NO: 60, to produce SEQ ID NO: 83. Primers for producing GFP included SEQ ID NO: 7, SEQ ID NO: 8 and SEQ ID NO: 6 is the DNA producing GFP dsRNA for control.

TABLE 19

| Treatments | Number of shrimp | Replications | Challenge interval |
|---|---|---|---|
| dsRNA #3 82 bp - 2 dpc | 10 | 3 | −2 days |
| dsRNA #3 82 bp - 2 dpc | 10 | | −2 days |
| dsRNA #3 82 bp - 2 dpc | 10 | | −2 days |
| eGFP 2 dpc | 10 | 3 | −2 days |
| eGFP 2 dpc | 10 | | −2 days |
| eGFP 2 dpc | 10 | | −2 days |
| Challenge Control | 10 | 3 | −2 days |
| Challenge Control | 10 | | −2 days |
| Challenge Control | 10 | | −2 days |

Results

Figure 26:
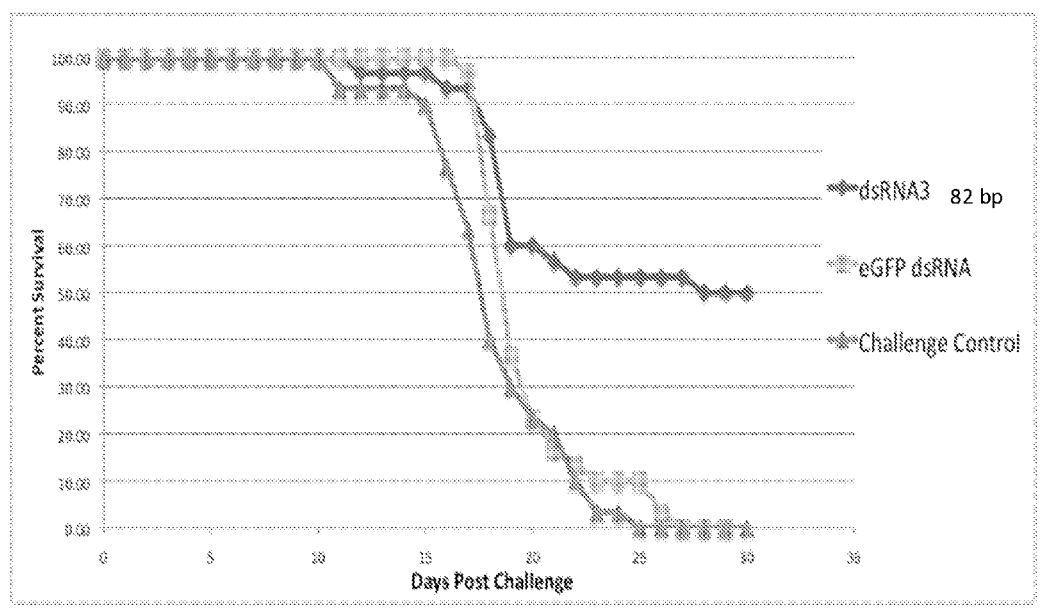
FIG. 26 is a graph showing survivorship of animals following challenge that were administered dsRNA 2 days post challenge. X-axis is days post challenge. Y-axis is percent survival. dsRNA3 and eGFP dsRNA groups were treated with 5 ug dsRNA and the challenge control was treated with an equivalent volume sterile water.

Animals receiving a treatment of dsRNA3 82 bp demonstrated a 50% survival following challenge with IMNV. In comparison, animals receiving either eGFP dsRNA or sterile water as a control demonstrated 0% survival (FIG. 26).

Conclusions dsRNA 3 82 bp can successfully reduce mortality when administered 2 days post infection with IMNV.

Experiment #10

Experimental Animals

Specific pathogen free (SPF) juvenile *L. vannamei* weighing 3-5 grams were stocked into 200 L tanks (10 animals/tank) and allowed to acclimate for 48 hours. Each tank contained artificial seawater with oystershell biofilter and activated carbon.

Feed formulation

Chitosan encapsulated particles were prepared using VP19 dsRNA, supra SEQ ID NO: 30), or IMNV dsRNA3 (not truncated, SEQ ID NO: 80). 0.2 grams chitosan was dissolved in 100 ml sodium acetate buffer. 1.0 mL of this solution was then transferred to a new bottle with 99 ml of 50 mM sodium acetate buffer (1:100 dilution), resulting in a 0.002% w/v solution of chitosan. 120 ug of each dsRNA (VP 19 and dsRNA3) were diluted in a sodium sulfate solution (0.2 M sodium acetate and 0.2 M acetic acid) to a total volume of 300 ul. 300 ul dsRNA solution was combined with 300 ul 0.002% chitosan solution. The solution was heated in a 55 C water bath for 1 minute, and promptly vortexed for 30 seconds. The tubes were then centrifuged at 13,200×g for 10 minutes. Following the centrifugation, the solution was resuspended by pipetting and top coated onto 1 gram ground feed. The entire 600 ul of the chitosan-dsRNA solution was added first, followed by 600 ul 2% agarose. The feed was then blended with pipette tip to create evenly mixed clumps, which solidified after several minutes.

Experimental Design

TABLE 20

| Treatments | # Shrimp | Replications (# of tanks) | Survival (%) |
|---|---|---|---|
| 1. VP19 dsRNA chitosan nanoparticles | 10 | 3 | 33% |
| 2. IMNV dsRNA3 chitosan nanoparticles | 10 | 3 | 0 |
| 3. VP19 dsRNA without chitosan | 10 | 3 | 67% |
| 4. Positive control | 10 | 3 | 0 |

After 3 days shrimp in each treatment group were challenged 100 uL with 0.2 micron filtered WSSV clarification diluted in 2% sterile saline at WSSV $1:1\times10^5$. Daily feeding of 10% biomass and 10% water exchange was performed daily to remove molts, excess food and fecal material. Mortality was observed for 21 days and samples of dead animals were frozen at −80 for further testing.

Results

Figure 27:
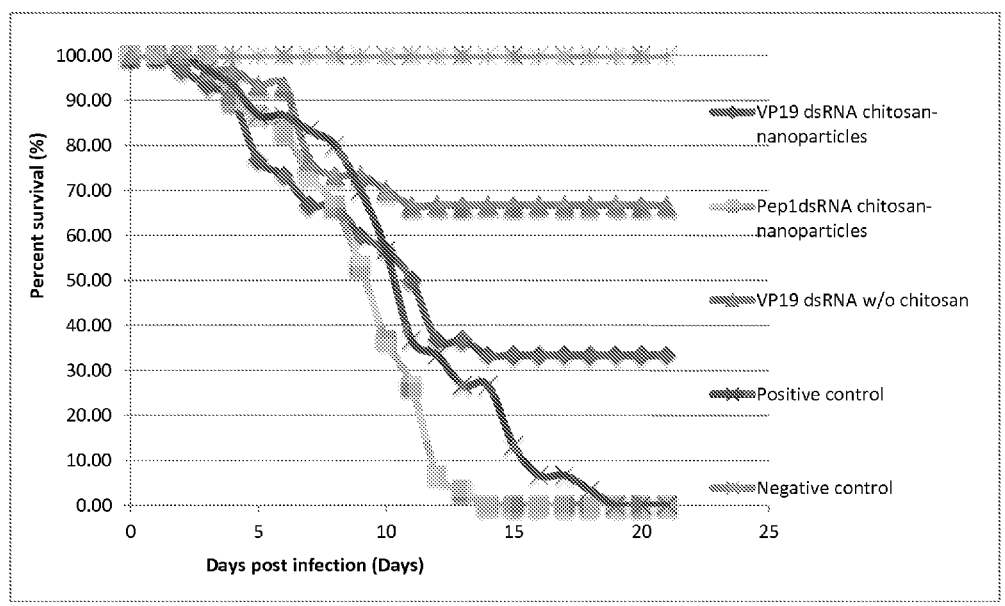
FIG. 27 is a graph showing percent survivorship of shrimp following treatment with feed containing different solutions. X-axis is days post infection with WSSV and Y-axis is percent of animals surviving. n=30 animals with 3 replicates of 10/treatment

Following challenge with WSSV, animals that were treated with feed coated with VP19 dsRNA demonstrated 67% survival. In addition, groups that were treated with feed coated with chitosan nanoparticles containing VP19 dsRNA demonstrated 33% survival following challenge with WSSV. Animals that received sham treatment in the feed (Positive Control) had 0% survival following challenge. (See FIG. 27).

Experiment #11

HV156: dsRNA duration

The experiment demonstrated dsRNAS82(194-275) and dsRNA3 (95-474) vaccination efficacy at 30 days post vaccination 15×200 L tanks were stocked with 3-5 gram SPF growth line animals and allowed to acclimate for 24 hours. Tanks were equipped with an oystershell airlift biofilter that has been allowed to mature in an LT tank with ammonia. The dsRNA treatment groups received a 100 µL injection containing 2.0 µg of dsRNA (DE3 fermentation production lots see Timmons et al 2001) diluted in RNase free water. Animals were then challenged 30 days after dsRNA administration with a lethal dose of IMNV via injection. Groups were evaluated daily for 21 days following challenge and evaluated for clinical signs and mortality.

TABLE 21

| Treatments | Number of shrimp | Replications | Challenge Material | Challenge interval | Random Tank Numbers |
|---|---|---|---|---|---|
| DE3 dsRNA3 | 10 | 1 | 1:100 | 30 days | L |
| DE3 dsRNA3 | 10 | 1 | 1:100 | 30 days | K |
| DE3 dsRNA3 | 10 | 1 | 1:100 | 30 days | E |
| DE3 dsRNA82 | 10 | 1 | 1:100 | 30 days | C |
| DE3 dsRNA82 | 10 | 1 | 1:100 | 30 days | P |
| DE3 dsRNA82 | 10 | 1 | 1:100 | 30 days | S |
| Challenge Control | 10 | 1 | 1:100 | 30 days | Q |
| Challenge Control | 10 | 1 | 1:100 | 30 days | H |
| Challenge Control | 10 | 1 | 1:100 | 30 days | B |

Results

Figure 28:
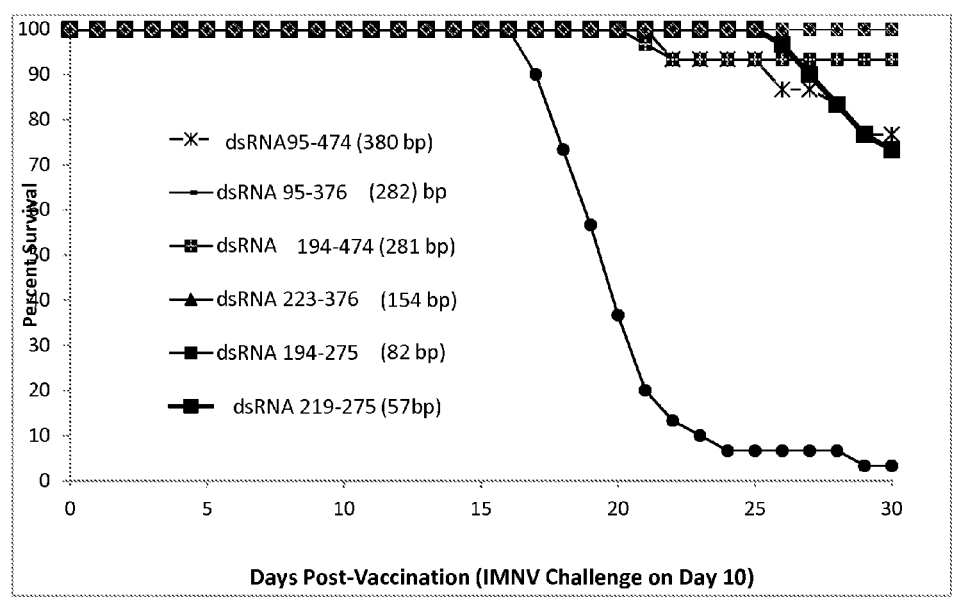
FIG. 28 is a graph showing shrimp survival post-vaccination with dsRNA of varying lengths (day 0) and post IMNV infection (day 10). dsRNA target position on the IMNV genome and length are indicated in the key.

The study was terminated on Day 51 (21 days post challenge). Upon termination survival in treatment groups was significantly higher ($P<0.0001$ using Tukey's HSD following One-Way ANOVA) than controls. Animals administered dsRNA3 had 100% survival following administration of dsRNA3, animals given dsRNA82 had a mean survival of 93.33% (90%, 90%, and 100%). Sham administration controls had 6.67% mean survival at termination (0%, 10%, and 10%) (FIG. 28).

Conclusions dsRNA3 and dsRNA82 production lots made in DE3 *E. coli* are highly protective against lethal IMNV challenge up to 30 days post administration.

LIST OF SEQUENCES

SEQ ID NO: 1 DNA producing dsRNA #3
SEQ ID NO: 2 DNA producing dsRNA #3 5' Truncate
SEQ ID NO: 3 DNA producing dsRNA #3 3'Truncate
SEQ ID NO: 4 DNA producing dsRNA #2
SEQ ID NO: 5 DNA producing dsRNA #1
SEQ ID NO: 6 DNA producing GFP dsRNA
SEQ ID NO: 7: Primer eGFPT7F
SEQ ID NO: 8 Primer eGFPT7R
SEQ ID NO: 9 Primer Pep1 95F
SEQ ID NO: 10 Primer Pep1 474R
SEQ ID NO: 11 Primer Pep1 95 T7F
SEQ ID NO: 12 Primer Pep1 474 T7R
SEQ ID NO: 13 Primer Capsid4 F
SEQ ID NO: 14 Primer Capsid 4 R
SEQ ID NO: 15 Primer Capsid4T7 F
SEQ ID NO: 16 Primer Capsid4 T7R
SEQ ID NO: 17 Primer RdRP1 F
SEQ ID NO: 18 Primer RdRP1 R
SEQ ID NO: 19 Primer RdRP1 T7 F
SEQ ID NO: 20 Primer RdRP1 T7 R
SEQ ID NO: 21 Primer VP19 T7 F
SEQ ID NO: 22 Primer VP19 T7 R
SEQ ID NO: 23 Primer VP28F
SEQ ID NO: 24 Primer VP28R
SEQ ID NO: 25 Primer VP28 AscI F
SEQ ID NO: 26 Primer VP28 PacI R SEQ ID NO: 27 Primer AscPep1anti F
SEQ ID NO: 28 Primer PacPep1anti R
SEQ ID NO: 29 DNA encoding VP28 and also transcribed to produce dsRNA
SEQ ID NO: 30 DNA encoding VP19 and transcribed to produce dsRNA
SEQ ID NO: 31 VP19-antisense DNA
SEQ ID NO: 32 VP19-Inverted repeat DNA producing dsRNA
SEQ ID NO: 33 DNA transcribed to produce dsRNA #3 −ssRNA
SEQ ID NO: 34 DNA encoding RFP
SEQ ID NO: 35 +ss RNA3
SEQ ID NO: 36 −ssRNA3
SEQ ID NO: 37 +ssRNA3 5' Truncate
SEQ ID NO: 38 −ssRNA3 5' Truncate
SEQ ID NO: 39 +ssRNA3 3' Truncate
SEQ ID NO: 40 −ssRNA3 3' Truncate
SEQ ID NO: 41 +ssRNA #2
SEQ ID NO: 42 −ssRNA #2
SEQ ID NO: 43 +ssRNA dsRNA1
SEQ ID NO: 44 −ssRNA dsRNA1
SEQ ID NO: 45 eGFP +ssRNA
SEQ ID NO: 46 eGFP −ssRNA
SEQ ID NO: 47 VP28 +ssRNA
SEQ ID NO: 48 −ssRNA VP28
SEQ ID NO: 49 VP19 +ssRNA
SEQ ID NO: 50 VP19 −ssRNA
SEQ ID NO: 51 dsRNA #3 219-273 sequence
SEQ ID NO: 52 dsRNA #3 219-273+RNA sequence
SEQ ID NO: 53 dsRNA #3 219-273-RNA sequence
SEQ ID NO: 54 T7 dsRNA #3 219 Forward primer:
SEQ ID NO: 55 T7 dsRNA #3 273 Reverse primer:
SEQ ID NO: 56 dsRNA #3 194-275 sequence
SEQ ID NO: 57 dsRNA #3 194-275+RNA sequence
SEQ ID NO: 58 dsRNA #3 194-275-RNA sequence
SEQ ID NO: 59 T7 dsRNA #3 194 Forward primer
SEQ ID NO: 60 T7 dsRNA #3 275 Reverse primer
SEQ ID NO: 61 dsRNA #3 223-376 sequence
SEQ ID NO: 62 dsRNA #3 223-376+RNA sequence
SEQ ID NO: 63 dsRNA #3 223-376-RNA sequence
SEQ ID NO: 64 T7 dsRNA #3 223 Forward primer
SEQ ID NO: 65 T7 dsRNA #3 376 Reverse primer
SEQ ID NO: 66 IMNV genome—Poulos
SEQ ID NO: 67 IMNV genome—Senapin
SEQ ID NO: 68 IMNV polypeptide—ORF 1 of Poulos et al.
SEQ ID NO: 69 IMNV polypeptide—ORF1 of Senapin et al.
SEQ ID NO: 70 IMNV polypeptide—ORF 2 of Poulos et al.
SEQ ID NO: 71 IMNV polypeptide—ORF 2 of Senapin et al.
SEQ ID NO: 72 IMNV ORF1 (nucleotides 136-4953 of SEQ ID NO: 66)
SEQ ID NO: 73 IMNV ORF2 (nucleotides 5241-7451 of SEQ ID NO: 66)
SEQ ID NO: 74 IMNV nucleotide sequence encoding Peptide 1 (136-415 of SEQ ID NO: 66
SEQ ID NO: 75 IMNV nucleotide sequence encoding Peptide 2 (415-1266 of SEQ ID NO: 66)
SEQ ID NO: 76 IMNV nucleotide sequence encoding Peptide 3 (1267-2247 of SEQ ID NO: 66)
SEQ ID NO: 77 IMNV nucleotide sequence encoding major capsid protein (2227-4953 of SEQ ID NO: 66)
SEQ ID NO: 78 IMNV nucleotide sequence encoding RNA dependent RNA polymerase (5241-7451 of SEQ ID NO: 66)
SEQ ID NO: 79 dsRNA Pep1
SEQ ID NO: 80 dsRNA #3 (380 bp) 95-474
SEQ ID NO: 81 dsRNA #3 5' truncate 194-474
SEQ ID NO: 82 dsRNA 219-275
SEQ ID NO: 83 dsRNA194-275
SEQ ID NO: 84 dsRNA 223-376
SEQ ID NO: 85 dsRNA5518-6388

What is claimed is:

1. A method of protecting shrimp from disease, the method comprising,
   a) identifying a target nucleic acid molecule of a microorganism causing said disease;
   b) preparing a composition comprising a protective molecule selected from the group consisting of:
      (i) a dsRNA molecule comprising at least one RNA molecule that is capable of hybridizing to said target nucleic acid molecule of said microorganism; and
      (ii) an antisense RNA molecule comprising a sequence that is the full or partial complement of said target nucleic acid molecule of said microorganism,
   wherein said composition does not comprise an expression cassette or vector comprising said protective molecule; and
   c) orally administering said composition comprising said protective molecule to shrimp wherein said shrimp is protected from said disease.

2. The method of claim 1, wherein said at least one RNA molecule comprising a sequence that corresponds to all or a portion of said target nucleic acid molecule is selected from the group consisting of an RNA molecule of at least 10 bp, at least 20 bp, at least 30 bp and at least 50 bp.

3. The method of claim 1, wherein said dsRNA comprises at least one RNA molecule that is the full or partial complement of all or a portion of said target nucleic acid molecule.

4. The method of claim 3, wherein said at least one RNA molecule comprising a sequence that corresponds to all or a portion of said target nucleic acid molecule and said at least one RNA molecule that is the full or partial complement of all or a portion of said target nucleic acid molecule is selected from the group consisting of an RNA molecule of at least 10 bp, at least 20 bp, at least 30 bp and at least 50 bp.

5. The method of claim 1, wherein said disease comprises White Spot Syndrome Virus (WSSV).

6. The method of claim 1, wherein said target nucleic acid molecule comprises a nucleic acid molecule encoding White Spot Syndrome Virus (WSSV) VP19 or a fragment thereof, wherein said nucleic acid molecule or fragment thereof produces a protective molecule that when administered to said shrimp, protects said shrimp from said WSSV.

7. The method of claim 6, wherein said target nucleic acid molecule comprises SEQ ID NO: 30 or a fragment thereof.

8. The method of claim 1, wherein said dsRNA is produced by a nucleic acid molecule comprising SEQ ID NO: 32, or the complement thereof, or a fragment of said nucleic acid molecule, wherein said dsRNA produces a protective response.

9. The method of claim 3, wherein said sequence that corresponds to all or a portion of said target nucleic acid molecule is selected from the group consisting of SEQ ID NO: 35, SEQ ID NO: 37, SEQ ID NO: 39, SEQ ID NO: 41, SEQ ID NO: 52, SEQ ID NO: 57, and SEQ ID NO: 62 and a fragment thereof, and said RNA that is the full or partial complement of all or a portion of said target nucleic acid molecule is selected from the group consisting of SEQ ID NO: 36, SEQ ID NO: 38, SEQ ID NO: 40, SEQ ID NO: 42, SEQ ID NO: 53, SEQ ID NO: 58, and SEQ ID NO: 63 and a fragment thereof.

10. The method of claim 3, wherein said sequence that corresponds to all or a portion of said target nucleic acid comprises SEQ ID NO: 49 or fragments thereof, and said RNA that is the full or partial complement of all or a portion of said target nucleic acid molecule comprises SEQ ID NO: 50 or fragments thereof.

11. The method of claim 1, wherein protective molecule is administered such that said molecule is delivered to the digestive tract of said shrimp.

12. The method of claim 1, wherein said animal is protected from said disease for a period of time selected from the group consisting of at least 20 days, at least 25 days, at least 30 days, at least 40 days and at least 60 days following administration of said protective molecule.

13. A method of protecting shrimp from disease, the method comprising,
 a) identifying a target nucleic acid molecule of a microorganism causing said disease;
 b) preparing a composition comprising a protective molecule comprising
  a dsRNA molecule comprising at least one RNA molecule that is capable of hybridizing to said target nucleic acid molecule of said microorganism,
 wherein said composition does not comprise an expression cassette or vector comprising said protective molecule; and
 c) orally administering said composition comprising said protective molecule to said shrimp, wherein said shrimp is protected from said disease.

14. A method of protecting shrimp from disease, the method comprising,
 a) identifying a target nucleic acid molecule of a microorganism causing said disease;
 b) preparing a composition comprising a protective comprising
  an antisense RNA molecule comprising a sequence that is the full or partial complement of said target nucleic acid molecule of said microorganism,
 wherein said composition does not comprise an expression cassette or vector comprising said protective molecule; and
 c) orally administering said composition comprising said protective molecule to said shrimp, wherein said shrimp is protected from said disease.

15. The method of claim 14 wherein said protective molecule comprises SEQ ID NO: 31 or a fragment thereof, wherein said, protective molecule when administered to said shrimp protects said shrimp from said disease.

* * * * *